(12) United States Patent
Wu et al.

(10) Patent No.: US 12,194,087 B2
(45) Date of Patent: *Jan. 14, 2025

(54) METHOD OF INHIBITING ENVELOPED VIRUS BINDING TO TARGET CELLS BY INCORPORATING P-SELECTIN GLYCOPROTEIN LIGAND-1 (PSGL-1) INTO VIRIONS

(71) Applicant: George Mason University, Fairfax, VA (US)

(72) Inventors: Yuntao Wu, Fairfax, VA (US); Deemah Dabbagh, Fairfax, VA (US); Sijia He, Fairfax, VA (US)

(73) Assignee: George Mason University, Fairfax, VA (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/838,264

(22) Filed: Apr. 2, 2020

(65) Prior Publication Data

US 2020/0316190 A1  Oct. 8, 2020

Related U.S. Application Data

(60) Provisional application No. 62/828,381, filed on Apr. 2, 2019.

(51) Int. Cl.
| | |
|---|---|
| *A61K 39/21* | (2006.01) |
| *C07K 14/705* | (2006.01) |
| *C12N 7/04* | (2006.01) |
| *C12N 15/85* | (2006.01) |
| *A61K 39/00* | (2006.01) |
| *A61K 39/145* | (2006.01) |
| *C12N 7/00* | (2006.01) |

(52) U.S. Cl.
CPC ........ *A61K 39/21* (2013.01); *C07K 14/70596* (2013.01); *C12N 7/04* (2013.01); *C12N 15/85* (2013.01); *A61K 39/145* (2013.01); *A61K 2039/5252* (2013.01); *A61K 2039/5254* (2013.01); *A61K 2039/5258* (2013.01); *C12N 7/00* (2013.01); *C12N 2740/13023* (2013.01); *C12N 2740/13034* (2013.01); *C12N 2740/15023* (2013.01); *C12N 2740/15034* (2013.01); *C12N 2760/16023* (2013.01); *C12N 2760/16034* (2013.01)

(58) Field of Classification Search
CPC .......................... C07K 14/70596; A61K 39/21
See application file for complete search history.

(56) References Cited

U.S. PATENT DOCUMENTS 11,116,833 B2 * 9/2021 Wu .................. C07K 14/70596
11,382,967 B2 * 7/2022 Wu .......................... C12N 7/00

OTHER PUBLICATIONS

Fu, Y., et al., Apr. 2020, PSGL-1 restricts HIV-1 infectivity by blocking virus particle attachment to target cells, PNAS 117(17):9537-9545.*
He, S., et al., 2021, PSGL-1 inhibits the incorporation of SARS-CoV and SARS-CoV-2 spike glycoproteins into pseudovirions and impairs pseudovirus attachment and infectivity, Viruses 13, 46, p. 1-8.*

* cited by examiner

*Primary Examiner* — Jeffrey S Parkin
(74) *Attorney, Agent, or Firm* — Raj S. Dave; Dave Law Group LLC

(57) ABSTRACT

Embodiments relate to a method comprising (a) expressing a vector comprising a PSGL-1 (P-selectin glycoprotein ligand-1) or a mutant thereof in a VPC (virus producing cell); and blocking a virus infection by inactivating an infectivity of a released virions from the VPC; or (b) expressing a glycoprotein or a mutant thereof in the VPC; blocking the virus infection by preventing binding of the released virions to a target cell; inactivating infectivity of the released virions; and targeting a viral infection. Other embodiments relate to (1) a broad-spectrum anti-viral product comprising: a vector expressing a glycoprotein or a mutant thereof in a VPC; and blocking a virus infection by inactivating infectivity of a released virion from the VPC; and (2) a vaccine comprising a viral particle is configured to a live attenuated or an inactivated or a non-infectious, wherein the viral particle are produced in a VPC.

20 Claims, 35 Drawing Sheets

Figure 1A:
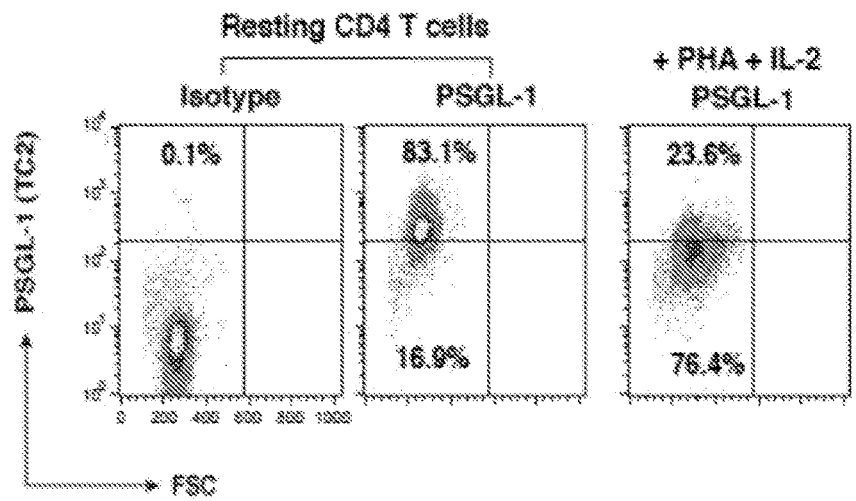

Specification includes a Sequence Listing.

Sequence 1 (PSGL-1)
Sequence 2 (PSGL-1-NT)
Sequence 3 (PSGL-1-CT)

Sequence 4 (PSGL-1(WT))
Sequence 5 (PSGL-1-3A)
Sequence 6 (PSGL-1-6A)
Sequence 7 (PSGL-1-C310A)
Sequence 8 (PSGL-1-ΔCT)

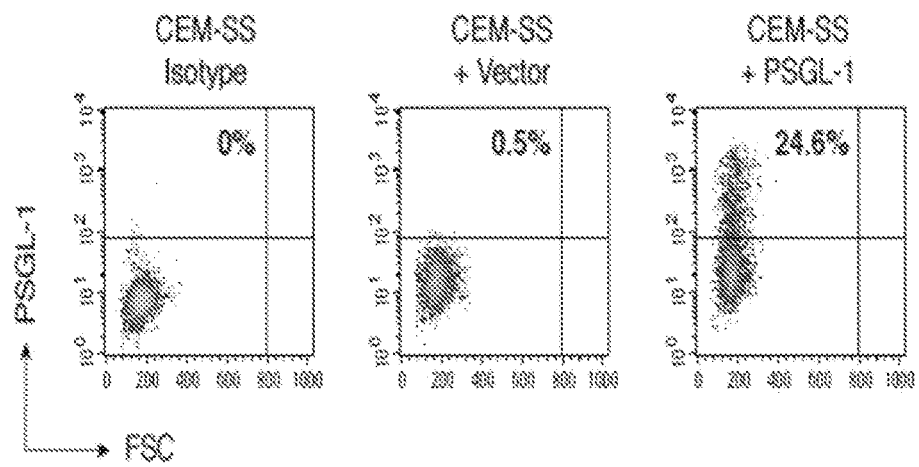
Fig. 13A
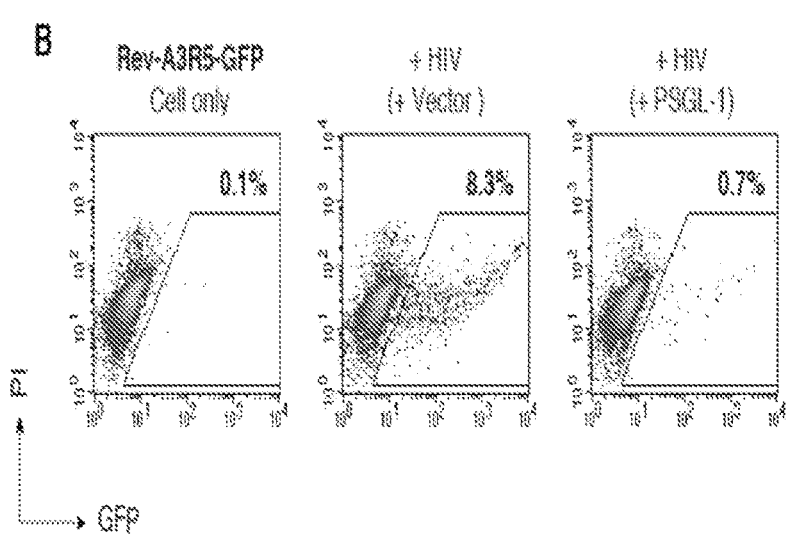
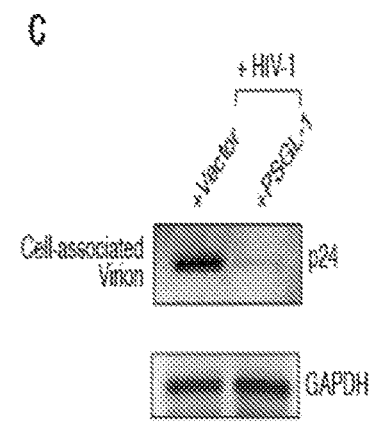
Fig. 13B
Fig. 13C

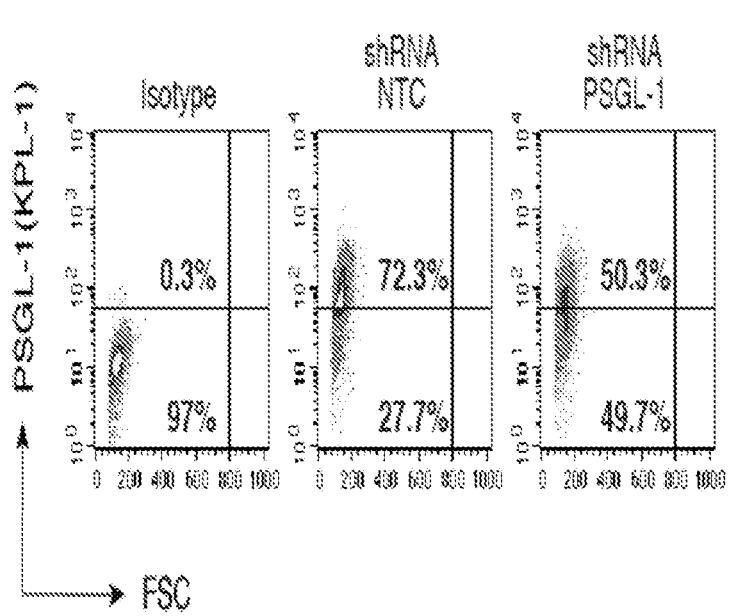 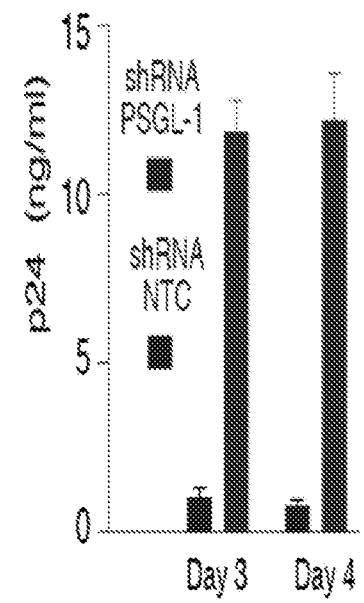
Fig. 14A Fig. 14B
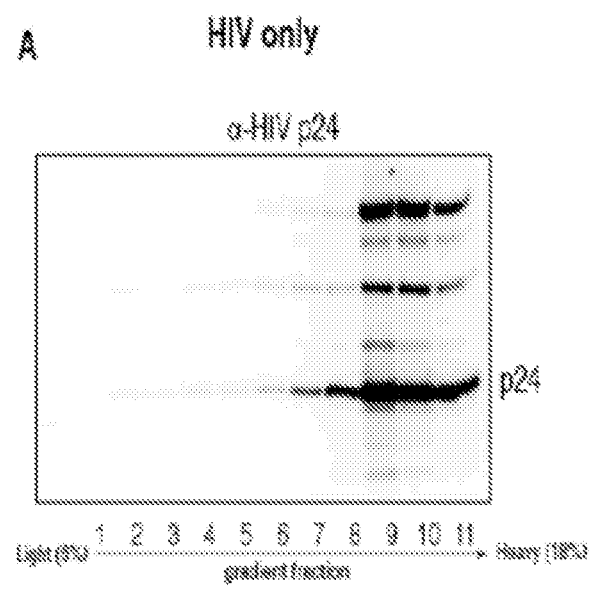
Fig. 15A

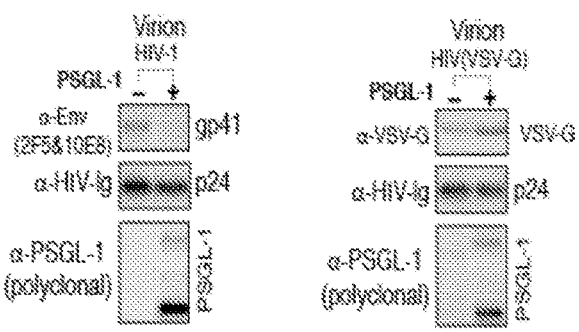
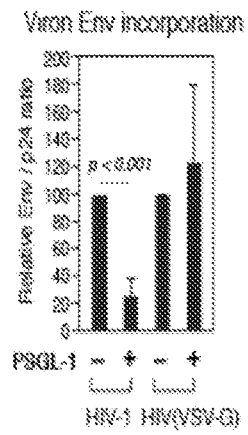
FIG. 16A
FIG. 16B
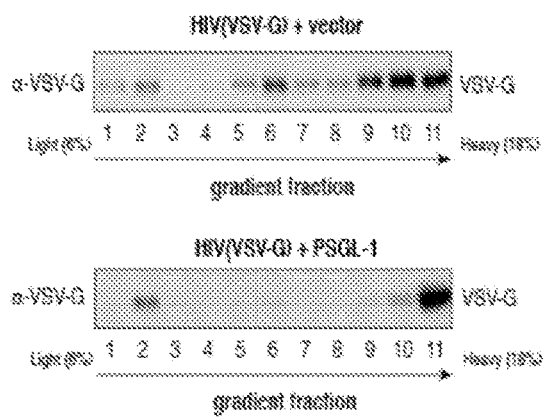
FIG. 16C
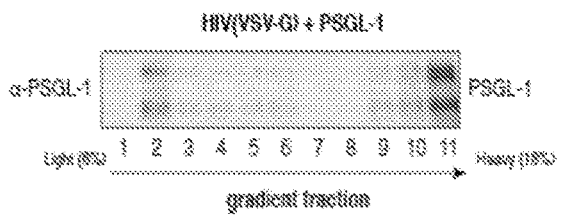
FIG. 16D
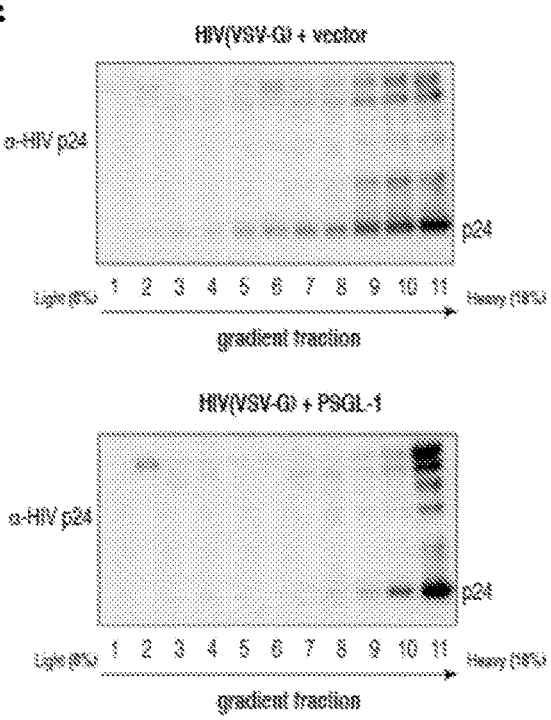
FIG. 16E

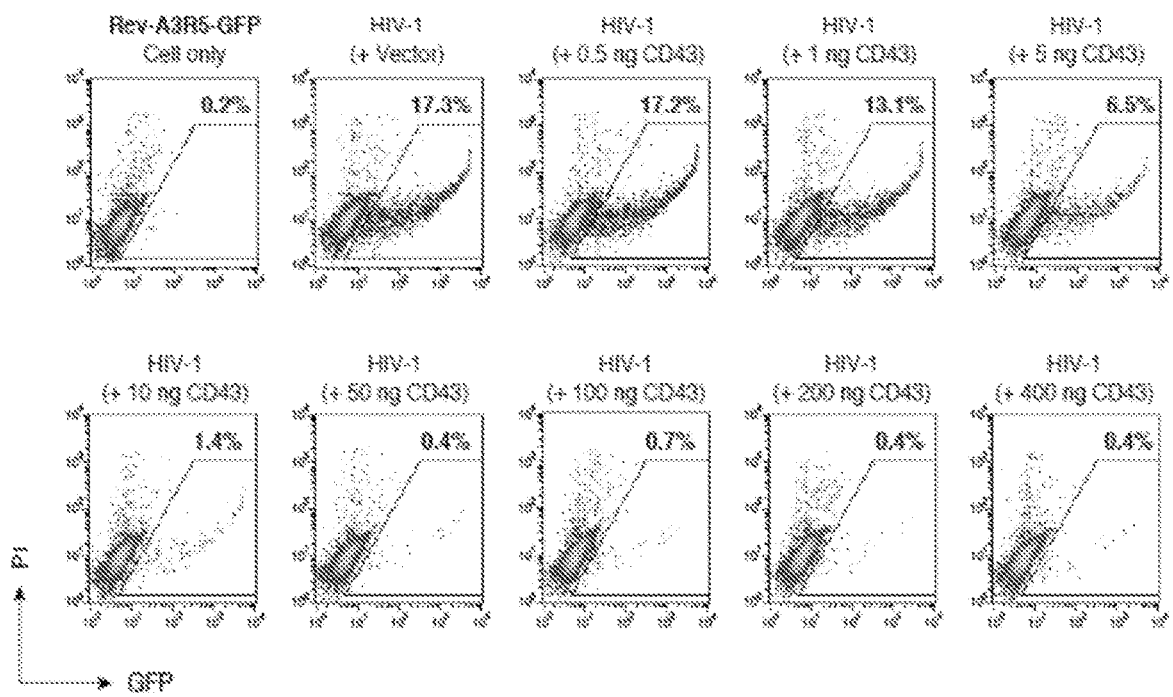
Fig. 19A
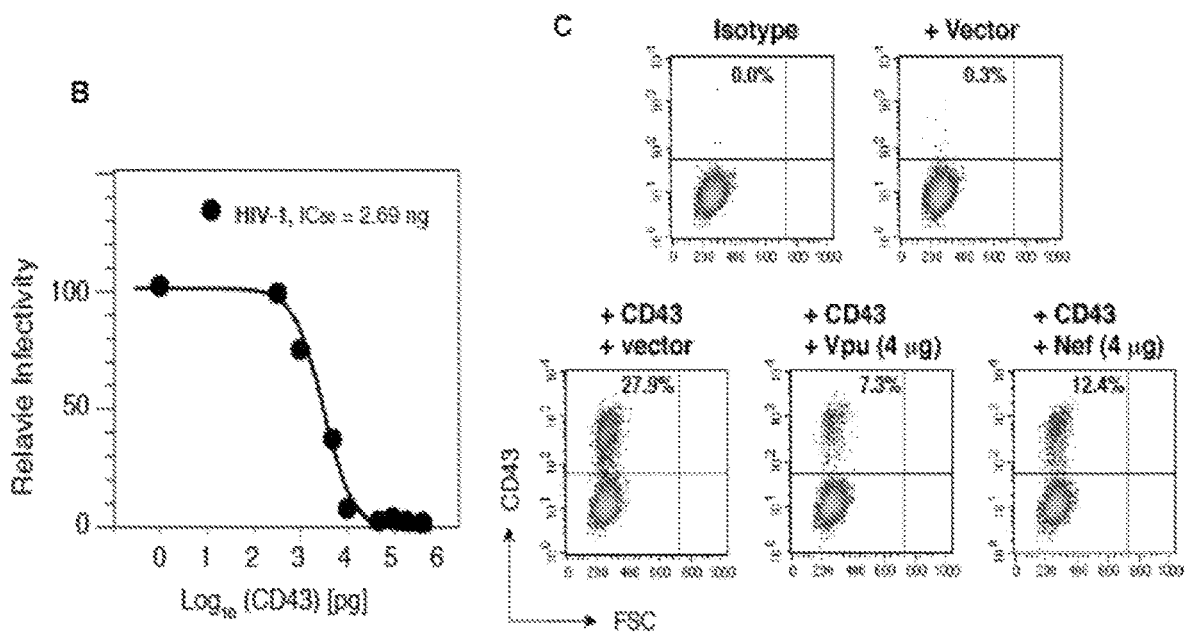
Fig. 19B
Fig. 19C

METHOD OF INHIBITING ENVELOPED VIRUS BINDING TO TARGET CELLS BY INCORPORATING P-SELECTIN GLYCOPROTEIN LIGAND-1 (PSGL-1) INTO VIRIONS

CROSS-REFERENCE TO RELATED APPLICATIONS

This application claims the benefit of and priority to U.S. Provisional Patent Application No. 62/828,381, entitled "THE USE OF PSGL-1 (P-SELECTIN GLYCOPROTEIN LIGAND-1) TO INACTIVATE ALL ENVELOPED VIRUSES FOR PRODUCING LIVE-ATTENUATED VACCINES." filed Apr. 2, 2019, the disclosure of which is hereby incorporated by reference herein in its entirety. This application is related to U.S. patent application Ser. No. 16/271,100, filed Feb. 8, 2019, entitled "METHOD AND SYSTEM FOR INACTIVATING VIRUS INFECTIVITY FOR PRODUCING LIVE-ATTENUATED VACCINES." which is incorporated herein in its entirety by reference.

DESCRIPTION OF THE TEXT FILE SUBMITTED ELECTRONICALLY

The contents of the computer readable text file with following details (filename: GMUN_003_01US_ST25.txt, date recorded: Oct. 7, 2022, file size 11.7 kilobytes) submitted electronically herewith are incorporated herein by reference in their entirety. The sequences enlisted in .txt file are identical to sequences present in FIG. 4B and FIG. 4C of the filed specification.

FIELD OF THE INVENTION

The Invention relates generally to method of blocking viral infectivity to target cells, more specifically to the method of inhibiting Human Immunodeficiency Viruses 1 (HIV-1) replication through expression of a P-selectin glycoprotein ligand-1 (PSGL-1).

BACKGROUND

Various references, including patents, patent applications, accession numbers, technical articles, and scholarly articles are cited throughout the specification. Each reference is incorporated by reference herein, in its entirety and for all purposes.

PSGL-1 (P-selectin glycoprotein ligand-1) also known as SELPLG or CD162, is a dimeric, mucin-like, 120-kDa glycoprotein that binds to P-, E-, and L-selectins (1-3). PSGL-1 is primarily expressed on the surface of lymphoid and myeloid cells (1, 4, 5), and is up-regulated during inflammation to mediate leukocyte tethering and rolling on the surface of endothelium to promote cell migration into inflamed tissues (6-9). PSGL-1 also serves as a surface receptor for enterovirus 71 (EV71) infection of leukocytes (10). In a mouse model of chronic viral infection, PSGL-1 has been reported to regulate T-cell checkpoints (11) and has been shown to be an IFN-γ regulated factor involved in Th1-mediated antiviral activity (8, 12). During T-cell differentiation, culturing T cells in the Th1 cytokine IFN-, and IL-12 promoted PSGL-1 expression preferentially in the IFN-γ producing T-cell population (8), suggesting that PSGL-1 could be an IFN-γ regulated factor involved in Th1-mediated antiviral activity.

PSGL-1 was reported to co-cluster with HIV-1 Gag at sites of assembly in the T-cell uropodin Gag-expressing cells (13). In addition, PSGL-1 was recently identified, through proteomic profiling of HIV-1-infected T cells, as an IFN-γ. induced restriction factor that blocks HIV-1 reverse transcription early post-entry and inactivates progeny virion infectivity during viral assembly (12). Emerging evidence has shown that the anti-HIV-1 activity of PSGL-1 was antagonized by the HIV-1 accessory protein Vpu (12). It is therefore not clear how HIV-1 overcomes PSGL-1 restriction at early time points during DNA synthesis. Furthermore, the mechanism of PSGL-1 inactivation of virion infectivity remains to be elucidated.

Furthermore, till date there has been no literature, elucidating the anti-viral effect of expressed PSGL-1 within a virus producing cells There is also dearth of broad-spectrum viral vaccine.

SUMMARY OF THE INVENTION

Embodiments relates generally to a method of expressing a PSGL-1 or a mutant thereof in a virus producing cell and blocking virus infection by inactivating infectivity of a released virion from the virus producing cell. PSGL-1 can inactivate viruses in cell culture conditions. It is found that during the production of murine leukemia virus (MLV) viruses, if PSGL-1 DNA was co-transfected with MLV DNA, PSGL-1, the virions released became non-infectious. These results suggest that PSGL-1 can be used to inactivate other viral particles.

In an embodiment, PSGL-1 is found to inactivate Human Immunodeficiency Viruses 1 (HIV-1).

In an embodiment, PSGL-1 is found to inactivate murine leukemia virus (MLV) viruses. It was found that during the production of murine leukemia virus (MLV) viruses, if PSGL-1 DNA was co-transfected with MLV DNA, PSGL-1, the virions released became non-infectious.

In an embodiment, PSGL-1 inactivate other viral particles.

An embodiment relates to the molecular details of PSGL-1 restriction of viral infection particularly HIV-1 infection.

In an embodiment, PSGL-1, a mucin-like glycoprotein expressed on blood CD4 T cells, restricts HIV-1 virion infectivity primarily by interfering with particle binding to target cells.

In an embodiment, PSGL-1 does not inhibit virion release.

In an embodiment, PSGL-1 is a potent inhibitor: it almost completely inactivates HIV-1 particle infectivity at a vector-to-proviral DNA ratio of 0.05:1.

An embodiment relates to a method for targeting a viral infection by expressing a selectin glycoprotein like PSGL-1 or a CD43 or a mutant thereof in a virus producing cell and blocking a virus infection by preventing binding of a released virion to a target cell and inactivating the infectivity of the released virion.

An embodiment relates to the method the PSGL or CD43 blocks the virus infection by structurally hindering binding of the released virion.

An embodiment relates to the molecular details of PSGL-1 restriction of viral infection particularly HIV-1 infection. Embodiments demonstrate that PSGL-1, a mucin-like glycoprotein expressed on blood CD4 T cells, restricts HIV-1 virion infectivity primarily by interfering with particle binding to target cells. PSGL-1 does not inhibit virion release. PSGL-1 is a remarkably potent inhibitor: it almost completely inactivates HIV-1 particle infectivity at a vector-to-proviral DNA ratio of 0.05:1.

An embodiment relates PSGL-1 is surface glycoproteins inhibits HIV spreading infection. PSGL-1 blocks the binding of virus particles to target cells. Another embodiment relates CD43 is surface glycoproteins inhibits HIV spreading infection. CD43 blocks the binding of virus particles to target cells.

An embodiment relates to a method for targeting a viral infection by expressing a selectin glycoprotein like PSGL-1 or CD43 or a mutant thereof in a virus producing cell and blocking a virus infection by preventing binding of a released virion to a target cell and inactivating the infectivity of the released virion. In the method the PSGL or CD43 blocks the virus infection by structurally hindering binding of the released virion.

An embodiment relates to a broad-spectrum anti-viral product comprising: a vector expressing a selectin glycoprotein like PSGL-1 or CD43 or a mutant thereof in a virus producing cell; and blocking a virus infection by inactivating infectivity of a released virion from the virus producing cell.

An embodiment relates to a vaccine comprising live attenuated, inactivated, or non-infectious virus particles, wherein the virus particles are produced in virus producing cells, and wherein a selectin glycoprotein like PSGL-1 or CD43 or a mutant thereof is expressed in the virus producing cells.

An embodiment relates to a method comprising expressing a vector comprising a PSGL-1 (P-selectin glycoprotein ligand-1) or a mutant thereof in a VPC (virus producing cell); and blocking a virus infection by inactivating an infectivity of a released virions from the VPC.

In an embodiment, the PSGL-1 comprises an extracellular N-terminal domain that is configured to block the virus infection.

In an embodiment, the extracellular N-terminal domain of PSGL-1 comprises a decameric repeat: wherein the decameric repeat is configured to block the virus infection.

In an embodiment, the PSGL-1 is configured to block the infectivity of the released virions by blocking a binding of the released virions to a target cell.

In an embodiment, the PSGL-1 is configured to block the infectivity through a structural hindrance of the released virions binding to a target cell.

In an embodiment, the PSGL-1 is expressed by an expression vector into the VPC; inactivating infectivity of the released virions are independent of an envelope glycoprotein of the VPC; the VPC comprises a host cell infected with a virus; the virus infection comprises a human immunodeficiency virus HIV, a murine leukemia virus, an influenza virus or similar thereof.

Another embodiment relates to a method comprising: expressing a glycoprotein or a mutant thereof in a VPC (virus producing cell); blocking a virus infection by preventing binding of a released virions to a target cells; inactivating infectivity of the released virions; and targeting a viral infection.

In other embodiments: the glycoprotein comprises a PSGL-1 (P-selectin glycoprotein ligand-1), a CD43, a mutant of the PSGL-1 or a mutant of the CD43; the glycoprotein is configured to block infectivity of the released virions by preventing the binding of the released virions to the target cells: the glycoprotein or the mutant therefor is expressed by an expression vector into the VPC; the glycoprotein is configured to block the virus infection by structurally hindering binding of the released virions; the VPC comprises a host cell infected with a virus; the virus comprises a human immunodeficiency virus (HIV), a murine leukemia virus, an influenza virus or similar thereof.

Another embodiment relates to a broad-spectrum anti-viral product comprising: a vector expressing a glycoprotein or a mutant thereof in a VPC (virus producing cell); and blocking a virus infection by inactivating infectivity of a released virion from the VPC.

In other embodiments the glycoprotein comprises a PSGL-1 (P-selectin glycoprotein ligand-1), a CD43, a mutant of the PSGL-1 or a mutant of the CD43; about 1 μg of the PSGL-1 produces about 100 fold decrease in anti-viral activity of the released virion from the VPC; about 3 μg of the PSGL-1 produces about 8000 fold decrease in anti-viral activity of the released virion from the VPC. A CD43 expression vector is configured to block the virus infection: about 0.5 to 400 ng of a CD43 expression vector is configured inactivate infectivity of a released virion from the VPC; the VPC comprises a host cell infected with a virus. In an embodiment the virus infection comprises a human immunodeficiency virus (HIV), a murine leukemia virus (MLV), an influenza virus or similar thereof.

Another embodiment relates to a vaccine comprising, a viral particle is configured to a live attenuated or an inactivated or a non-infectious, wherein the viral particle are produced in a VPC, and wherein the VPC comprises a vector expressing a glycoprotein or a mutant thereof. In other embodiments: the glycoprotein comprises a PSGL-1 (P-selectin glycoprotein ligand-1) or a CD43 or a mutant thereof; the VPC are a host cell infected with a virus; the viral particle comprises a human immunodeficiency virus (HIV), a murine leukemia virus (MLV), an influenza virus or similar thereof.

Another embodiment relates to a use of a glycoprotein or a mutant thereof in a therapeutic treatment of a virus infection, wherein, a vector expressing the glycoprotein or a mutant thereof in a VPC (virus producing cell); and blocking a virus infection by inactivating infectivity of a released virion from the VPC, wherein the glycoprotein comprises a PSGL-1 (P-selectin glycoprotein ligand-1), a CD43, a mutant of the PSGL-1 or a mutant of the CD43.

An embodiment relates a finding that PSGL-1 can inactivate both HIV and other viruses e.g. MLV (murine leukemia virus), suggesting that PSGL-1 can inactivate a large number of viruses. PSGL-1 could be used in the preparation of a non-infectious virion particles by the expressing or overexpressing PSGL-1, in virus producing cells to inactivate viral infectivity. Such virions particles could be used as a vaccine to treat or prevent disease related to HIV infection or other viruses infection. Also, the application also elucidated the mechanism of PSGL-1 inactivation of virion infectivity.

An embodiment relates to a selectin glycoprotein like PSGL-1 can inactivate both HIV and other viruses such as MLV (murine leukemia virus, influenza A virus), suggesting that PSGL-1 can inactivate a large number of viruses. The use of overexpression of PSGL-1 in viral producing cells to inactivate viral infectivity. The released non-infectious virion particles can be used as a viral vaccine.

BRIEF DESCRIPTION OF THE DRAWINGS

FIGS. 1A-1F: shows PSGL-1 is expressed on human CD4 T cells and exerts an anti-HIV activity.

FIG. 1A: Peripheral blood resting CD4 T cells were purified by negative selection, activated with PHA+IL-2 or left unstimulated. Cell-surface PSGL-1 expression was analyzed by flow cytometry.

Figure 1B:
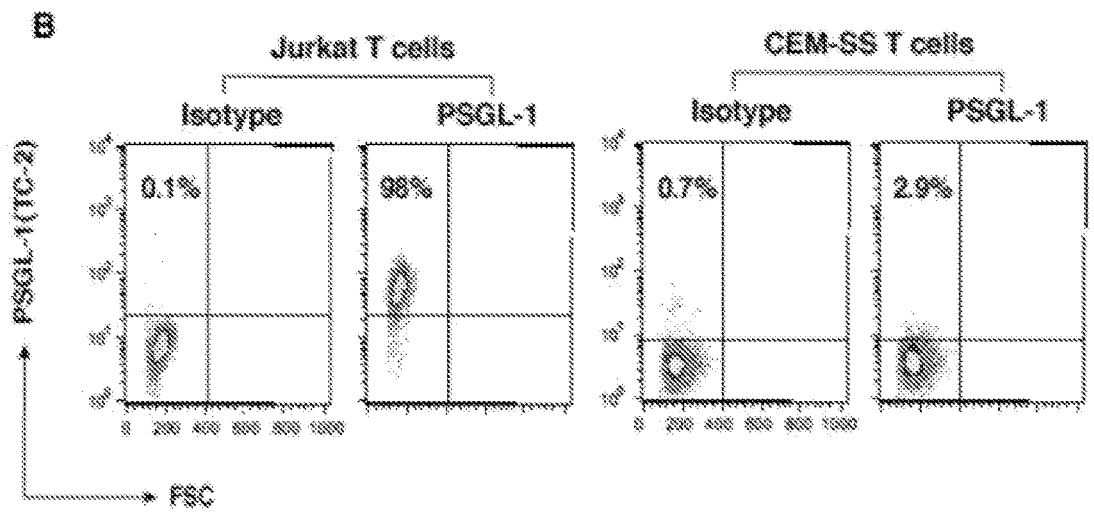

FIG. 1B: Jurkat and CEM-SS cells were similarly stained for surface PSGL-1.

Figure 1C:
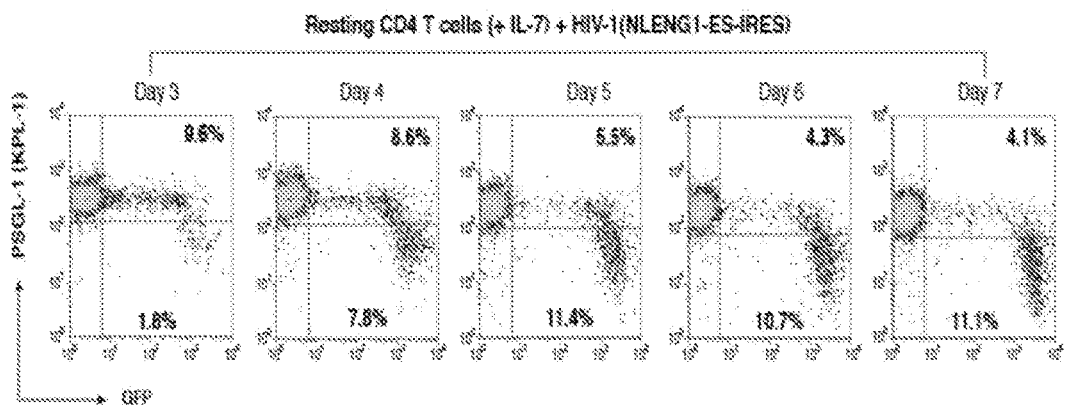
Figure 1D:
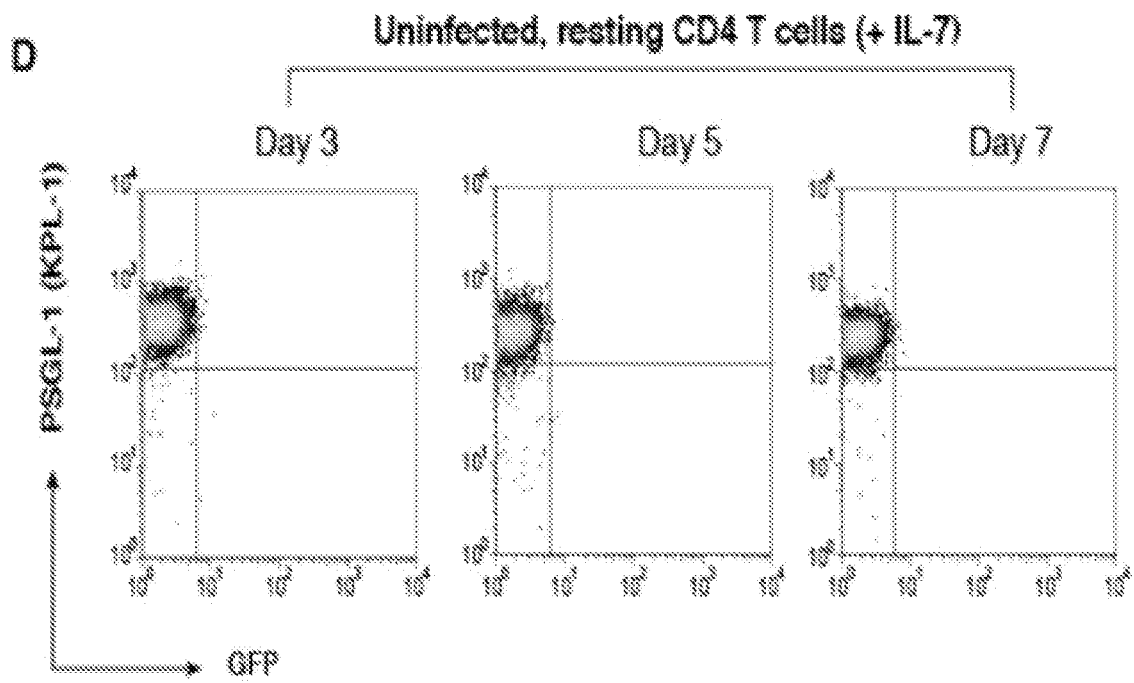
Figure 1E:
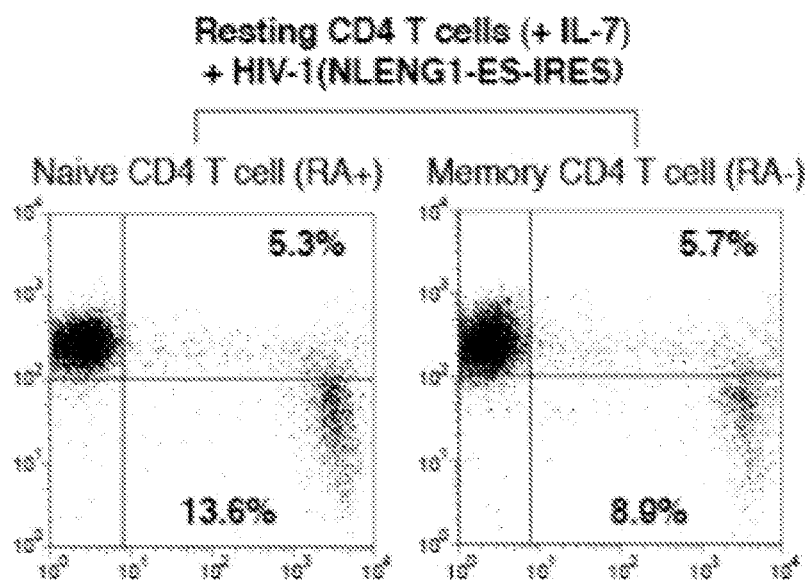

FIG. 1C: to FIG. 1E) Downregulation of PSGL-1 by HIV-1 in primary CD4 T cells. Primary resting CD4 T cells were infected with NLENG1-ES-IRES, a GFP reporter virus. Following infection, cells were washed and cultured in complete medium plus IL-7 (2 ng/ml) to permit low-level viral replication. Surface PSGL-1 expression was analyzed at the indicated days.

FIG. 1C: Shown are the percentages of the GFP+ or GFP− cells with low or high PSGL-1 staining in each panel. PSGL-1 downregulation was observed only in the HIV-infected (GFP+) cell population.

FIG. 1D: For controls, uninfected cells were similarly cultured in IL-7 and surface PSGL-1 expression was analyzed at the indicated days. Culturing resting CD4 T cells in IL-7 did not lead to PSGL-1 downregulation.

FIG. 1E: Cells were also stained for surface PSGL-1 expression on the CD45RA+ (naïve) and CD45RA− (memory) CD4 T cells on day 7, and analyzed by flow cytometry.

Figure 1F:
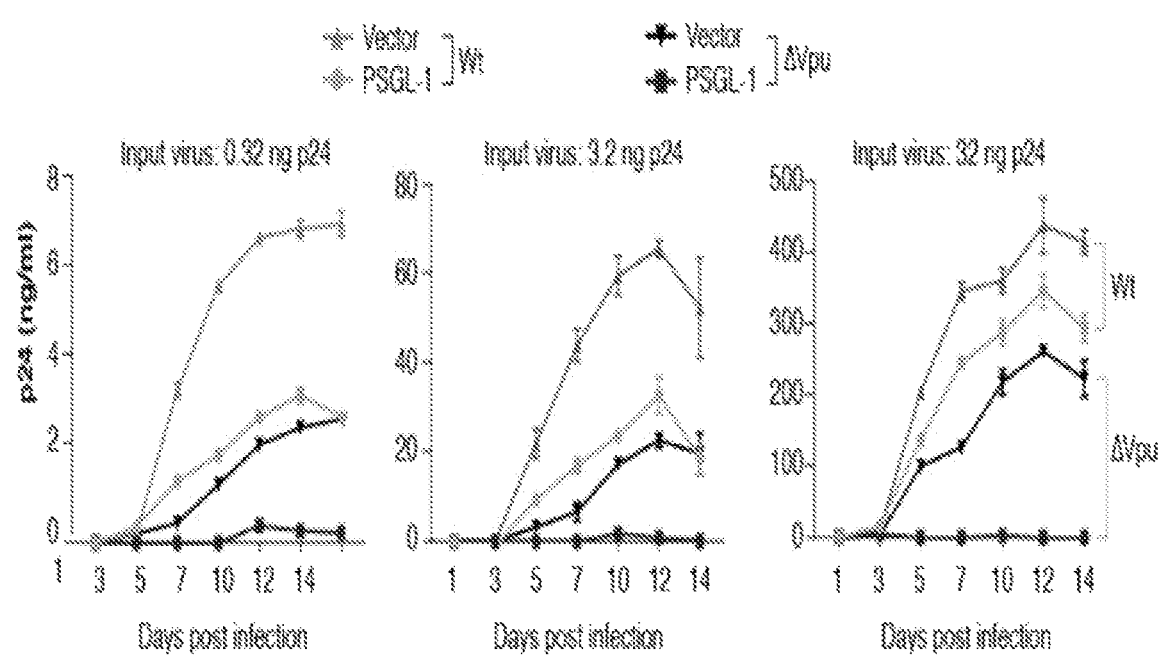

FIG. 1F: HeLa JC.53 cells were stably transfected with PSGL-1 or empty vector DNA and drug-selected to obtain stably transfected cells. Cells were then infected with 3 different inputs of HIV-1(NL4-3) WT or HIV-1(ΔVpu). Viral replication was quantified by p24 release.

FIGS. 2A-2K: shows PSGL-1 does not block viral release but inactivates virion infectivity.

Figure 2A:
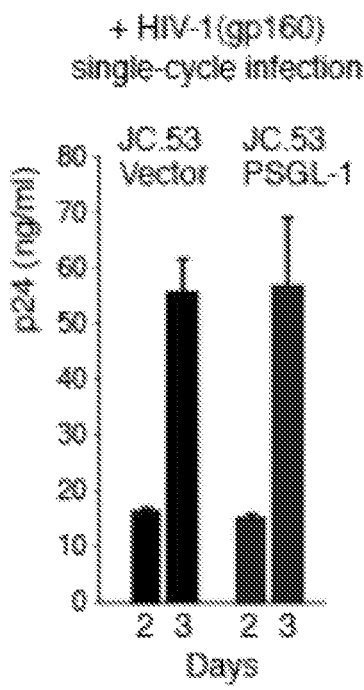

FIG. 2A: HeLa JC.53 cells were stably transfected with PSGL-1 or empty vector DNA and drug-selected to obtain stably PSGL-1-expressing cells. Cells were then infected with the single-round vector HIV-1 (gp160) for single-round infection. Viral replication was quantified by p24 release.

Figure 2B:
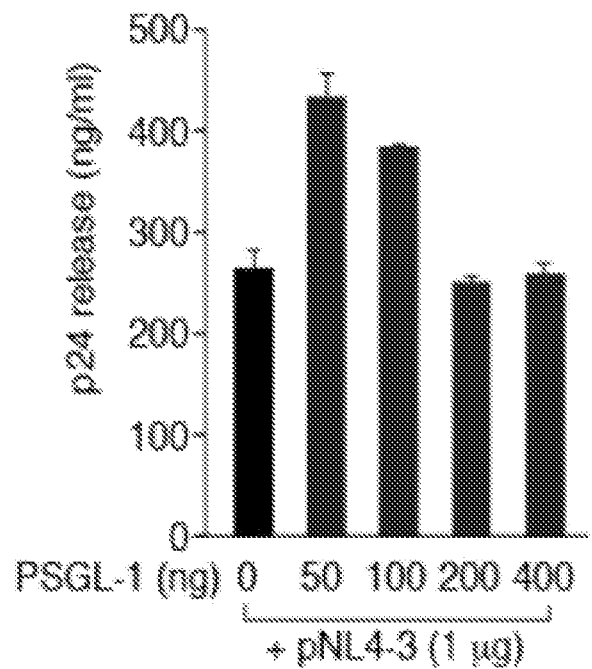

FIG. 2B: HEK293T cells were cotransfected with HIV (NL4-3) DNA (1 μg) plus different amounts of PSGL-1 expression vector. Viral p24 release was quantified at 48 hours.

Figure 2C:
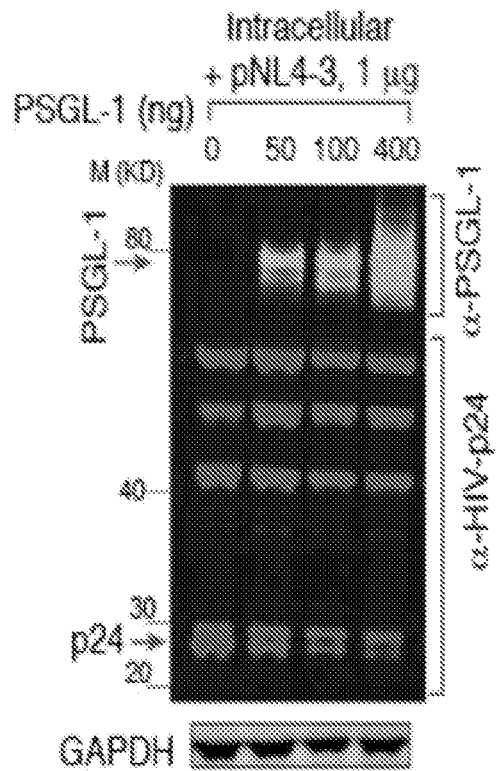

FIG. 2C: Cells were also lysed and analyzed by western blot for intracellular PSGL-1 and HIV-1 proteins.

Figure 2D:
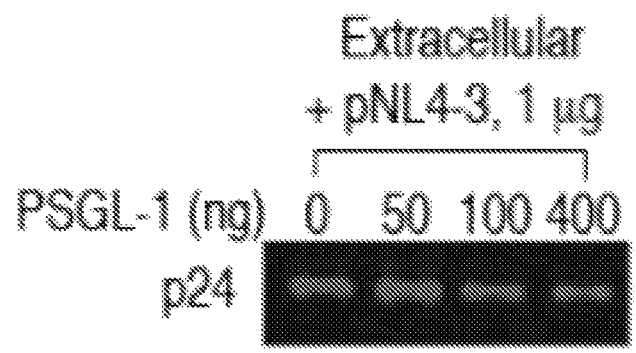

FIG. 2D: Extracellular virion p24 was also analyzed by western blot

Figure 2E:
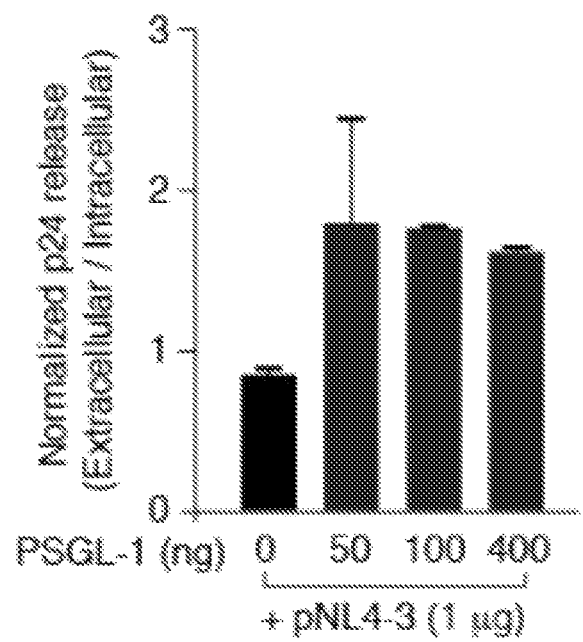
Figure 2F:
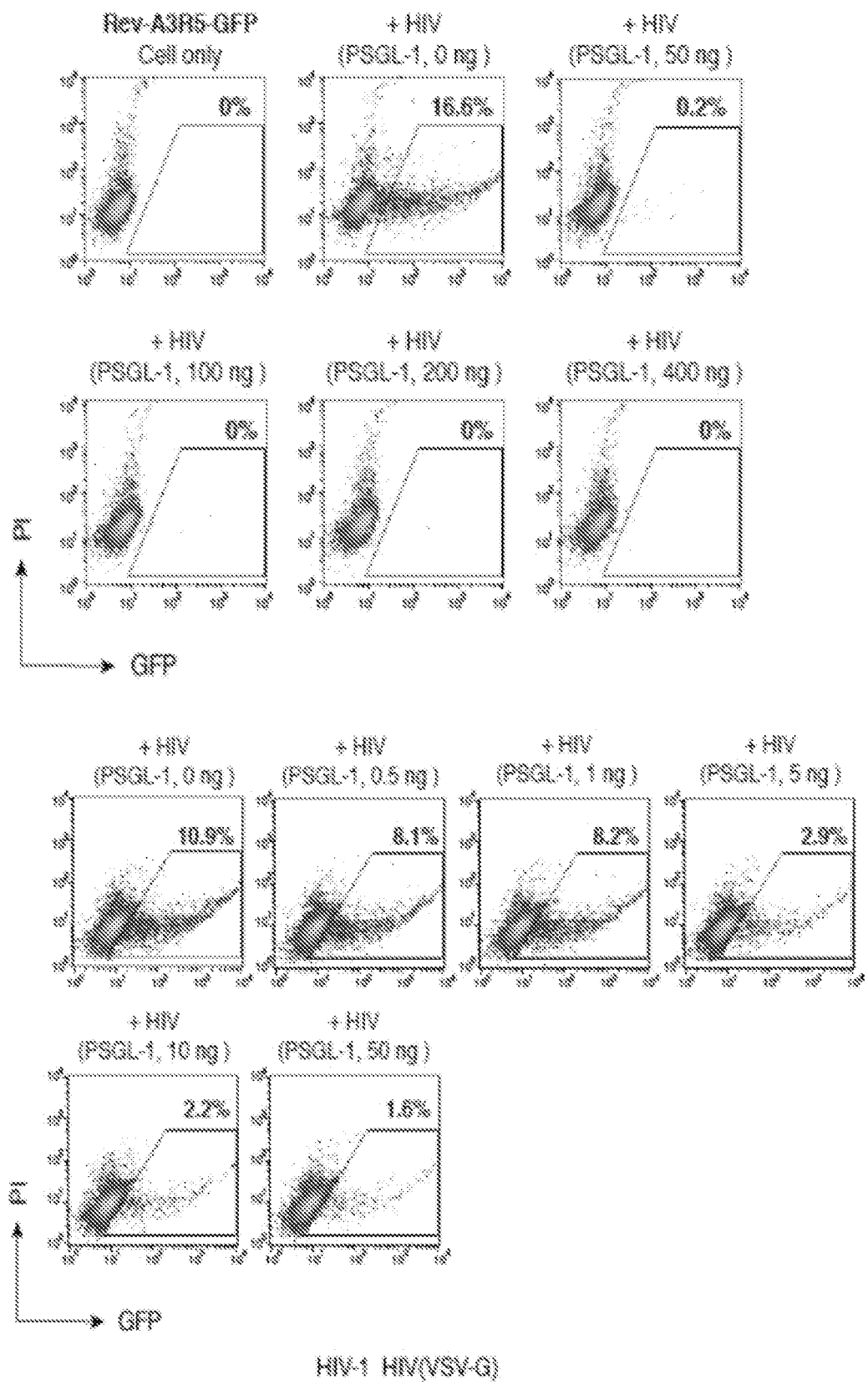

FIG. 2E: shows the relative ratio of extracellular and intracellular p24 was plotted, FIG. 2F: Virions released from HEK293T cells cotransfected with HIV(NL4-3) DNA (1 μg) plus PSGL-1 DNA (0.5 to 400 ng) were harvested at 48 hours and normalized for p24, and viral infectivity was quantified by infecting the T-cell line-derived Rev-A3R5-GFP indicator cell line. HIV-1 replication was quantified by GFP expression. Shown are the percentages of GFP+ cells at 48 hours postinfection.

Figure 2G:
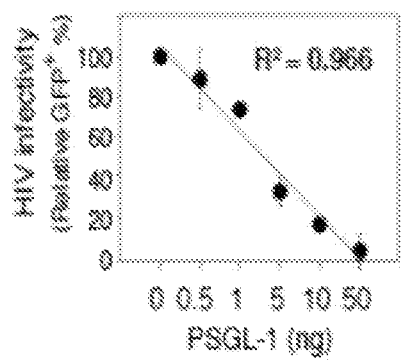

FIG. 2G: The PSGL-1 dose-dependent inhibition curve was plotted using results from 3 independent experiments.

Figure 2H:
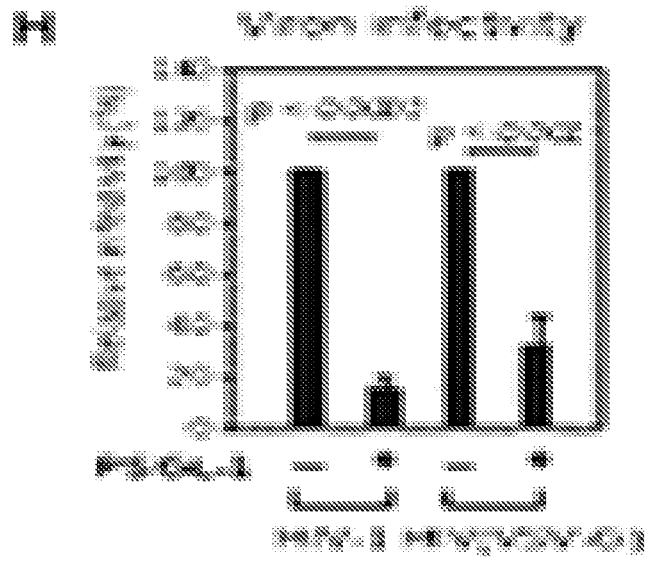

FIG. 2H: PSGL-1 blocks the infectivity of VSV-G-pseudotyped HIV-1. Virus particles produced in the presence of PSGL-1 or the empty vector were assayed for infectivity using TZM-bl cells.

Figure 2I:
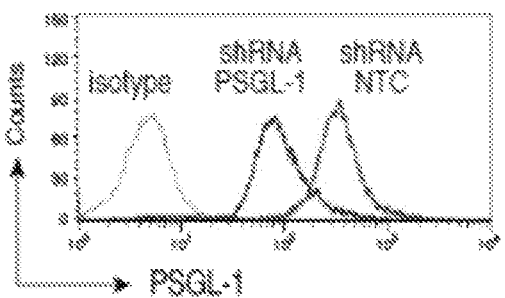
Figure 2J:
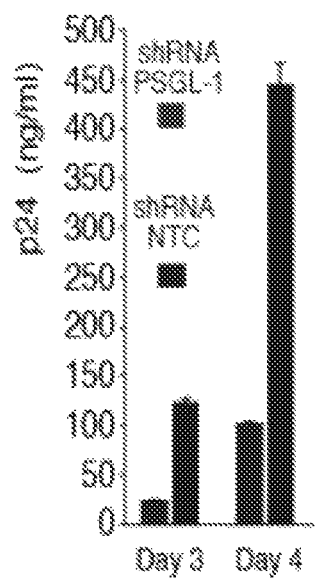
Figure 2K:
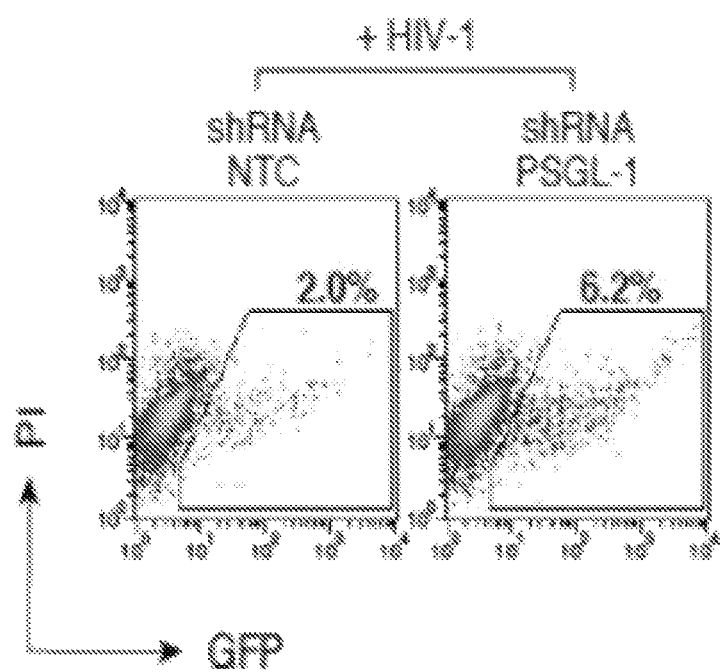

FIG. 2I to FIG. 2K: shRNA knockdown of PSGL-1 enhances virion infectivity. Jurkat cells were transduced with a lentiviral vector expressing shRNA against PSGL-1 (shRNA PSGL-1) or a non-target sequence (shRNA NTC).

FIG. 2I: PSGL-1 surface expression was quantified at 12 days post-transduction and puromycin selection.

FIG. 2J: Cells were also electroporated with HIV-1(NL4-3) DNA, and viral replication in knockdown Jurkat cells was quantified by measuring p24 in the supernatant.

FIG. 2K: To quantify HIV infectivity, virions were harvested at 48 hours post-electroporation, and used to infect Rev-A3R5-GFP cells, using an equal amount of p24 for infection.

Figure 3A:
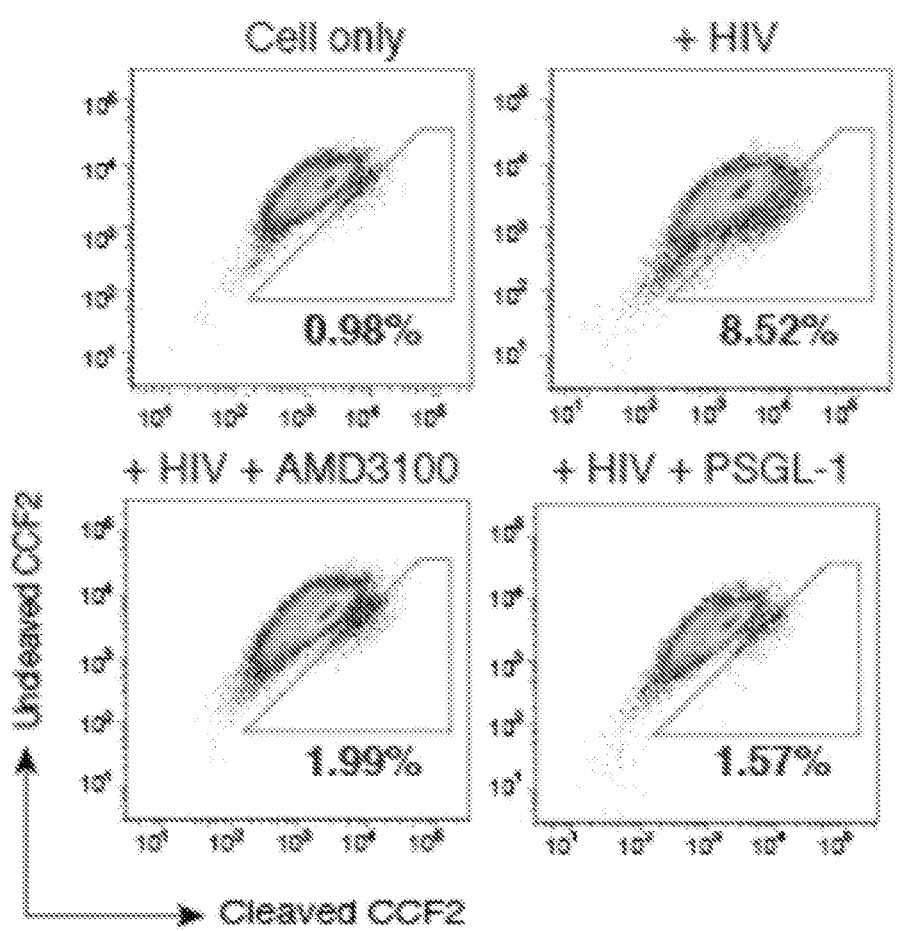
Figure 3B:
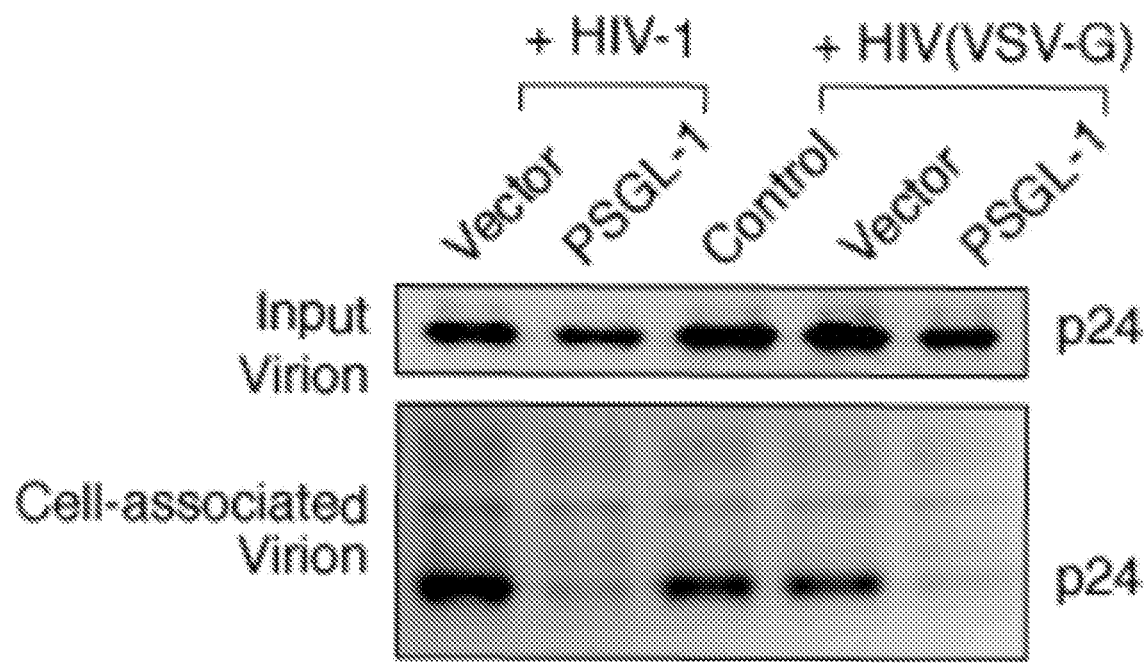
Figure 3C:
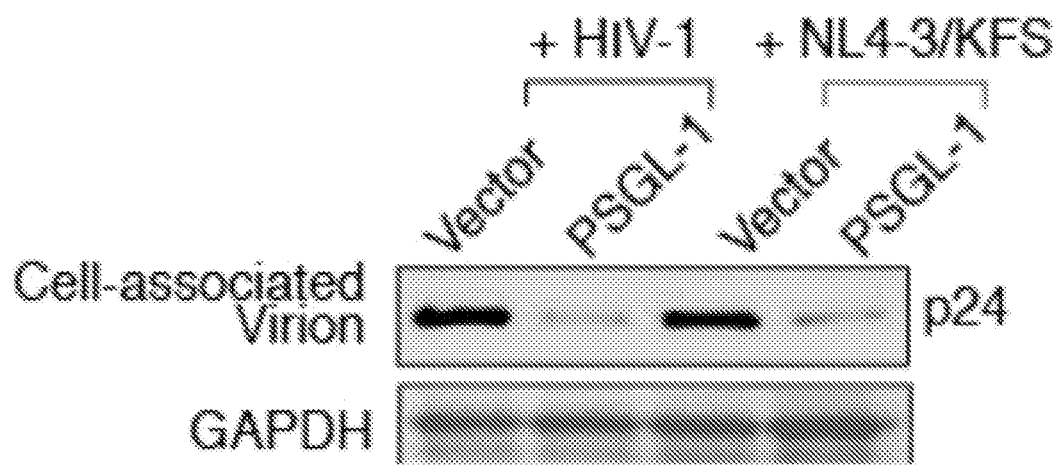

FIGS. 3A-3C: shows PSGL-1 blocks virion attachment to target cells.

FIG. 3A: Virions produced from HEK293T cells co-transfected with PSGL-1 expression vector plus HIV-1 (NL4-3) were used for an entry assay. As controls. HIV-1 virions similarly produced in the presence of an empty vector were used. Equal p24 was used for the assay. The entry inhibitor AMD3100 was also used as a control to block virus entry. The percentages of cells with cleaved CCF2 are shown.

FIG. 3B: Virions produced in the presence of PSGL-1 or the empty vector were assayed for attachment to target HeLa JC.53 cells at 4° C., for 2 hours. Cells were washed and then analyzed by western blot for bound p24.

FIG. 3C: PSGL-1 blocks Env(−) HIV-1 particle attachment to target cells. WT HIV-1 or Env(−) HIV-1 [(NL4-3)/KFS] virions were produced in the presence of PSGL-1 or the empty vector. Viral particles were assayed for attachment to target HeLa JC.53 cells.

FIGS. 4A-4D: shows the extracellular. N-terminal domain of PSGL-1 is required to block HIV-1 infectivity.

Figure 4A:
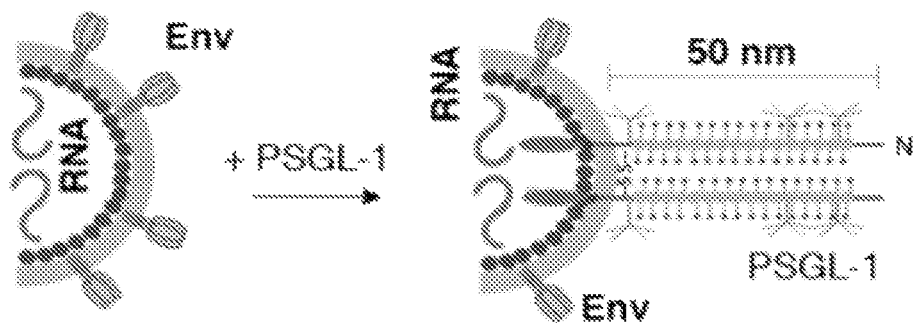

FIG. 4A: Hypothetical model by which virion incorporation of PSGL-1 restricts virion infectivity. Based on this model, the incorporation of the heavily glycosylated and elongated PSGL-1 on viral particles may interfere with virion binding to target cells.

Figure 4B:
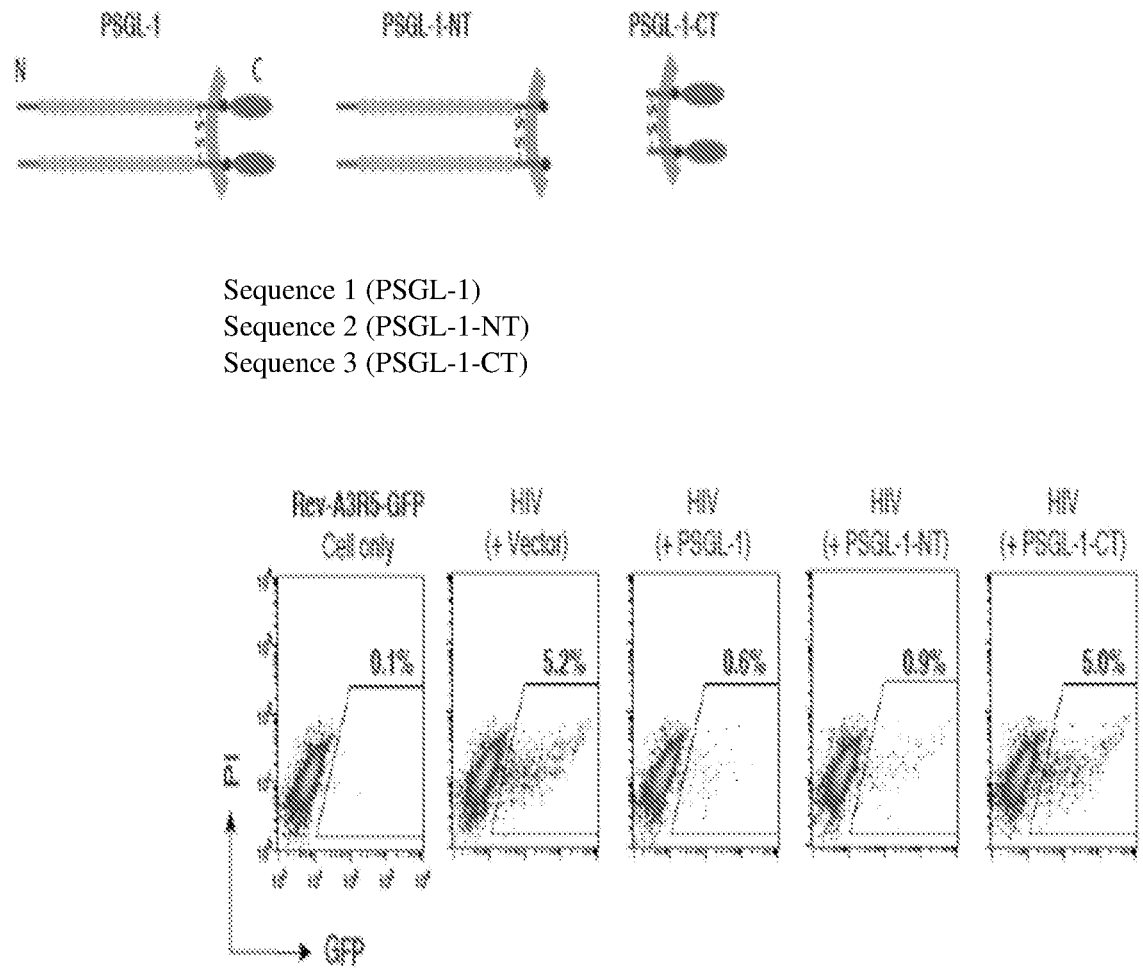

FIG. 4B: PSGL-1 domains involved in blocking HIV-1 infectivity. HEK293T cells were co-transfected with HIV (NL4-3) DNA (1 μg) plus vectors expressing PSGL-1 (Sequence 1, wherein MPLQ . . . PDHISVKQC is EC region, LLAILILALVATIFFVCTVV is TM region and LAVRLSRKGHMYPV . . . LHSFLP is CT region) or PSGL-1 truncation mutants. PSGL-1-NT (Sequence 2, wherein MPLQ . . . PDHISVKQC is EC region, LLAILILALVATIFFVCTVV is TM region and LAVRLSRKGH is CT region) or PSGL-1-CT (500 ng) (Sequence 3, wherein PDHISVKQC is EC region. LLAILILALVATIFFVCTVV is TM region and LAVRLSRKGHMYPV . . . LHSFLP is EC region). Virions were harvested at 48 hours post-transfection and normalized for p24, and viral infectivity was quantified by infecting Rev-A3R5-GFP indicator cells. HIV-1 35 replication was quantified by GFP expression.

Figure 4C:
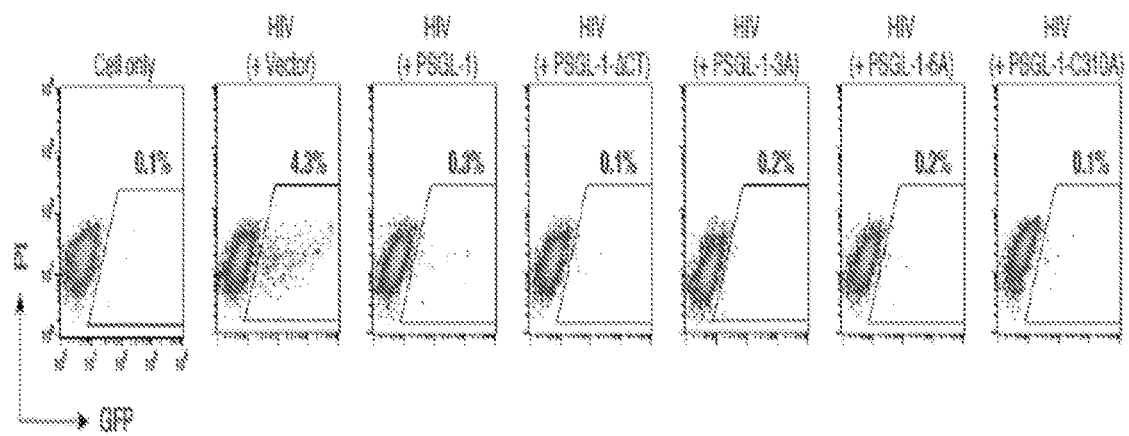

FIG. 4C: PSGL-1 intracellular domain mutants. PSGL-1-ACT (Sequence 8). PSGL-1-3A (Sequence 5, wherein KQC is EC region, LLAILILALVATIFFVCTVV is TM region and LAVALSAAGHMYPV . . . KSPGLTPEPREDREGDDLTLHSFLP is CT region). PSGL-1-6A (Sequence 6, wherein . . . KQC is EC region, LLAILILALVATIFFVCTVV is TM region and LAVRLSRKGHMYPV . . . KSPGLTPAPRAARAGAALTLHSFLP is CT region), and the dimerization mutant, PSGL-1-C310A (Sequence 7, wherein KQA is EC region LLAILILALVATIFFVCTVV is TM region and LAVRLSRKGHMYPV . . . KSPGLTPEPREDREGDDLTLHSFLP is CT region), were similarly tested. EC, extracellular domain; TM, transmembrane domain; CT, cytoplasmic tail.

Figure 4D:
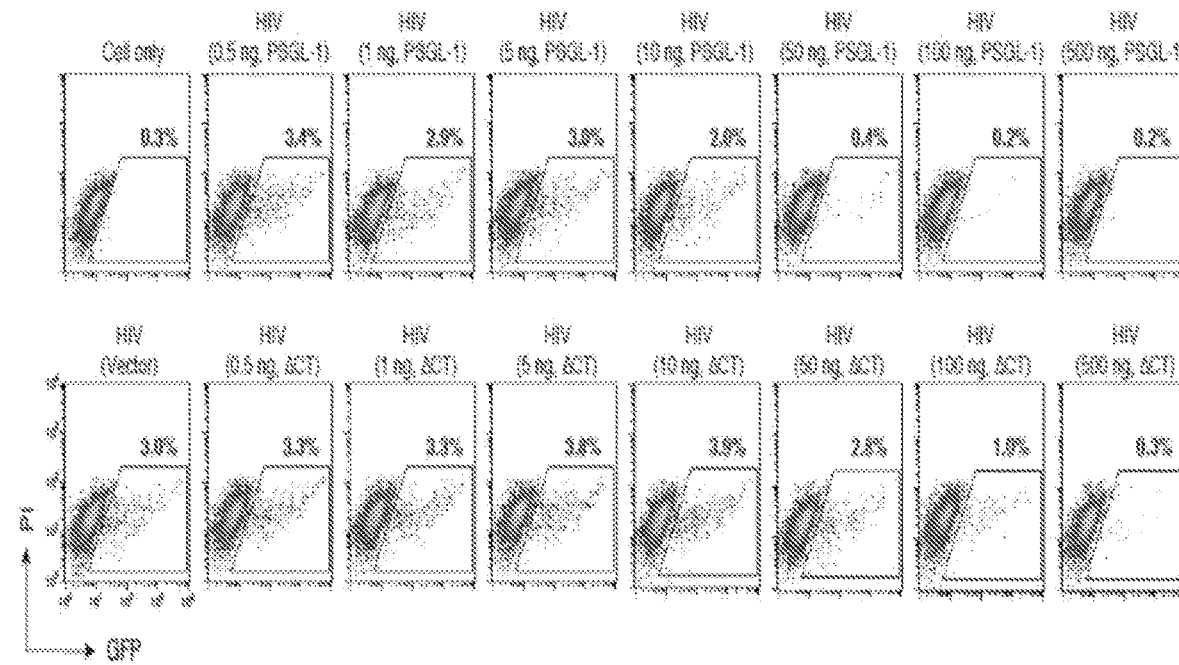

FIG. 4D: The PSGL-1-ACT (Sequence 8, wherein KQC is EC region and LLAILILALVATIFFVCTVV is TM region) mutant displays reduced antiviral activity relative to WT PSGL-1 (Sequence 4, wherein KQC is EC region, LLAILILALVATIFFVCTVV is TM region and LAVRLSRKGHMYPV . . . KSPGLTPEPREDREGD-DLTLHSFLP is CT region). HEK293T cells were co-transfected with HIV(NL4-3) DNA (1 µg) plus various amounts of PSGL-1 or PSGL-1-ΔCT (0.5-500 ng). Virions were harvested at 48 hours, normalized for p24, and their infectivity was measured in Rev-A3R5-GFP indicator cells.

Figure 5A:
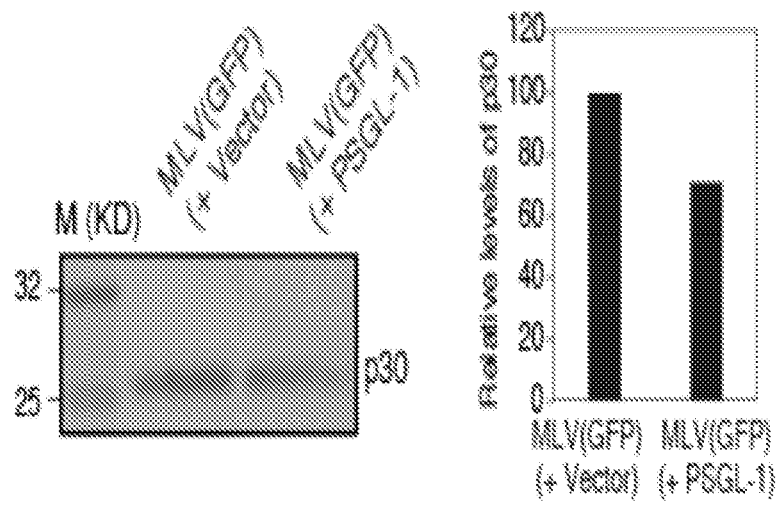
Figure 5B:
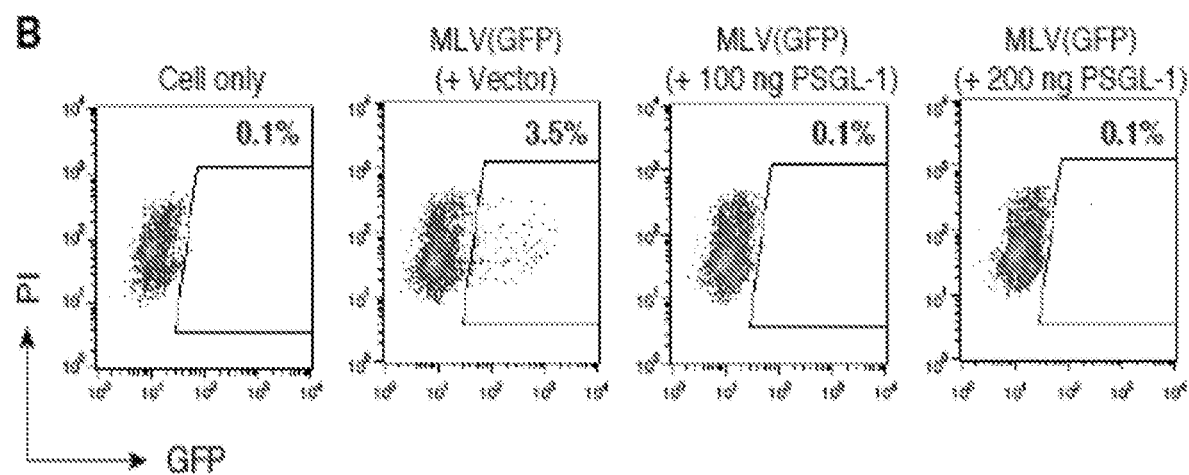
Figure 5C:
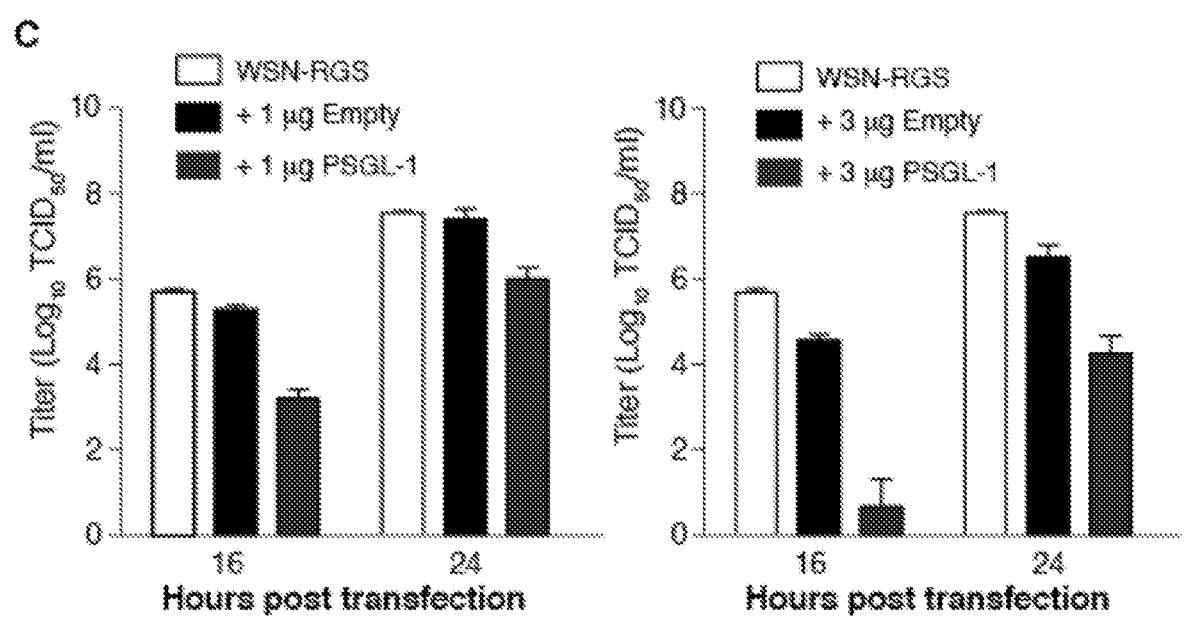

FIGS. 5A-5C: shows PSGL-1 restricts MLV and influenza A virus infectivity.

FIG. 5A: HEK293T cells were cotransfected with an MLV helper vector, pSV-ψ-MLV-env-, pRetroQ-AcGFP-N1, pHCMV-G plus a PSGL-1 expression vector or an empty control vector. Virions were harvested and quantified by western blot using an anti-MLV p30 (CA) protein antibody.

FIG. 5B: MLV virions were harvested, and viral infectivity was quantified by infecting HEK293T cells and measuring GFP expression.

FIG. 5C: Eight vectors expressing each of the segments of the influenza A/WSN/33 (H1N1) genome were cotransfected with a PSGL-1 expression vector into HEK293T-MDCK cells. Viral particles were harvested at 16 and 24 hours post-cotransfection, and virion infectivity was quantified by TCID50 assay.

Figure 6A:
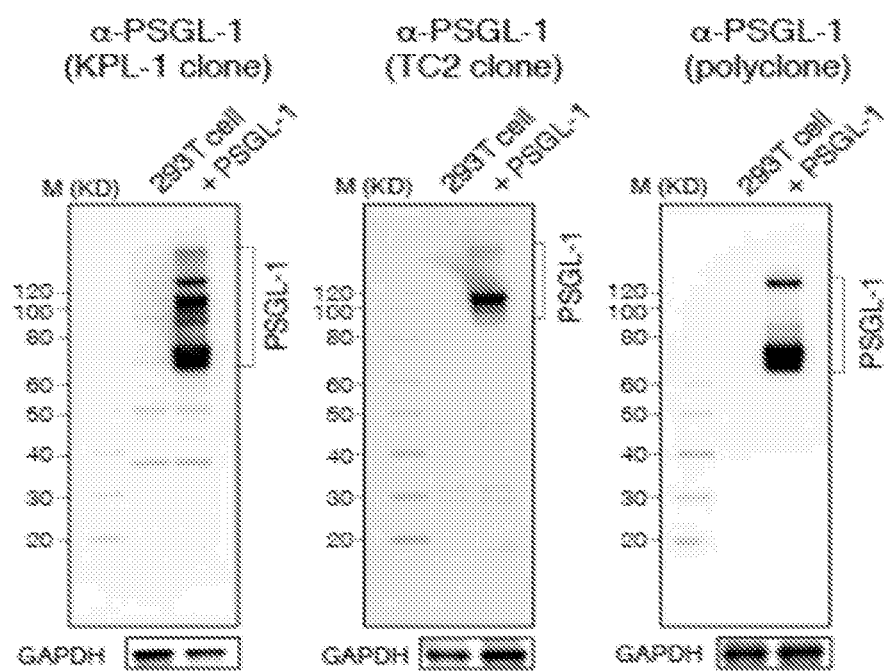
Figure 6B:
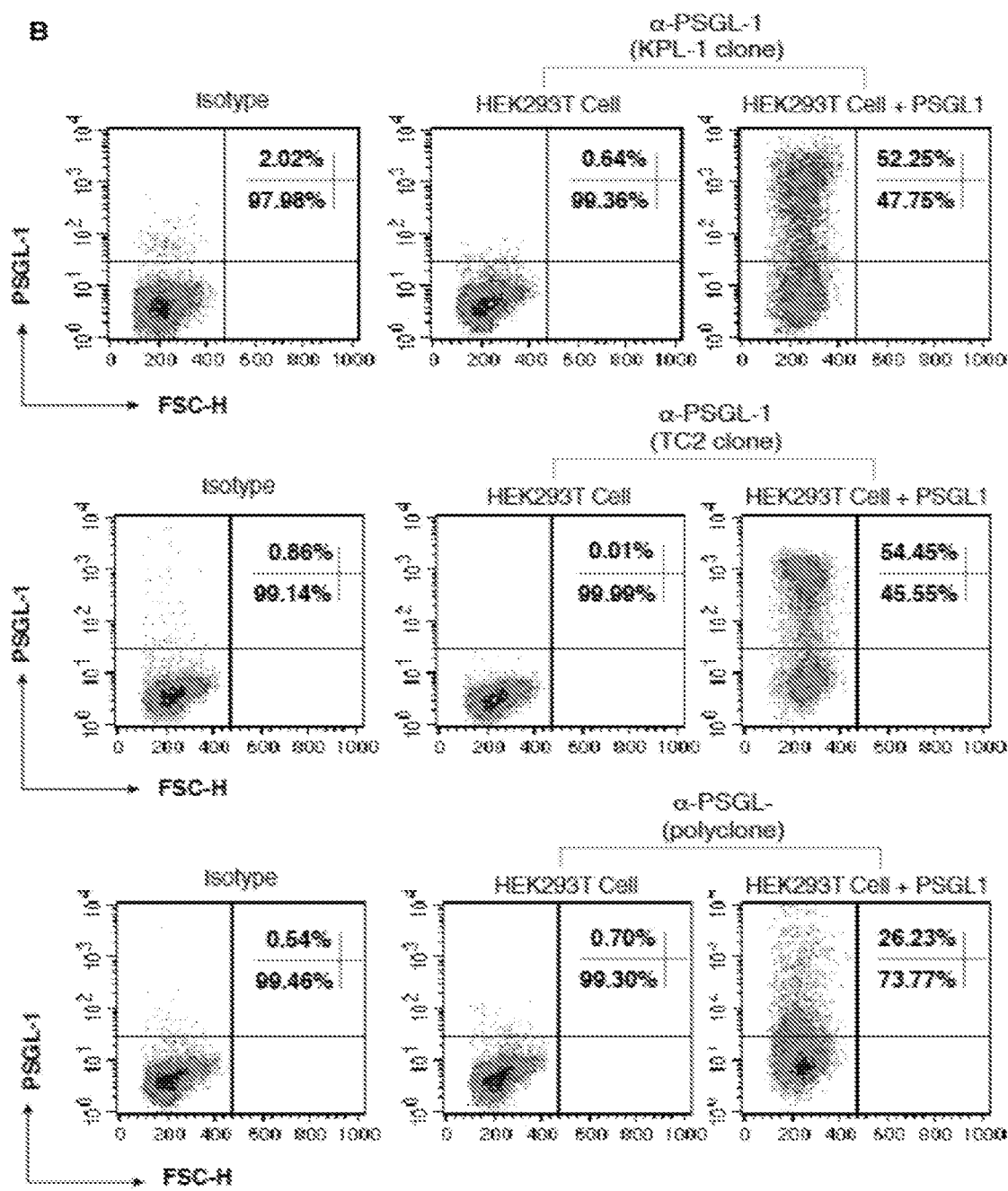
Figure 6C:
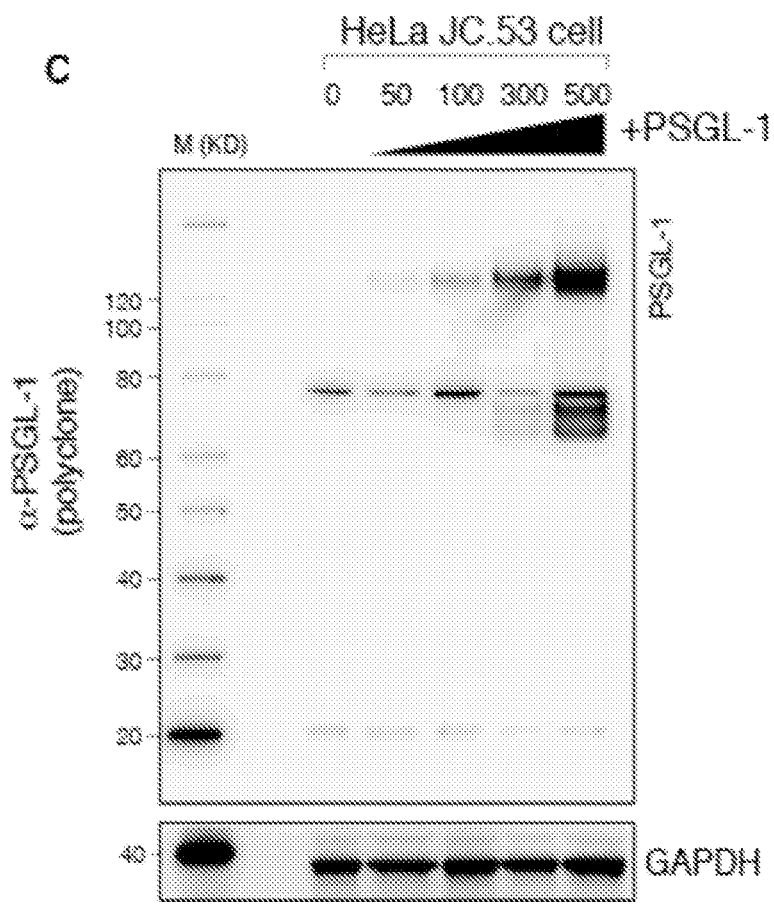

FIGS. 6A-6C: shows validation of PSGL-1 expression following transfection of HEK293T and HeLaJC.53 cells.

FIG. 6A: HEK293T cells were transfected with a PSGL-1 expression vector (pCMV3-PSGL-1), and analyzed by western blot using 3 different commercial antibodies.

FIG. 6B: Expression of PSGL-1 on the surface was analyzed by surface staining and flow cytometry. Shown are the percentages of cells with high or low PSGL-1 staining in each panel.

FIG. 6C: HeLaJC.53 cells were transfected with pCMV3-PSGL-1 at the indicated inputs (ng). PSGL-1 expression was analyzed by western blot at 48 hours post transfection using anti-PSGL-1 polyclonal antibodies. GAPDH was similarly analyzed as a loading control.

Figure 7A:
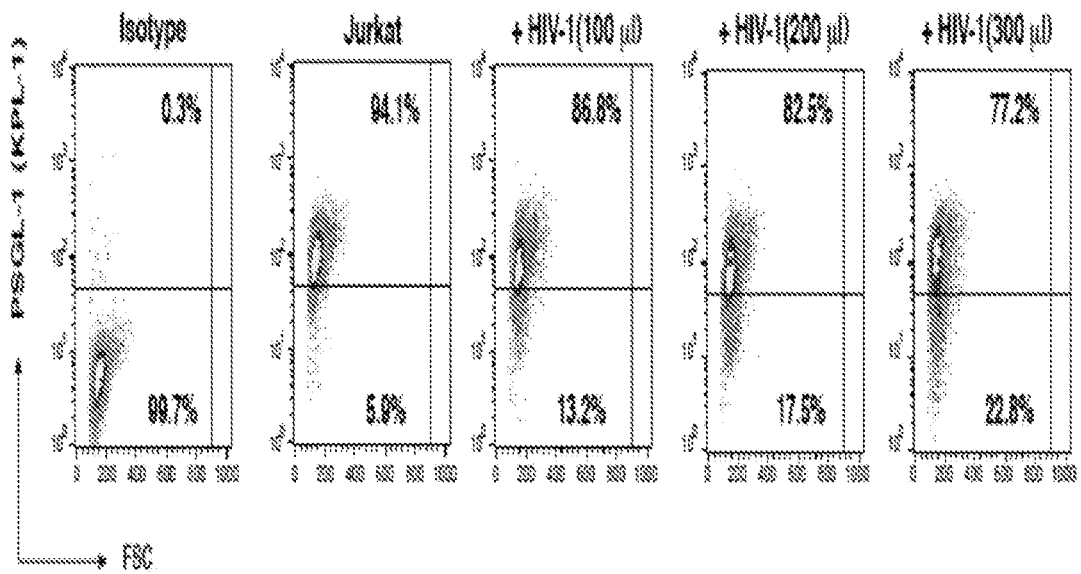
Figure 7B:
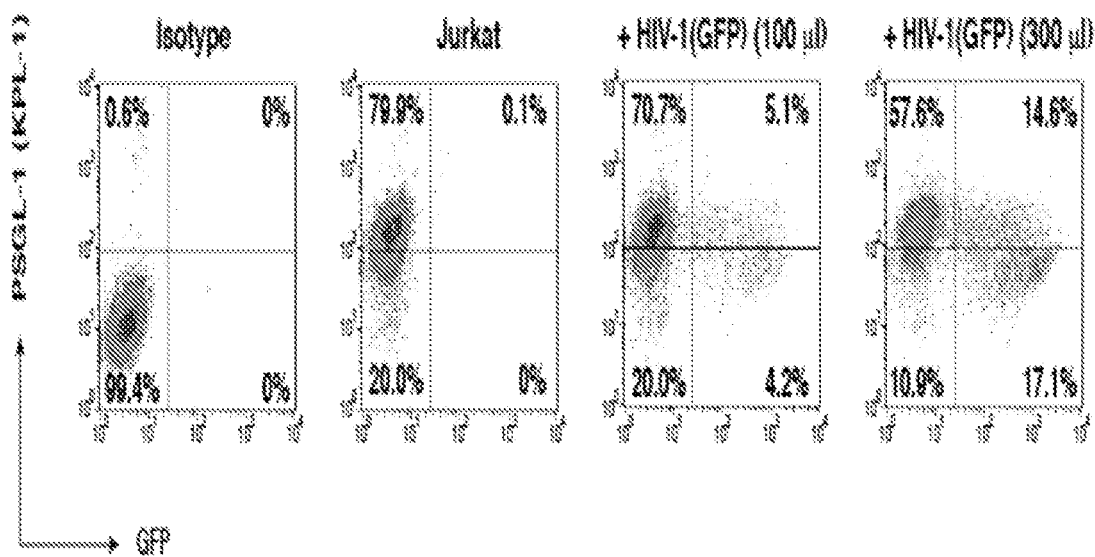

FIGS. 7A-7B: shows HIV-1 dose-dependent downregulation of PSGL-1 in Jurkat T cells.

FIG. 7A: Jurkat T cells were infected with different inputs of HIV-1, washed and cultured for 3 days, and then stained for surface PSGL-1 expression, and analyzed by flow cytometry. Shown are the percentages of cells with high or low PSGL-1 staining in each panel.

FIG. 7B: Cells were similarly infected with different inputs of a HIV-1 reporter virus. HIV-1 (GFP), and then stained for surface PSGL-1 expression. Shown are the percentages of the GFP+ or GFP− cells with low or high PSGL-1 staining in each panel.

Figure 8A:
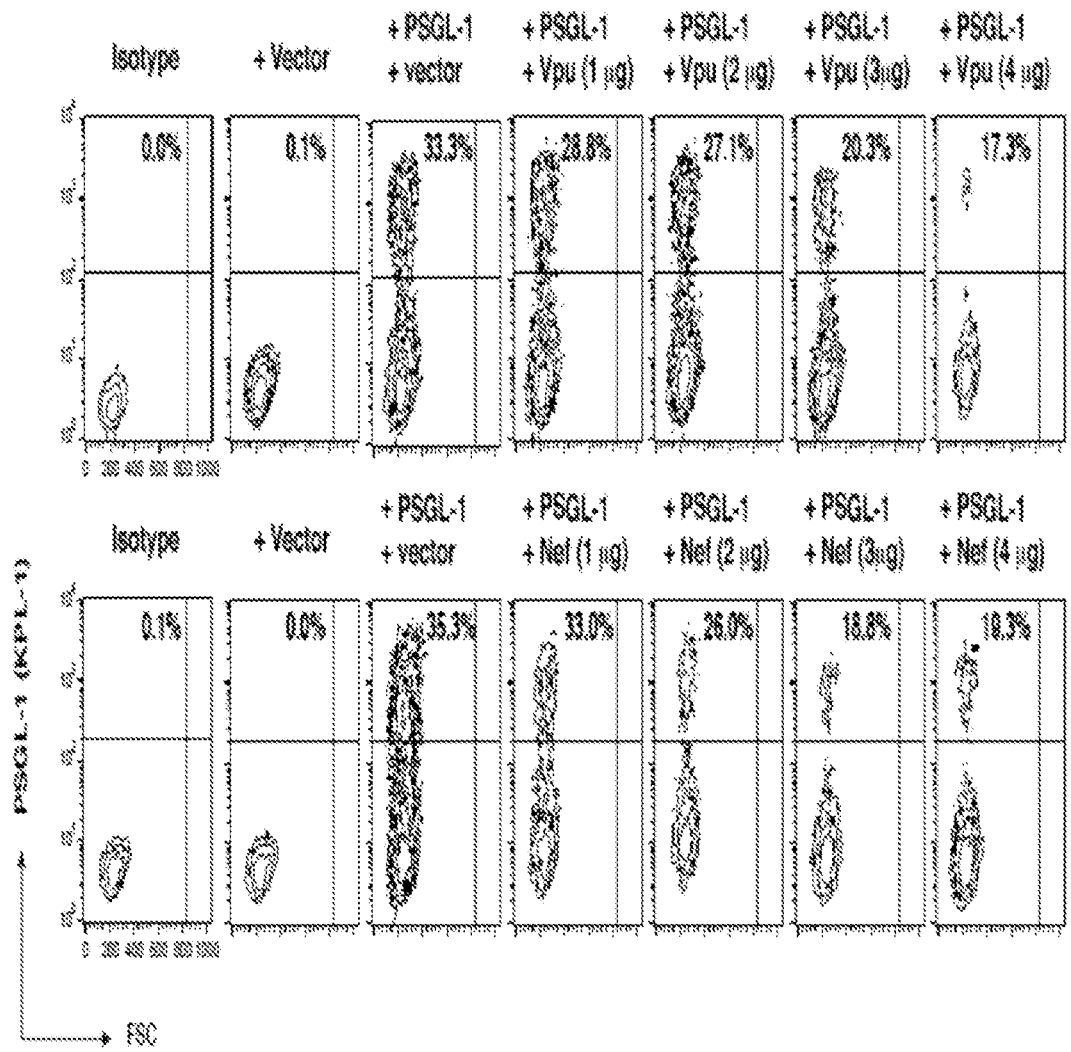
Figure 8B:
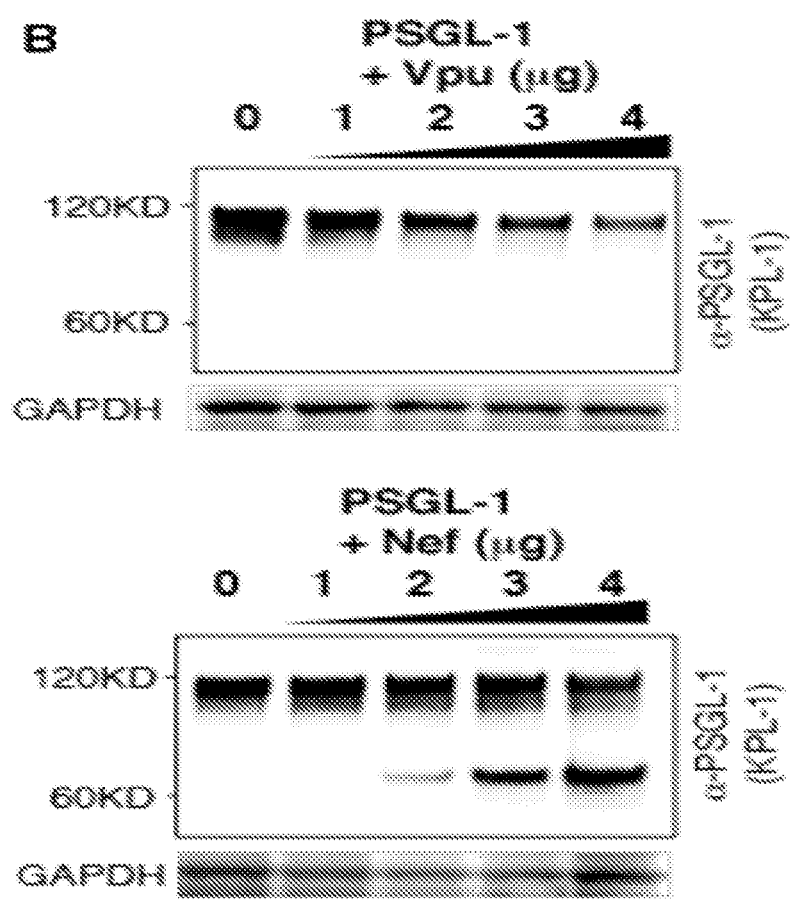

FIGS. 8A-8B: shows downregulation of PSGL-1 from the cell surface by Vpu and Nef.

FIG. 8A: HEK293T cells were co-transfected with PSGL-1 (100 ng) and a Vpu or Nef expression vector at various DNA inputs. Surface PSGL-1 expression was quantified and shown as the percentages of cells expressing PSGL-1. For controls, an empty vector was used (+Vector). The same amount of DNA was used in all transfections.

FIG. 8B: Levels of intracellular PSGL-1 in Vpu-or Nef co-transfected cells were quantified by western blot at 48 hours post-cotransfection.

Figure 9A:
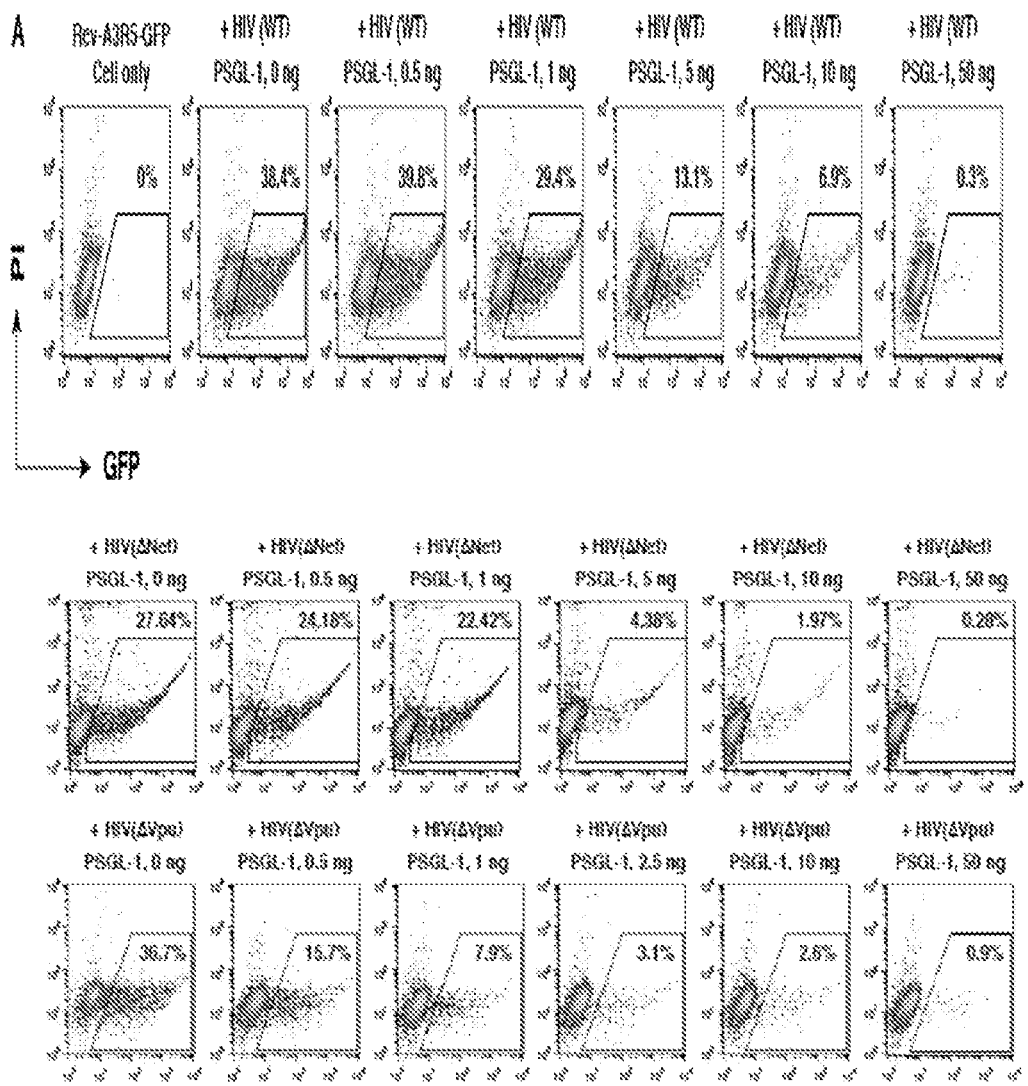
Figure 9B:
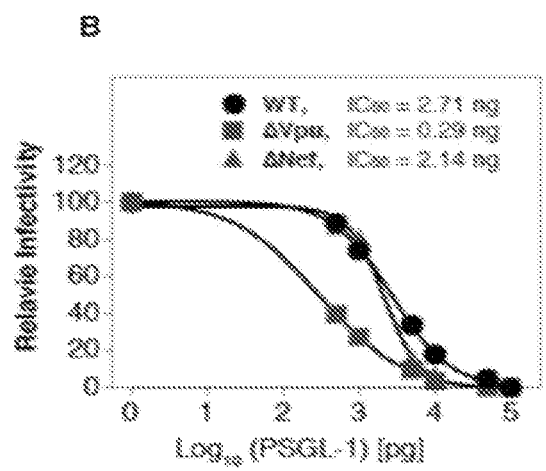

FIGS. 9A-9B: shows comparison of Vpu and Nef in antagonizing PSGL-1.

FIG. 9A: HEK293T cells were co-transfected with various amounts of PSGL-1 DNA (0.5-50 ng) plus 1 µg HIV (NL4-3) WT. HIV(ΔVpu), or HIVΔNef DNA. Virions were harvested and normalized for p24. Viral infectivity was quantified by infecting the T-cell line-derived Rev-A3R5-GFP indicator cell line. HIV-1 replication was quantified by GFP expression. Shown are the percentages of GFP+ cells at 48-72 hours post infection.

FIG. 9B: The PSGL-1 dose-dependent inhibition curve was plotted.

Figure 10A:
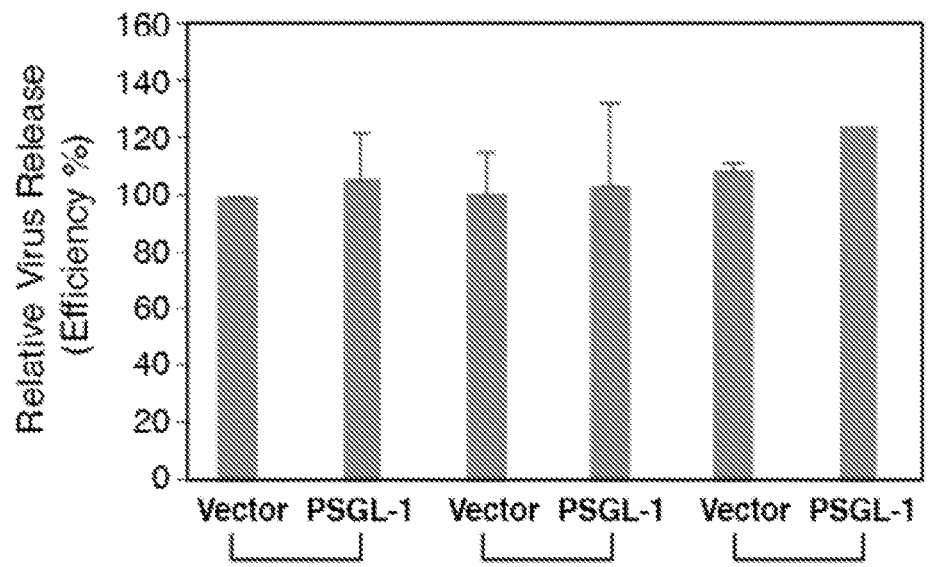
Figure 10B:
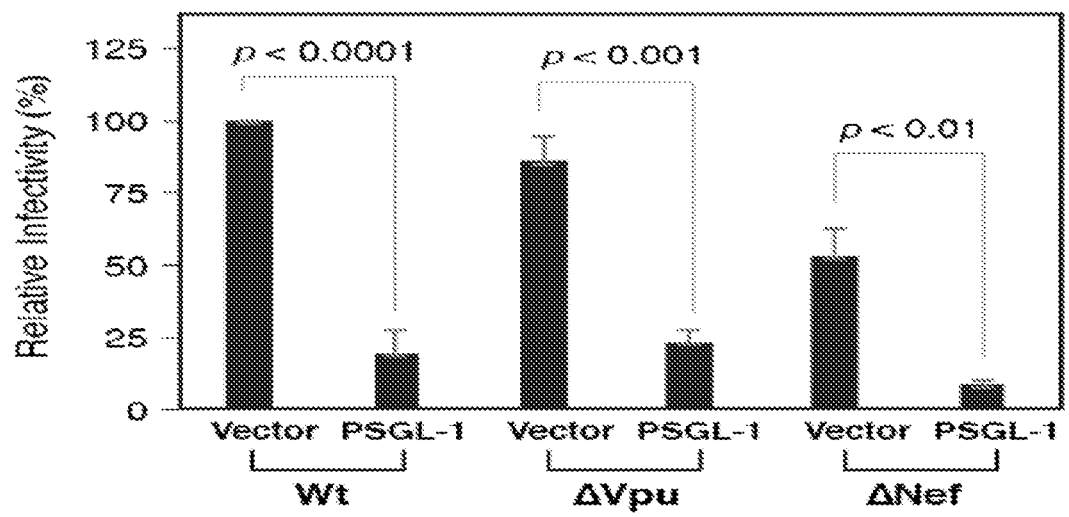

FIGS. 10A-10B: shows PSGL-1 inactivates HIV-1 infectivity.

FIG. 10A: HEK293T cells were cotransfected with 1µg of HIV-1(NL4-3), HIV-1(ΔVpu), or HIV-1(ΔNef) DNA plus 100 ng PSGL-1 expression vector. One day post-transfection, virus supernatants were harvested, and virus release efficiency (VRE) was quantified by western blot as the amount of virion-associated p24 (CA) relative to total Gag in cell and virus lysates. VRE was set to 100% for WT HIV-1 in the absence of PSGL-1.

FIG. 10B:, At 30 hours post-transfection, virus supernatants were harvested, and an aliquot was used for reverse transcriptase (RT) and infectivity assays. RT-normalized virus was used to infect TZM-b1 cells for 2 days, and luciferase activity was measured. Infectivity of WT HIV-1 in the absence of PSGL-1 was set to 100%. Data shown are ±SD from three independent experiments. Data were evaluated for statistical significance using the unpaired t test.

Figure 11:
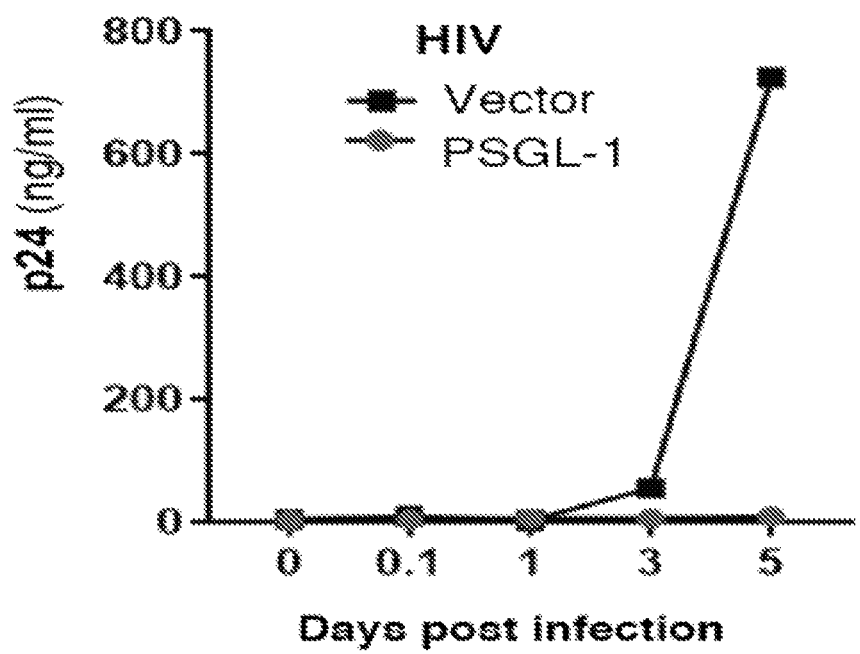

FIG. 11: shows PSGL-1 blocks the establishment of a spreading HIV-1 infection. HEK293T cells (3×106) were co-transfected with 12 µg of HIV(NL4-3) plus 2.4 µg pCMV-PSGL-1 or an empty vector. Viruses were harvested at 48 hours post-transfection and used to infect A3R5.7 CD4 T-cells. After infection for 4 hours, cells were washed and cultured for 5 days. HIV replication was analyzed by p24 release.

Figure 12:
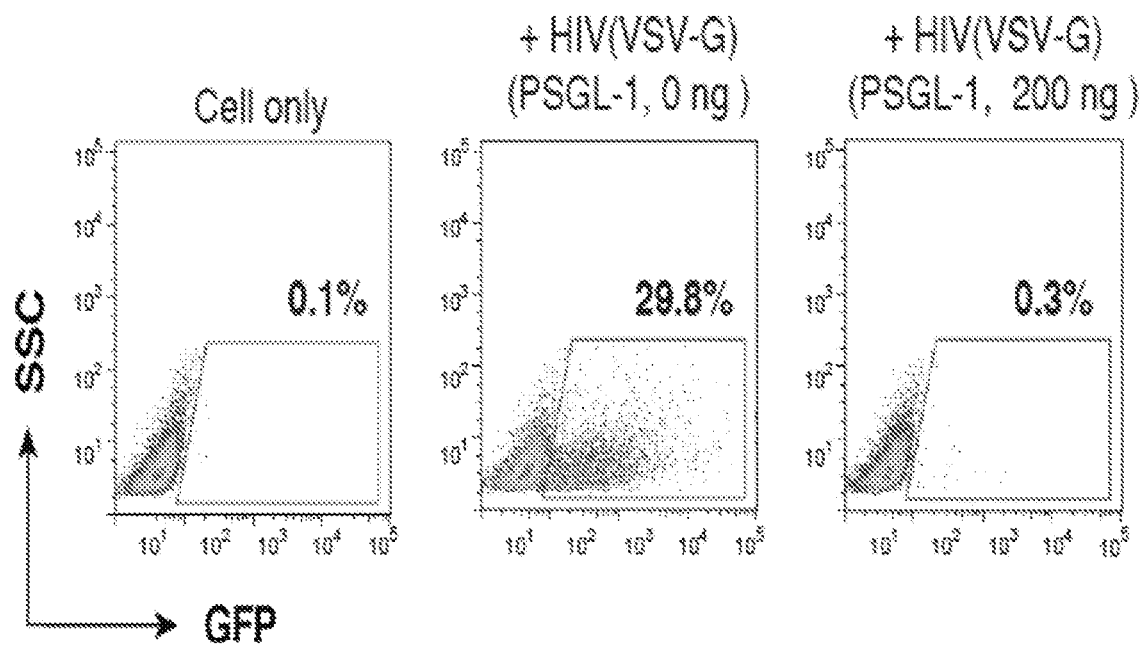

FIG. 12: shows PSGL-1 inactivates the infectivity of VSV-G-pseudotyped HIV-1 virions. HEK293T cells (2×105) were co-transfected with 1 µg of the Env(−) clone pNL4-3/KFS, 1 µg pHCMV-G, and 200 ng pCMV-PSGL-1 or an empty vector. Virus supernatants were harvested at 48 hours post-transfection, and used to infect Rev-A3R5-GFP cells. After infection for 4 hours, cells were washed and cultured in medium for 72 hours. The percentages of infected (GFP+) cells were quantified by flow cytometry.

FIGS. 13A-13C: shows PSGL-1 inactivates the infectivity of HIV-1 virions produced from CEM-SS cells.

FIG. 13A: CEM-SS cells were electroporated with HIV-1(NL4-3) DNA plus PSGL-1 DNA or an empty vector. PSGL-1 surface expression was quantified at 3 days post-electroporation.

FIG. 13B: To quantify HIV infectivity, virions were harvested at 3 days post-electroporation, and used to infect Rev-A3R5-GFP cells, using an equal amount of p24 for infection. GFP expression was quantified at 3 days post-infection.

FIG. 13C: Virions produced in the presence of PSGL-1 or the empty vector were assayed for attachment to target HeLa JC.53 cells at 4° C., for 2 hours. Cells were washed and then analyzed by western blot for bound p24.

FIGS. 14A-14B: shows shRNA knockdown of PSGL-1 in primary CD4 T cells enhances HIV-1 replication.

FIG. 14A: Blood resting CD4 T cells were purified by negative depletion, activated with anti-CD3 and CD28 magnetic beads, and then transduced with a lentiviral vector expressing shRNA against PSGL-1 (shRNA PSGL-1) or a non-target sequence (shRNA NTC). PSGL-1 surface expression was quantified at day 3 post-transduction.

FIG. 14B: Cells were also electroporated with HIV-1 (NL4-3) DNA, and viral replication in the PSGL-1 knockdown or the control NTC CD4 T cells was quantified by measuring p24 in the supernatant.

FIGS. 15A-15F: shows virion incorporation of WT PSGL-1.

Figure 15B:
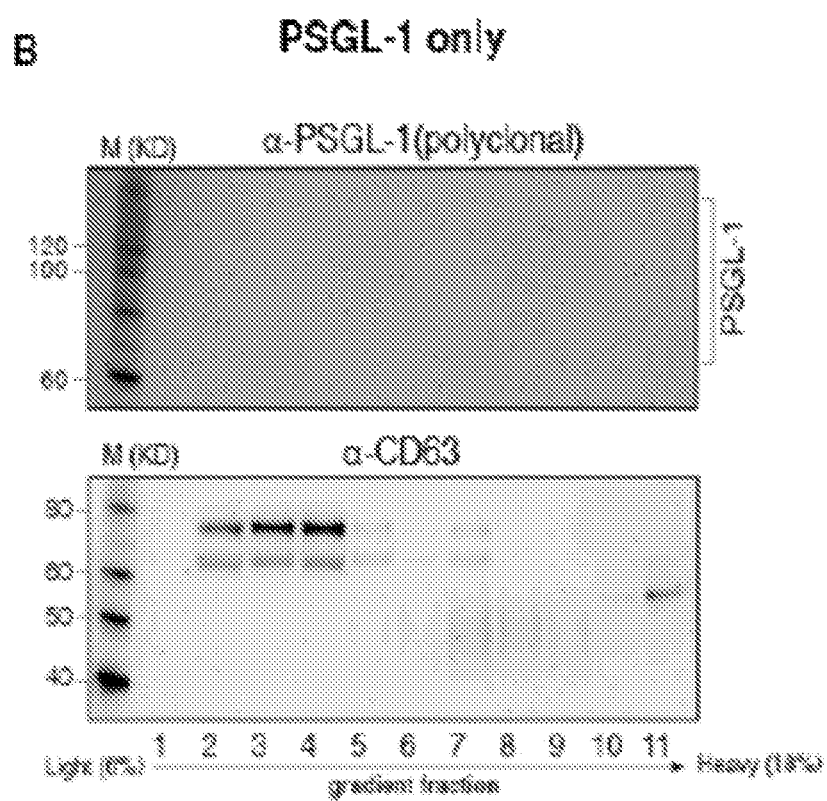
Figure 15C:
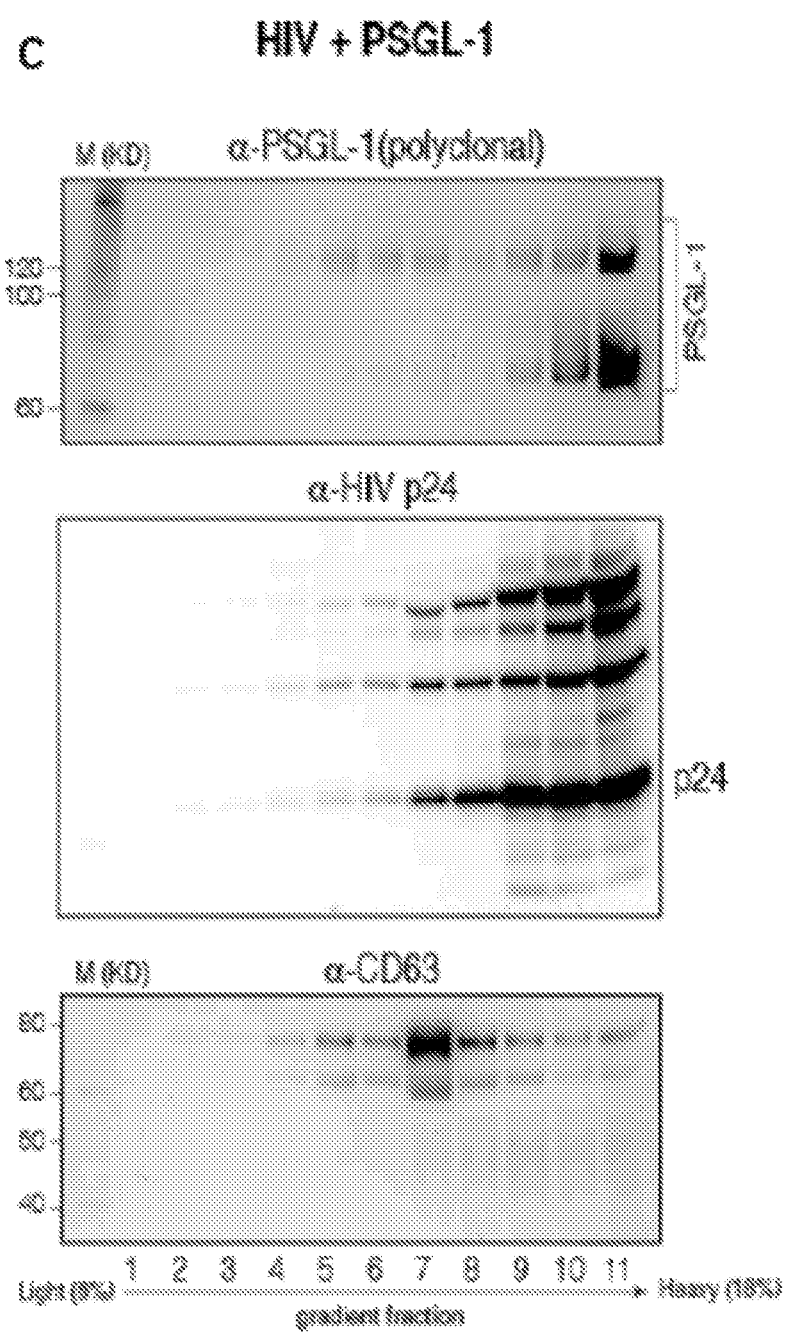

FIG. 15A to FIG. 15C: HEK293T cells were transfected with HIV-1(NL4-3) (1 μg, HIV only), or transfected with PSGL-1 (200 ng, PSGL-1 only), or co-transfected with 1 μg HIV-1(NL4-3) plus 200 ng of PSGL-1 DNA (HIV+PSGL-1). Supernatants were harvested at 48 hours, filtered, concentrated, and purified by ultra-speed centrifugation through a 6%-18% OptiPrep gradient. PSGL-1 and viral p24 proteins in each fraction were analyzed by western blot using antibodies against PSGL-1 (polyclonal) or HIV-1 p24 (anti-p24). For comparison, an anti-CD63 antibody was used to identify the fractions also containing exosomes.

FIG. 15A: shows HEK293T cells were transfected with HIV-1 (NL4-3) (1 ug, HIV only).

FIG. 15B: shows HEK293T cells were transfected with PSGL-1 (200 ng, PSGL-1 only).

FIG. 15C: shows HEK293T cells were transfected with co-transfected with 1 ug HIV-1 (NL4-3) plus 200 ng of PSGL-1 DNA (HIV + PSGL-1).

Figure 15D:
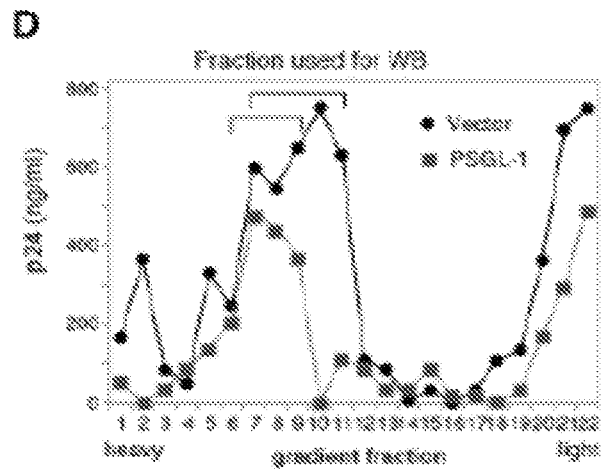
Figure 15E:
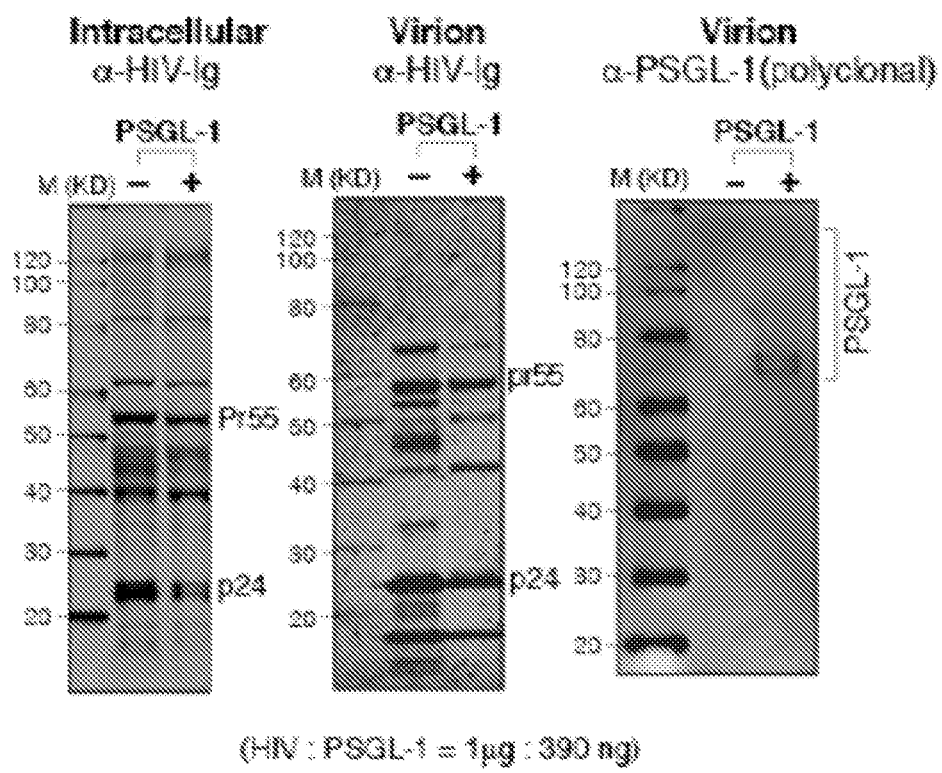

FIG. 15D and FIG. 15E) HEK293T cells were co-transfected with HIV-1(NL4-3) DNA plus PSGL-1 DNA at the indicated ratios. Virus particles were harvested at 48 hours and purified by ultra-speed centrifugation through an OptiPrep gradient (6%-18%).

FIG. 15D: The presence of viral p24 in each fraction was directly analyzed by p24 ELISA.

FIG. 15E: Expression of viral proteins in co-transfected cells was analyzed by western blot using antibodies against HIV-1 proteins (anti-HIV serum): virion proteins were also analyzed by harvesting and pelleting the peak virion fraction, and performing western blot using antibodies against PSGL-1 (polyclonal) or HIV-1 proteins (anti-HIV serum).

Figure 15F:
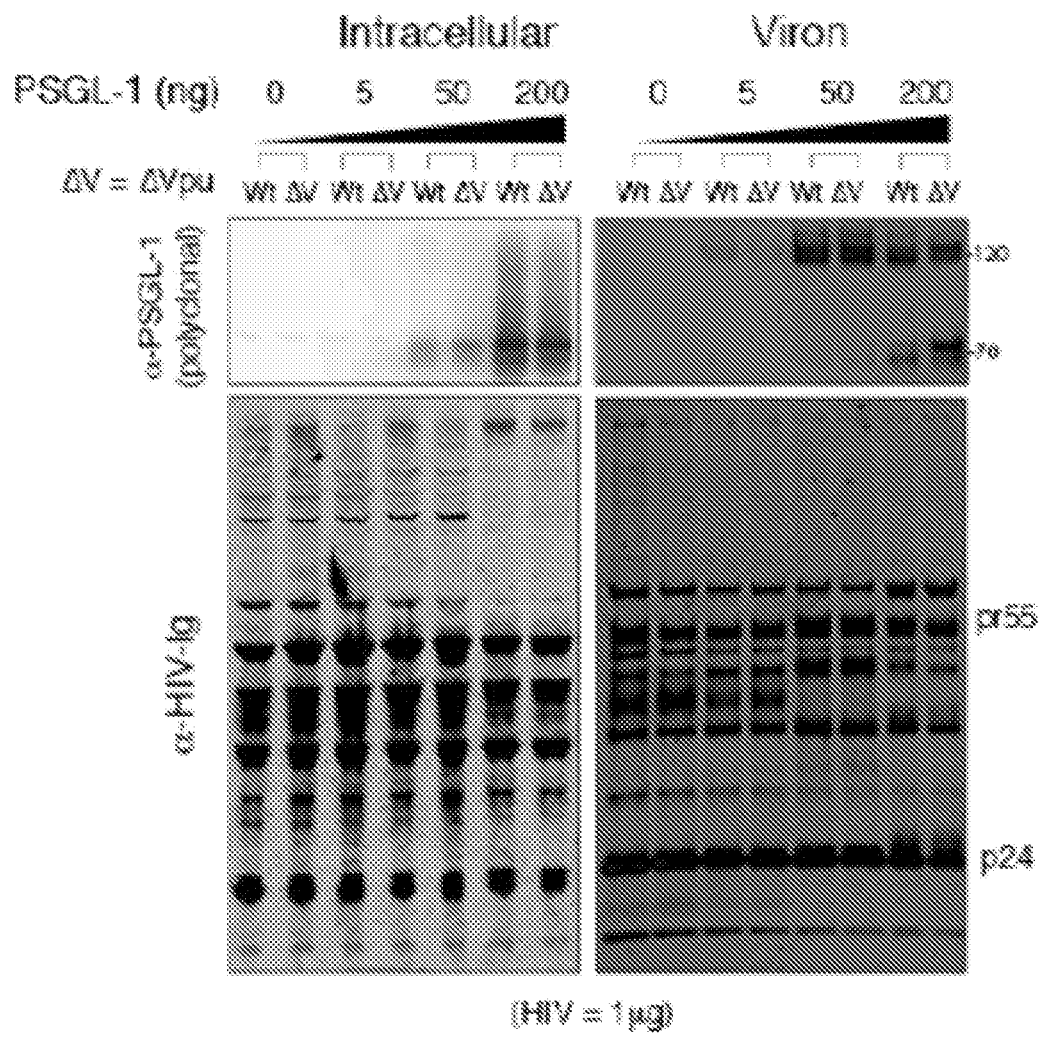

FIG. 15F: Positions of Gag precursor protein (pr55) and p24 (CA) are indicated. HEK293T cells were co-transfected with varying amounts of PSGL-1 DNA plus 1 μg HIV-1 (NL4-3) or HIV(ΔVpu) DNA at the indicated ratios. Virus particles were harvested at 48 hours and purified by ultra-speed centrifugation through an OptiPrep gradient (6%-18%). Intracellular and virion proteins were similarly analyzed by western blots for PSGL-1 and HIV-1 proteins.

FIGS. 16A-16E: shows PSGL-1 disrupts HIV-1 Env but not VSV-G incorporation into virions.

FIG. 16A and FIG. 16B: HEK293T cells were co-transfected with HIV-1 in the presence of PSGL-1 or an empty vector. Cells were also co-transfected with pNL4-3/KFS plus pCMV-VSV-G in the presence of PSGL-1 or an empty vector.

FIG. 16A: Virus particles produced were analyzed by western blot using antibodies against PSGL-1 (polyclonal), HIV proteins (anti-HIV serum), HIV-1 Env proteins (2F5 and 10E8), or VSV-G.

FIG. 16B: shows relative Env/p24 ratio.

FIG. 16C to FIG. 16E: Effects of PSGL-1 on virion incorporation of VSV-G, HEK293T cells were co-transfected with 10 μg pNL4-3/KFS, 2 μg pCMV-VSV-G, and 2 μg PSGL-1 or a control empty vector. Viral particles were harvested at 48 hours, filtered, concentrated, and purified by ultra-speed centrifugation through a 6%-18% OptiPrep gradient.

FIG. 16C: Virion proteins were analyzed by pelleting each fraction, and performing western blot using antibodies against VSVG.

FIG. 16D: Virion proteins were analyzed by pelleting each fraction, and performing western blot using antibodies against PSGL-1.

FIG. 16E: Virion proteins were analyzed by pelleting each fraction, and performing western blot using antibodies against HIV-1 p24 (anti-HIV p24).

FIGS. 17A-17D: shows expression and virion incorporation of PSGL-1 mutants.

Figure 17A:
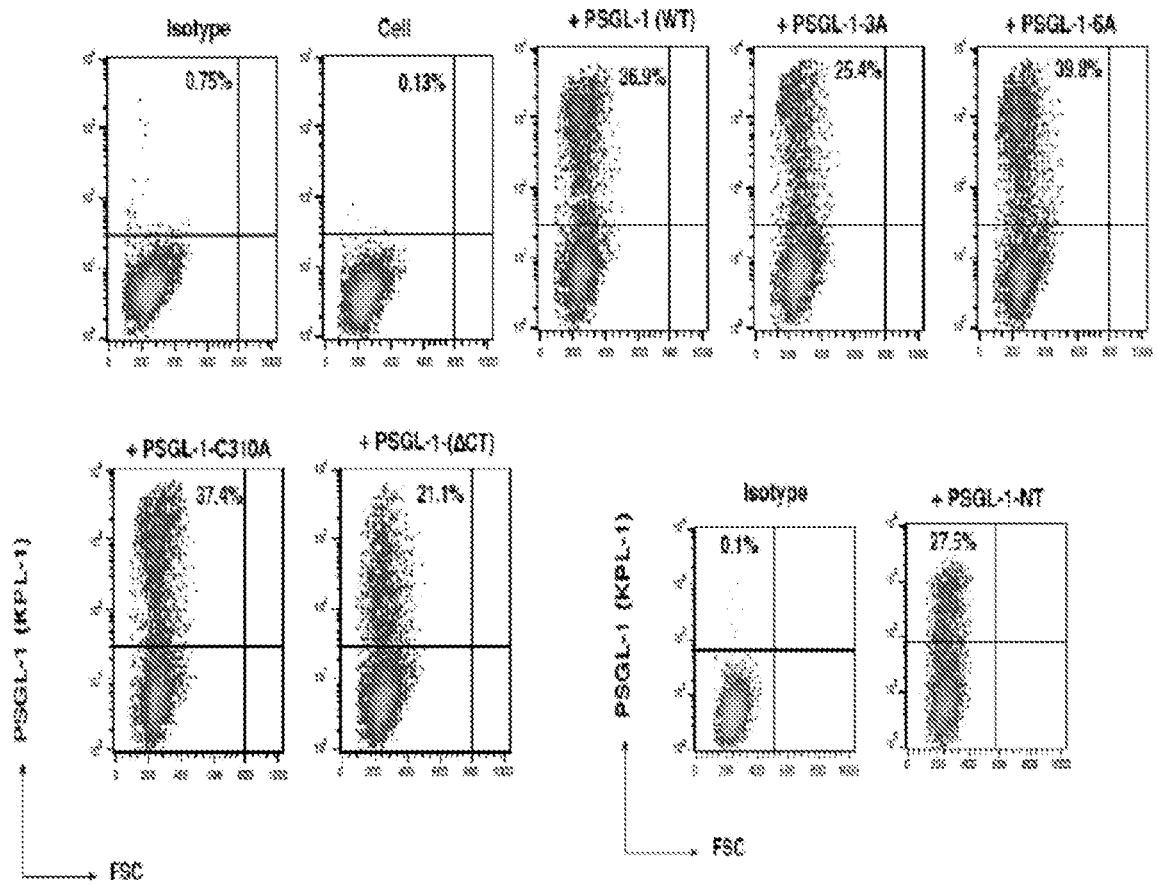

FIG. 17A: HEK293T cells were transfected with PSGL-1 DNA (500 ng) or each of the PSGL-1 mutant DNA (500 ng). Expression of PSGL-1 was quantified by surface staining with an anti-PSGL-1 antibody (KPL-1 clone) at 48 hours.

Figure 17B:
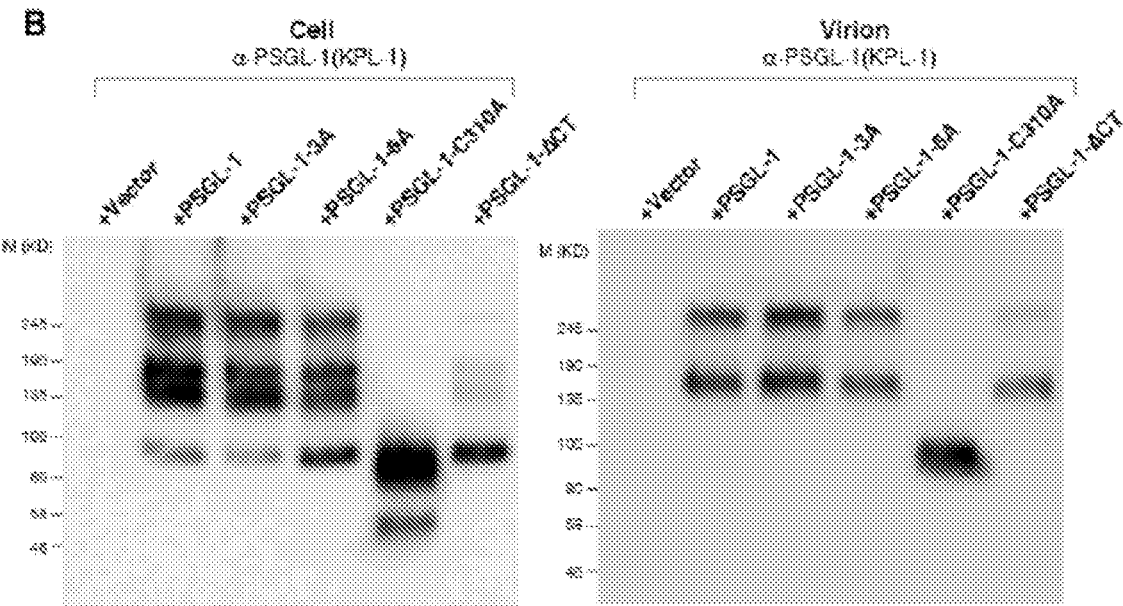

FIG. 17B: HEK293T cells were co-transfected with HIV-1 DNA (1 μg) plus PSGL-1 DNA or each of the PSGL-1 mutant DNAs (250 ng of PSGL-1, PSGL-1-3A. PSGL-1-6A and PSGL-1-C310A mutants: 500 ng of PSGL-1-ΔCT, pRetroPSGL-1, PSGL-1-NT, PSGL-1-CT and PSGL-1ΔDR).

Figure 17C:
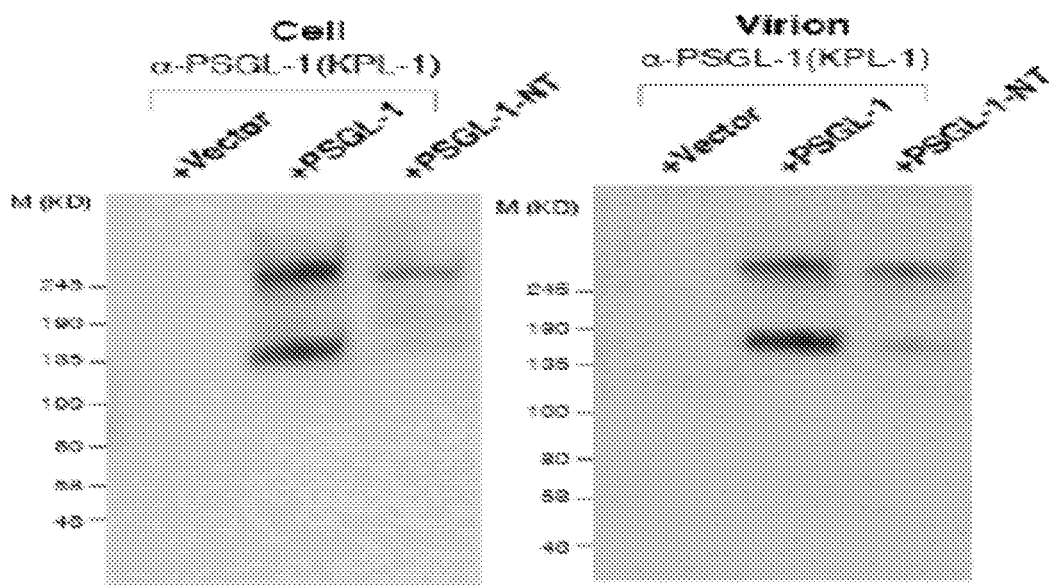

FIG. 17C: Expression of PSGL-1 or PSGL-1 mutants in co-transfected cells was detected by western blot. Viral particles were harvested, and virion incorporation of PSGL-1 was detected by western blotting using the anti-PSGL-1 antibody KPL-1.

Figure 17D:
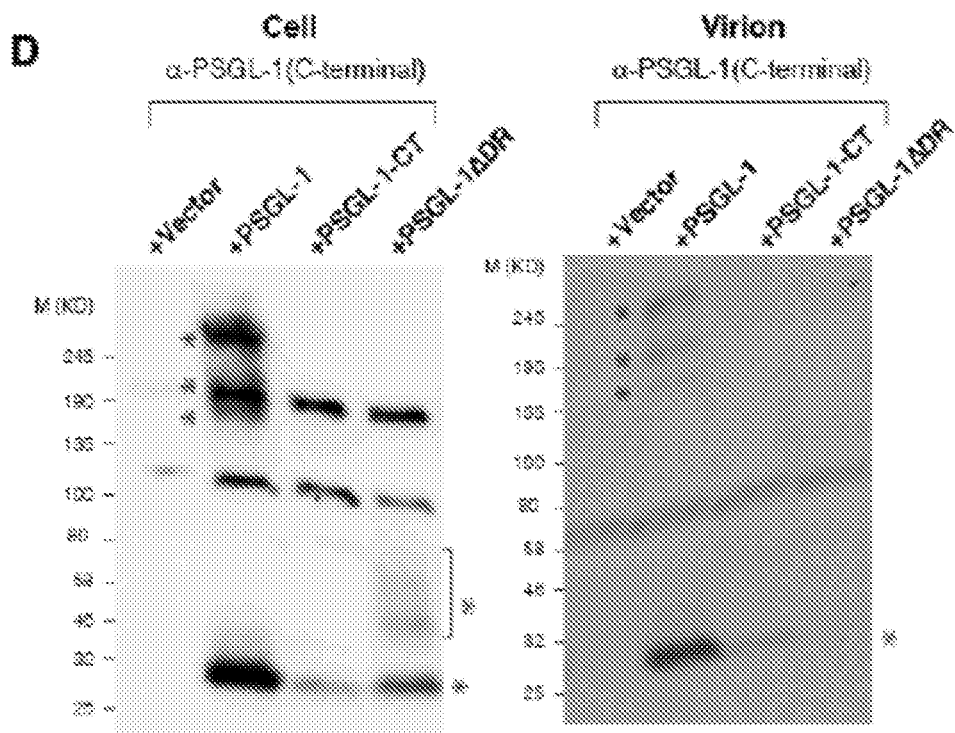

FIG. 17D: For the N-terminal truncation mutants. PSGL-1-CT and PSGL-1ΔDR, cellular expression and virion incorporation were detected by western blotting using the anti-PSGL-1 antibody ab66882 (Abcam). The expected protein sizes of PSGL-1 and the mutant proteins are labelled with red asterisk.

Figure 18:
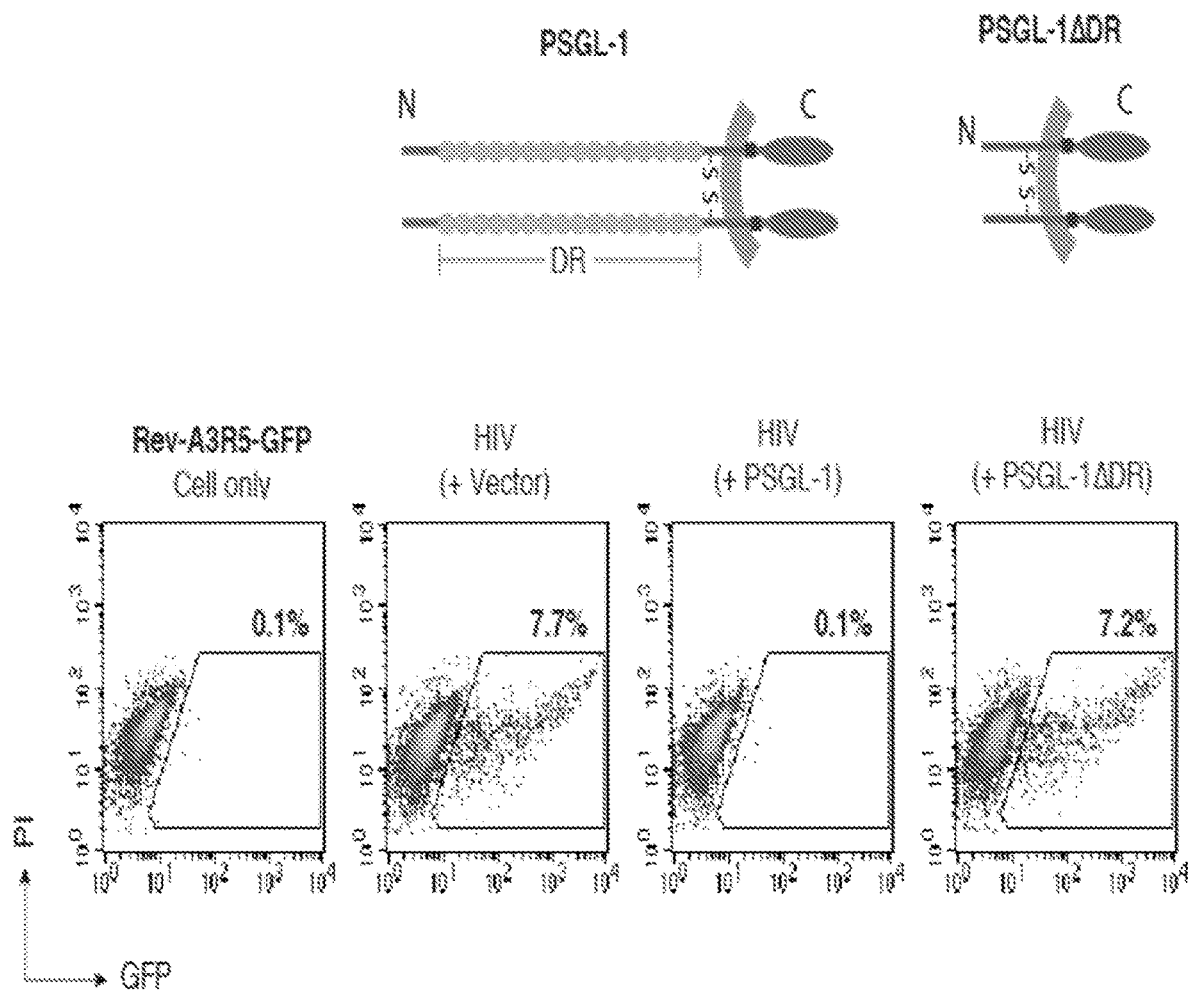

FIG. 18: shows the extracellular. N-terminal DR domain of PSGL-1 is required to block HIV-1 infectivity. HEK293T cells were co-transfected with HIV(NL4-3) DNA (1 μg) plus vectors expressing PSGL-1 or PSGL-1 decameric repeat (DR) truncation mutant PSGL-1ΔDR (400 ng). Virions were harvested at 48 hours post-transfection and normalized for p24, and viral infectivity was quantified by infecting Rev-A3R5-GFP indicator cells. HIV-1 replication was quantified by GFP expression. An empty vector was used as the co-transfection control (+Vector).

FIGS. 19A-19C: shows CD43 inactivates HIV-1 virion infectivity.

FIG. 19A: HEK293T cells were co-transfected with various amounts of CD43 DNA (0.5-400 ng) plus 1 μg HIV (NL4-3) DNA. Virions were harvested at 48 hours and normalized for p24. Viral infectivity was quantified by infecting Rev-A3R5-GFP indicator cells. HIV-1 replication was quantified by GFP expression. Shown are the percentages of GFP+ cells at 48 hours post-infection.

FIG. 19B: The CD43 dose-dependent inhibition curve was plotted.

FIG. 19C: Downregulation of CD43 from the cell surface by Vpu and Nef. HEK293T cells were co-transfected with CD43 (100 ng) and a Vpu or Nef expression vector (4 μg). Surface CD43 expression was quantified and shown as the percentage of cells expressing CD43. For controls, an empty vector was used (+vector). The same amount of DNA was used in all transfections.

DETAILED DESCRIPTION OF THE PREFERRED EMBODIMENT

Definitions and General Techniques

For simplicity and clarity of illustration, the drawing figures illustrate the general manner of descriptions and techniques.

The terms "first." "second." "third." "fourth." and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include." and "have." and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items, and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has." "have." "having." or the like are intended to be open-ended terms. Further, the phrase "based on" is intended to mean "based, at least in part, on" unless explicitly stated otherwise.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

By "glycoprotein" is meant by a protein which contain oligosaccharide chains (glycans) covalently attached to amino acid side-chains. The carbohydrate is attached to the protein in a cotranslational or post-translational modification.

The term "PSGL-1" as used herein refers to P-selectin glycoprotein ligand-1, which is a membrane protein that mediates the surface tethering and rolling of Th1 T cells for tissue migration, and has been suggested to be up-regulated by Th1 cytokines such as interferon gamma. PSGL-1, also known as SELPLG or CD162, is primarily expressed on the surface of lymphoid and myeloid cells and binds to all three members of the selectin family of proteins, P-, E-, and L-selectin. PSGL-1 is up-regulated during inflammation to mediate leukocyte tethering and rolling on the surface of the endothelium to promote leukocyte migration into inflamed tissues. In a mouse model of chronic viral infection, PSGL-1 has been reported to be an immune factor regulating T-cell checkpoints. In addition, PSGL-1 serves as a receptor for enterovirus 71 (EV71) infection of leukocytes. PSGL-1 has also been shown to be an INF-γ-regulated factor involved in Th 1-mediated antiviral activity. During T-cell differentiation, culturing T cells in the Th1 cytokine INF-γ and IL-12 promoted PSGL-1 expression preferentially in the INF-γ-producing T-cell population, suggesting that PSGL-1 could be an INF-γ-regulated factor involved in Th1-mediated antiviral activity. PSGL-1 was reported to co-cluster with HIV-1 Gag at sites of assembly in the T-cell uropod.

A "selectin" is a family of cell adhesion molecules (or CAMs). Selectins comprise a family of three members (E-, P-, and L-selectin) that are differentially expressed by leukocytes and endothelial cells, and are involved in the early steps of leukocyte extravasation.

An "Interferons or IFNs" are a group of signaling proteins made and released by host cells in response to the presence of several viruses. A virus-infected cell will release interferons causing nearby cells to heighten their anti-viral defenses.

An "Interleukin (IL)", any of a group of naturally occurring proteins that mediate communication between cells. Interleukins regulate cell growth, differentiation, and motility. They are particularly important in stimulating immune responses, such as inflammation.

A term "T-cell" is a type of lymphocyte, which develops in the thymus gland and plays a central role in the immune response. T-cells can be distinguished from other lymphocytes by the presence of a T-cell receptor on the cell surface.

The term "ligand" is a substance that forms a complex with a biomolecule to serve a biological purpose.

The term "CD4 (cluster of differentiation 4)" is a glycoprotein found on the surface of immune cells such as T helper cells, monocytes, macrophages, and \ dendritic cells.

The term "target cell" or "host cell" means a cell that is to be transformed using the methods and compositions of the invention.

The term "virus or virion" as used herein refers to a submicroscopic infectious agent that is unable to grow or reproduce outside a host cell. It is non-cellular but consisting of a core of DNA or RNA surrounded by a protein coat. A virus is a small parasite that cannot reproduce by itself. Once it infects a susceptible cell, however, a virus can direct the cell machinery to produce more viruses. Virus and virion as used herein are synonymous.

The term "pseudotyping" as used herein refers to a process of producing viruses or viral vectors in combination with foreign viral envelope proteins. The result is a pseudotyped virus particle. With this method, the foreign viral envelope proteins can be used to alter host tropism or an increased/decreased stability of the virus particles. Pseudotyped particles do not carry the genetic material to produce additional viral envelope proteins, so the phenotypic changes cannot be passed on to progeny viral particles. For example, pseudotyping allows one to specify the character of the envelope proteins. A frequently used protein is the glycoprotein G of the Vesicular stomatitis virus (VSV), short VSV-G. These envelope proteins transduce to all cell types.

The term "virus particle or virion particle" as used herein refers to a complete infectious agent that consists of an RNA or DNA core with a protein coat sometimes with external envelopes and that is the extracellular infective form of a virus.

The term "HIV" as used herein refers to human immunodeficiency virus. Infection of subjects with HIV can result in diseases, including acquired immune deficiency syndrome (AIDS).

The term "subject" as used herein refers to a human individual. This individual could be a patient requiring prophylaxis and/or medical treatment.

The term "vaccine" as used herein refers to a suspension of antigens derived from viruses or bacteria that, upon administration, will produce active immunity and provide protection against those viruses or bacteria or related viruses or bacteria The term "virus producing cell" as used herein refers to cell that a virus has infected and whose cell machinery the virus can direct to produce more viruses.

The term "expressing or overexpressing PSGL-1" in virus producing cells as used herein refers to causing the protein PSGL-1 to be synthesized by the cell in larger quantities than would normally be expressed by the cell on its own.

The term "non-infectious virus particle" as used herein refers to a virus particle that has been rendered unable to infect a host cell and cause one or more effects, such as disease or death of the host cell.

The term "attenuated virus particle" as used herein refers to a virus particle that has been weakened in its ability to infect a host cell and cause one or more effects, such as disease or death of the host cell.

The term "inactivated virus particle" as used herein refers to a virus particle that has been rendered unable to infect a host cell and cause one or more effects, such as disease or death of the host cell.

The term "vector" as used herein refers to an agent (i.e., a DNA construct) that can be used to introduce into a cell or organism genetic material that directs the synthesis of a protein that is encoded by the genetic material.

The term "human" as used herein refers to one that is not chimeric (e.g., not "humanized") and not from (either in whole or in part) a nonhuman species The term "Jurkat cells" as used herein refers to an immortalized line of human T lymphocyte cells that are used to study acute T cell leukemia, T cell signaling, and the expression of various chemokine receptors susceptible to viral entry, particularly HIV.

An embodiment relates to molecular details of PSGL-1 restriction of viral such as but not limited to HIV-1 infection of human CD4 T cells.

An embodiment relates to a method for expressing a PSGL-1 or a mutant thereof in a virus producing cell; and blocking virus infection by inactivating infectivity of a released virion from the virus producing cell.

An embodiment relates to a method for expressing a PSGL-1 or a mutant thereof in a virus producing cell; and blocking virus infection by inactivating infectivity of a released virion from the virus producing cell.

An embodiment relates to the molecular details of PSGL-1 restriction of HIV-1 infection of human CD4 T cells were investigated.

An embodiment relates in a single cycle of HIV-1 infection, ectopic expression of PSGL-1 in target cells did not inhibit HIV infection.

In an embodiment, the presence of PSGL-1 in virus-producing cells inhibits the processing and incorporation of the HIV-1 envelope (Env) glycoprotein, disrupting progeny virion attachment to target cells.

In an embodiment VSV-G (glycoprotein G of the Vesicular stomatitis virus) pseudotyping of HIV-1 virions, particle binding and infectivity were blocked by PSGL-1 without reducing VSV-G incorporation into virions.

In an embodiment, PSGL-1 in virions likely blocks viral infectivity through structural hindrance of particle binding to target cells. Functional mapping of PSGL-1 demonstrated that the extracellular, N-terminal domain of PSGL-1, but not PSGL-1 dimerization, is required for its anti-HIV-1 activity.

In an embodiment, a monomeric E-selectin-binding glycoprotein CD43 also effectively blocks HIV infectivity.

In an embodiment, E-selectin-binding glycoprotein CD43 blocks HIV infectivity with a potency similar to that of PSGL-1, suggesting a shared property of selectin ligands in blocking viral infectivity.

In an embodiment, PSGL-1 in addition to disrupting the binding of HIV-1 virions to target cells, PSGL-1 expression in the virus-producer cell is also capable of interfering with the infectivity of another retrovirus-MLV (murine leukemia viruses)—and the influenza A virus.

In one embodiment, PSGL-1-mediated suppression of virus infectivity extends to another retrovirus-murine leukemia virus—and to influenza A virus.

In one embodiment PSGL-1 can inactivate viruses in cell culture conditions. It was found that during the production of MLV viruses, if PSGL-1 DNA was co-transfected with MLV DNA. PSGL-1, the virions released became non-infectious. These results suggest that PSGL-1 can be used to inactivate other viral particles. The methods can be used to help the development of new methods for making live attenuated vaccines for viruses such as EAV (Equine Amemia virus) or Influenza viruses.

An embodiment relates to, a viral vaccine comprising live attenuated, inactivated, or non-infectious virus particles or virions, wherein the virus particles or virions are produced in virus producing cells, and wherein a selectin glycoprotein like PSGL-1 or CD43 or mutants thereof is expressed or overexpressed in the virus producing cells.

In an embodiment, the viral vaccine could be for human immunodeficiency virus (HIV), a murine leukemia virus (MLV), an influenza virus, EAV (Equine Amemia virus) or Influenza viruses or similar thereof.

An embodiment features a system comprising a virus vaccine comprising live attenuated, inactivated, or non-infectious viral particles.

Another embodiment features a system comprising a virus vaccine comprising live attenuated, inactivated, or non-infectious viral particles, wherein the viral particles are produced in virus producing cells, and wherein PSGL-1 is expressed or overexpressed in the virus producing cells. Furthermore, the system does not require a chemical that destroy a structure of the viral producing cells. The virus infection is a human immunodeficiency virus (HIV), a murine leukemia virus (MLV), an influenza virus or similar thereof.

An embodiment features a system comprising a virus vaccine comprising live attenuated, inactivated, or non-infectious viral particles, wherein the viral particles are produced in virus producing cells, and wherein CD43 is expressed or overexpressed in the virus producing cells. Furthermore, the system does not require a chemical that destroy a structure of the viral producing cells. The virus infection is a human immunodeficiency virus (HIV), a murine leukemia virus (MLV), an influenza virus or similar thereof.

An embodiment relates to a system capable of performing a method comprising administering a vaccine comprising live attenuated, inactivated, or non-infectious HIV particles to a subject in need of the vaccine; and treating or preventing one or more disease states in the subject resulting from HIV infection.

An embodiment relates to a system capable of performing a method comprising administering a vaccine comprising live attenuated, inactivated, or non-infectious HIV particles, wherein the HIV particles are produced in virus producing cells, and wherein PSGL-1 is expressed or overexpressed in the virus producing cells, to a subject in need of the vaccine; and treating or preventing one or more disease states in the subject resulting from HIV infection.

An embodiment relates to a method, comprising expressing or overexpressing PSGL-1 in HIV producing cells; isolating HIV particles from the HIV producing cells; and preparing the isolated HIV particles as a HIV vaccine. The HIV particles may be non-infectious, attenuated, or inactivated. Furthermore, the method does not require a chemical that destroy a structure of the HIV producing cells.

An embodiment relates to a use of PSGL-1 or CD43 in virions to block the infectivity of HIV-1 particles or other virus particles by preventing the binding of particles to target cells.

An embodiment relates to a broad-spectrum anti-viral product comprising: a vector expressing a selectin glycoprotein or like PSGL-1 or CD43 a mutant thereof in a virus producing cell; and blocking a virus infection by inactivating infectivity of a released virion from the virus producing cell.

In one embodiment PSGL-1 restricts viral infection through a novel "kill and release" mechanism, overexpression of PSGL-1 promotes virion release, and the released virions lose infectivity. PSGL-1 restricts HIV spreading through direct virion incorporation, which inactivates progeny virion attachment and entry into CD4 T cells.

In an embodiment, PSGL-1 restricts HIV infection through promoting the release of non-infectious virion particles. Given that the released virion particles are not able to attach to target cells, these particles are likely endocytosed by antigen presenting cells, and processed as antigens for MHC class II antigen presentation to stimulate anti-viral humoral immunity.

Another embodiment PSGL-1 inhibits the infectivity of VSV-G pseudo-typed lentiviruses, demonstrating that PSLG-1 potentially has broad anti-viral activity against different viruses. PSGL-1 can be used to inactivate viral infectivity for producing live-attenuated viral vaccines.

An embodiment relates to PSGL-1 restricts HIV infection through promoting the release of non-infectious virion particles. Given that the released non-infectious virion particles are not able to attach to target CD4 T cells, these particles are likely endocytosed by antigen presenting cells, and processed as antigens for MHC class II antigen presentation to stimulate anti-HIV humoral immunity.

Yet another embodiment PSGL-1 promotes the release of non-infectious virions ("kill and release"). The inactivation by PSGL-1 of virion infectivity may occur through blocking the protease processing of virion proteins. Some of the most abundant cellular proteins in the virion particles are actin and cofilin (10-15% and 2-10% of gag). HIV reverse transcriptase, nuclear capsid, and Nef have been shown to bind to actin directly. It is possible that F-actin may serve as a scuffled protein to organize the proper positioning of various virion proteins and their precursors. PSGL-1 may interfere with the organization of virion proteins and affect their proper processing by protease.

An embodiment relates to a PSGL-1, a mucin-like glycoprotein expressed on blood resting CD4 T cells, restricts HIV-1 virion infectivity. In this respect, PSGL-1-mediated restriction resembles that imposed by the Apobec3G, SERINC5, MARCH, GBP5, and 90K proteins, which also target virion infectivity. In contrast to the Vpu-antagonized restriction factor BST2/tetherin that tethers virion particles to the cell surface, PSGL-1 does not inhibit virion release, PSGL-1-imprinted virions lose the ability to attach to, and infect, target cells. PSGL-1 is a remarkably potent inhibitor of HIV-1 infectivity; it almost completely inactivated WT HIV-1 (WT is HIV derivative like Vpu) particle infectivity at a vector-to-proviral DNA ratio of 0.05. Given this high potency, it appears that HIV-1 uses two of its accessory proteins, Vpu and Nef, to antagonize PSGL-1.

An embodiment provides novel insights into the ability of the host cell to interfere with HIV-1 infection, and the biological function of lentiviral accessory proteins. Further elucidation of the mechanism by which PSGL-1 restricts HIV-1 infection may offer new therapeutic strategies for targeting HIV-1 replication.

An embodiment relates to PSGL-1, a mucin-like glycoprotein expressed on blood CD4 T cells, restricts HIV-1 virion infectivity primarily by interfering with particle binding to target cells. Human cells possess an antiviral activity that inhibits the release of retrovirus particles, and other enveloped virus particles, and is antagonized by the HIV-1 accessory protein, Vpu. This antiviral activity can be constitutively expressed or induced by interferon-α, and it consists of protein-based tethers called 'tetherins', that cause retention of fully formed virions on infected cell surfaces. The HIV-1 accessory protein Vpu counteracts a host factor that restricts virion release from infected cells. The interferon-induced cellular protein BST-2/HM1.24/CD317 is such a factor. BST-2 is downregulated from the cell surface by Vpu, and BST-2 is specifically expressed in cells that support the Vpu phenotype. Exogenous expression of BST-2 inhibits HIV-1 virion release, while suppression of BST-2 relieves the requirement for Vpu.

Another embodiment states that in contrast to the Vpu-antagonized restriction factor BST2/tetherin, which tethers virus particles to the cell surface, PSGL-1 does not inhibit virion release. PSGL-1 is a remarkably potent inhibitor; it almost completely inactivates WT HIV-1 particle infectivity at a vector-to-proviral DNA ratio of 0.05:1 (illustrated in FIG. 2G). In the context of VSV-G-pseudotyped HIV-1 particles, PSGL-1 expression markedly restricts particle infectivity without reducing VSV-G incorporation. It has been noted that HIV-1 particles bind target cells even in the absence of Env receptor interactions. Remarkably, even when HIV-1 particles are devoid of viral glycoproteins. PSGL-1 in the producer cell interferes with particle binding to target cells. In addition to direct effects on Env processing and incorporation (illustrated in FIG. 16A and 16B), the presence of PSGL-1 on the virion surface may sterically disrupt binding of virions to target cells. PSGL-1 has a highly extended structure, with the extracellular portion projecting nearly 60 nm from the cell surface, and the extracellular domain is heavily glycosylated and is relatively rigid. These intrinsic structural features (illustrated in FIG. 4A) may occlude the interaction of the particle with viral glycoprotein receptors and may also reduce non-specific binding between the virion and cells.

An embodiment relates to PSGL-1 expression is strongly inhibitory in our HIV-1 spreading assay, in which much of the viral transmission likely occurs through cell-to-cell contact at virological synapses. Although the effects of PSGL-1 on HIV-1 cell-cell transmission have not been studied, given that PSGL-1 is recruited to sites of viral assembly by Gag, we speculate that it is likely present and inhibitory at the virological synapse. Interestingly, it has been shown that overexpression of PSGL-1 in cells also inhibits antibody binding to multiple cell surface receptors; the molecular mechanism has been suggested to be steric hindrance of antibody access to surface molecules, resulting from the extended structure and heavy O-glycosylation of the extracellular domains of PSGL-1.

An embodiment relates to the detrimental effect of PSGL-1 in hindering particle binding to target cells, one would expect viruses to evolve strategies to remove PSGL-1 from the virion surface. HIV-1 appears to use at least two viral accessary proteins, Vpu and Nef, to downregulate PSGL-1 from the surface (illustrated in FIG. 8A). Nevertheless, Vpu and Nef may antagonize PSGL-1 by different mechanisms. Vpu binds to PSGL-1 and induces its ubiquitination and degradation, whereas Nef did not reduce intracellular PSGL-1 levels; Nef may redirect PSGL-1 to intracellular compartments, resulting in the accumulation of the 70-80 kDa species (PSGL-1-70) (illustrated in FIG. 8B). Currently, the molecular identity of PSGL-1-70 is not known. PSGL-1-70 may be a PSGL-1 species with different posttranslational modification (e.g., . . . N-or O-linked glycosylation) relative to the larger species. The biological role of this PSGL-1-70 species is also not currently known. Although Nef is able to reduce cell-surface levels of PSGL-1, Vpu appears to play the dominant role in counteracting the antiviral effects of this inhibitory factor. In the case of CD43, both Vpu and Nef are able to downregulate cell-surface expression.

In another embodiment, in addition to disrupting the binding of HIV-1 virions to target cells, we observed that PSGL-1 expression in the virus-producer cell is also capable of interfering with the infectivity of another retrovirus—MLV—and the influenza A virus. We and others have provided evidence that HIV-1 antagonizes PSGL-1 through the activities of Vpu and Nef. Further work will be necessary to determine whether other retroviruses and non-retroviral enveloped viruses have also acquired defense mechanisms to counteract the road block imposed by PSGL-1.

An embodiment relates to a binding of the HIV envelope to the chemokine coreceptors triggers membrane fusion and signal transduction. The fusion process has been well characterized. A critical function of the chemokine coreceptor signalling in facilitating HIV infection of resting CD4 T cells. Static cortical actin in resting T cells represents a restriction, and HIV utilizes the Gαi-dependent signalling from the chemokine coreceptor CXCR4 to activate a cellular actin depolymerizing factor, cofilin, to overcome this restriction. HIV envelope-mediated cofilin activation and actin dynamics are important for a post entry process that leads to viral nuclear localization. Inhibition of HIV-mediated actin rearrangement markedly diminishes viral latent infection of resting T cells. Conversely, induction of active cofilin greatly facilitates it. Viral exploitation of cellular machinery in resting T cells, where chemokine receptor signaling becomes obligatory.

An embodiment relates to a most common method utilizes reporter cell lines based on the HIV LTR (Long Terminal Repeat) promoter. The early HIV gene product Tat amplifies expression from the LTR; however, there is a background transcriptional activity that is independent of Tat. Furthermore, LTR activity can be influenced by cellular activation states. Recently constructed a Rev-dependent expression vector, and as a test of this construct's functionality, integrated this vector into a continuous T cell line. This novel indicator cell has no measurable background signal, is not affected by elevated metabolic states, and yet responds robustly to the presence of HIV. The line is able to complete TCID50 assays in 3-5 days, and appears sensitive to both CCR5- and CXCR4-utilizing viruses.

An embodiment relates to an electron microscopy of rotary-shadowed PSGL-1 purified from human neutrophils indicated that it is a highly extended molecule with an extracellular domain that is-50 nm long. Both individual PSGL-1 molecules and rosettes composed of several molecules presumably attached at their transmembrane segments were observed. The extracellular domain of PSGL-1 has 318 residues, including a signal peptide from residues 1-18 and a propeptide from residues 19-41. PSGL-1 is a long, extended molecule and suggest that the P-selectin binding site is located near the N terminus, well above the membrane. This location may facilitate interactions of PSGL-1 with P-selectin under shear stress. P-selectin project its lectin domain well above the membrane to mediate optimal attachment of neutrophils under shear forces. The length of P-selectin may: (a) facilitate interactions with PSGL-1 on flowing neutrophils, and (b) increase the intermembrane distance where specific bonds form, minimizing contacts between the glycocalyces that result in cell-cell repulsion. PSGL-1 amino acid sequence of the transmembrane and cytoplasmic domains are well conserved and that, despite a poor conservation of PSGL-1 N-terminus, L- and P-selectin binding sites are evolutionary conserved. Functional assays reveal a critical role for post-translational modifications in regulating mammalian PSGL-1 interactions with selectins.

An embodiment relates to a PSGL-1 extracellular domain contains decameric repeats, which extend L- and P-selectin binding sites far above the plasma membrane. Decamers may play a role in regulating PSGL-1 interactions with selectins. Deletion of decamers abrogated soluble L-selectin binding and cell rolling on L-selectin, whereas their substitution partially reversed these diminutions. P-selectin-dependent interactions with PSGL-1 were less affected by decamer deletion. Decamers are required to stabilize L-selectin-dependent rolling. Importantly, adhesion assays performed on recombinant decamers demonstrated that they directly bind to E-selectin and promote slow rolling. The role of decamers is to extend PSGL-1 N terminus far above the cell surface to support and stabilize leukocyte rolling on L- or P-selectin. In addition, they function as a cell adhesion receptor, which supports approximately 80% of E-selectin-dependent rolling.

An embodiment relates to a selectins are carbohydrate-binding molecules involved in constitutive lymphocyte homing and chronic and acute inflammation processes. Th1 lymphocytes participate in cell-mediated inflammatory reactions, where the selectins play a role and predominate in delayed-type hypersensitivity (DTH) reactions of the skin. The glycosylated form of CD43 expressed in Th1 cells is a functional E-selectin-specific ligand in vitro. The relevance of CD43 as an E-selectin ligand in vitro and in vivo. Both PSGL-1 and CD43 are major E-selectin ligands and are likely to be important during leukocyte recruitment in the development of inflammatory reactions.

An embodiment relates to a glycosylation affects many essential T cell processes and is intrinsically controlled throughout the lifetime of a T cell. CD43 and CD45 are the two most abundant glycoproteins on the T cell surface and are decorated with O- and N-glycans. Global T cell glycosylation and specific glycosylation of CD43 and CD45 are modulated during thymocyte development and T cell activation; T cells control the type and abundance of glycans decorating CD43 and CD45 by regulating expression of glycosyltransferases and glycosidases. Additionally, T cells regulate glycosylation of CD45 by expressing alternatively spliced isoforms of CD45 that have different glycan attachment sites. The glycophenotype of CD43 and CD45 on T cells influences how T cells interact with the extracellular environment, including how T cells interact with endogenous lectins. The CD43 expressed on activated T cells functions as an E-selectin ligand and thereby mediates T cell migration to inflamed sites, in collaboration with PSGL-1.

In an embodiment, HIV-1 infection, or expression of either Vpu or Nef, downregulates PSGL-1 from the cell surface; expression of Vpu appears to be primarily responsible for enabling the virus to partially escape PSGL-1-mediated restriction. PSGL-1 inhibits the infectivity of other viruses such as murine leukemia virus and influenza A virus. PSGL-1 is a broad-spectrum antiviral host factor with a novel mechanism of action.

METHODS

Cells and Viruses

Peripheral blood buffy coats from HIV-1-negative adults were purchased from the New York Blood Center or received from the NIH Blood Bank. CD4+ T cells were isolated by negative selection using the Dynabeads Untouched magnetic separation kit (Invitrogen) or as previously described. CD4+ T cells were cultured in RPMI 1640 plus 10% fetal bovine serum (FBS) and 1× penicillin-streptomycin (Invitrogen). Resting CD4 T cells were activated by culturing in PHA (2 µg/ml) plus IL-2 (2 ng/ml) (PepTech). HEK293T cells (ATCC) and HeLaJC.53 cells (kindly provided by Dr. David Kabat) were maintained in Dulbecco-modified Eagle's medium (DMEM) (Invitrogen) containing 10% FBS and 1× penicillin-streptomycin (Invitrogen). PSGL-1-HeLaJC53 and Empty-HeLaJC53 cells were cultured in DMEM supplemented with 10% FBS and 550 µg/ml hygromycin B (Invitrogen). TZM-bl cells (Dr. John C. Kappes, and Dr. Xiaoyun Wu were obtained through the NIH AIDS Reagent Program, Division of AIDS, NIAID, NIH. TZM-bl cells were cultured in DMEM containing 10% FBS and 1× penicillin-streptomycin (Invitrogen). Jurkat cells (NIH AIDS Reagent Program) were cultured in RPMI 1640 supplemented with 2 mM L-glutamine. 10% FBS and 1× penicillin-streptomycin (Invitrogen). HIV Rev-dependent GFP indicator cells Rev-A3R5-GFP (Virongy) were cultured in RPMI 1640 plus 10% FBS supplemented with 1 µg/ml G418 (Sigma-Aldrich) and 1 µg/ml puromycin (Sigma-Aldrich). A3R5.7 cells (NIH AIDS Reagent Program) were cultured in RPMI-1640 containing 10% FBS. 1% L-Glutamine, 1× penicillin-streptomycin, and 1 µg/mL G418 (Invitrogen). CEM-SS cells (NIH AIDS Reagent Program) were cultured in RPMI-1640 with 10% FBS. To construct PSGL-1-HeLaJC53 cells, HeLaJC.53 cells were seeded into a 6-well plate and cultured in DMEM with 10% FBS. Cells were transfected with 2 µg pCMV3-PSGL-1 or pCMV3-Empty DNA using Jetprime transfection reagent (Polyplus) as recommended by the manufacturer. Transfected cells were cultured and selected with DMEM containing 10% FBS and 550 µg/ml of hygromycin B (Invitrogen) to generate stably transfected cells.

Plasmids, Vectors, Transfection, and Virion Production and Purification

The infectious HIV-1 molecular clone pNL4-3, codon-optimized Vpu expression vector (pcDNA-Vphu). Nef expression vector (pNef-ER), and NL4-3 ΔVpu infectious molecular clone (pNL-U35) were obtained from the NIH AIDS Reagent Program, pCMV3-PSGL-1 and pCMV3-Empty vectors were obtained from Sinobiological, pRetroP-SGL-1-NT, pRetroPSGL-1-CT, and pRetroPSGL-1 were synthesized and cloned into pMSCVneo vector by GeneScript, pPSGL-1-3A, pPSGL-1-6A, pPSGL-1-C310A, pPSGL-1-ACT, and pPSGL-1(Wt) were kindly provided by Dr. Akira Ono, pPSGL-1ΔDR was kindly provided by Drs. Caroline Spertini and Olivier Spertini. pCMV3-CD43 was obtained from Sinobiological, pSV-ψ-MLV-env- was from NIH AIDS Reagent Program, pNLΔΨEny (gp160) and pHCMV-G expressing the HIV-1 Env and the vesicular stomatitis virus G glycoprotein, respectively, were described previously. The GFP-expressing retroviral vector pRetroQ-AcGFP1-N1 was obtained from Clontech, pNL4-3ΔNef was described previously. The env-defective pNL4-3 derivative pNL4-3/KFS was described previously.

The procedure for transfection of HEK293T cells to produce HIV-1 particles was described previously. For GFP reporter MLV particle assembly, pRetroQ-AcGFP1-N1 (0.5 µg), pSV-ψ-MLV-env-(0.375 µg), and pHCMV-G (0.125 µg) were co-transfected with either pCMV3-PSGL-1 or pCMV3-Empty vector (at indicated dosages) in a 6-well plate. Virus supernatants were collected at 48 hours post transfection. For transient transfection of HeLaJC.53 cells. 0.5 million cells were transfected with 2 µg of either pCMV3-Empty or pCMV-PSGL-1 using the transfection reagent Jetprime (Polyplus) as recommended by the manufacturer. Following transfection, cells were cultured for the indicated times until analysis. For the p24 release assay in HEK293T cells, cells were cotransfected with 1 µg of HIV-1 NL4-3 and indicated doses of pCMV3-PSGL-1 or pCMV3-Empty DNA using Lipofectamine 2000 (Invitrogen). Supernatant was collected at 48 hours post-transfection. To purify virions by ultracentrifugation, supernatants harvested from transfected HEK293T cells first filtered through a 0.45 µm filter, then concentrated by Vivaspin20 concentrator. Concentrated viruses were purified by ultra-speed centrifugation through a gradient of 6-18% OptiPrep solution (Sigma-Aldrich) (40.000 rpm for 2 hours, SW41Ti rotor from Beckman), followed by a second round of ultracentrifugation to pellet the virus (20,000 rpm for 1.5 hours, SW41Ti).

FACS Analysis

For PSGL-1 surface staining, 0.5-1 million cells were stained with anti-PSGL1 antibody (KPL-1) (BD Pharmingen) followed by staining with Alexa Fluor 488-conjugated goat anti-mouse secondary antibody (Invitrogen). For surface staining of infected blood resting CD4+ T cells, HIV-1 infection was done using 125 ng to 320 ng p24 gag equivalents of NLENG1-ES-IRES GPF reporter virus (pseudotyped with HIV-1 NL4-3 envelope) per million cells. Cells were washed and cultured in 10% FBS RPMI with IL-7 (2 ng/mL). On the indicated days, cells were harvested and stained at 4° C., for 30 min with AF687 anti-PSGL-1 antibody (KPL-1, BD Pharmingen) and analyzed by flow cytometry. For surface PSGL-1 staining of Jurkat, CEMSS, and A3R5.7 cells. 0.5 million cells were stained with FITC-conjugated anti-PSGL-1 antibody (Abcam) and analyzed by flow cytometry. For HIV-1-infected Jurkat T-cell surface staining. 0.5 million cells were infected with different volumes of HIV-1 NL4-3. At 3 days post infection, cells were stained with anti-PSGL-1 antibody [KPL-1] (BD Pharmingen), followed by staining with Alexa Fluor 488-conjugated goat anti-mouse secondary antibody (Invitrogen) and flow cytometry analysis. For HEK293T cells. 0.5 million cells were co-transfected with different dosages (1 μg to 4 μg) of HIV NL4-3 Vpu or HIV NL4-3 Nef, and 100 ng of pCMV3-PSGL-1 using Lipofectamine 2000 (Invitrogen). Cells were stained at 48 hours post-transfection with anti-PSGL-1 antibody [KPL-1] (BD Pharmingen), followed by staining with Alexa Fluor 488-conjugated goat anti-mouse secondary antibody (Invitrogen).

Western Blots

The following antibodies were from the NIH AIDS Reagent Program: anti-HIV-1 p24 monoclonal antibody (183-H12-5C), anti-HIV Env (16H3) antibody, anti-HIV-1 gp41 monoclonal antibody (2F5), anti-HIV-1 gp41 monoclonal antibody (10E8), and anti-HIV immune globulin (HIVIG). Cells or virus pellets were solubilized in lysis buffer containing 50 mM Tris-HCl (pH 7.4). 150 mM NaCl. 1 mM EDTA. 0.5% Triton X-100, and protease inhibitor cocktail (Roche Life Science. Basel, Switzerland) or LDS lysis buffer (Invitrogen).

Proteins were denatured by boiling in sample buffer and subjected to SDS-PAGE, transferred to PVDF or nitrocellulose membrane, and incubated overnight at 4° C., with one of the following primary antibodies: anti-PSGL-1 monoclonal antibody (clone KPL-1, BD Pharmingen) (1:1000 dilution): anti-PSGL-1 TC-2 monoclonal antibody (Abcam) (1:1000 dilution); anti-PSGL-1 polyclonal antibody (Abcam) (1:1000 dilution); anti-PSGL-1-C terminal polyclonal antibody (anti-PSGL-1 amino acid 350) to the C-terminus) (Abcam) (1 μg/ml): anti-GAPDH goat polyclonal antibody (Abcam) (1:1000 dilution); anti-CD45RA antibody (BD Biosciences); anti-HIV envelope antibodies (183-H12-5C, 16H3, 2F5), HIVIG, and anti-CD63 polyclonal antibody (System Biosciences) (1:1000 dilution). Membranes were then incubated with HRP-labeled goat anti-mouse IgG (KPL) (1:2500 dilution) or anti-rabbit IgG (Cell Signaling) (1:2000 dilution) for 60) min at room temperature. Chemiluminescence signal was detected by using West Pico or West Femto chemiluminescence reagent (Thermo Fisher Scientific). Images were captured with a CCD camera (Fluo-rChem 9900 Imaging Systems) (Alpha Innotech). Protein bands were also quantified using Imagelab-Chemidoc (Bio-Rad Laboratories, France). On some occasions, western blot was also performed using infrared imaging (Odyssey infrared imager. LI-cor Biosciences) with IRDye goat anti-mouse or rabbit 680 or 800 cw labeled antibodies (Li-corBiosciences) (1:5000 diluted in blocking buffer) for 1 h at 4° C. The blots were washed three times for 15 minutes and scanned with Odyssey Infrared Imager (Li-cor Biosciences). The ratios of gp120/p24 and gp160/p24 were quantified in virions, and the ratio of gp120/gp160 and expression of PSGL-1 were quantified in cell and virus fractions. To quantify virus release efficiency. HEK293T cells were transfected with the indicated plasmids (WT pNL4-3, pNL43ΔVpu, or pNL43ΔNef) in the absence or presence of PSGL-1 expression vector using Lipofectamine 2000 (Invitrogen) or polyethylenimine (PEI) transfection reagent (Sigma-Aldrich). At 30 to 48 hours after the addition of DNA, virus-containing supernatant was harvested for p24 ELISA, or filtered and pelleted in an ultracentrifuge for analysis. The viral release efficiency (VRE) was calculated as the amount of virion-associated Gag as a fraction of total (cell- and virion-associated) Gag quantified from Western blot analysis.

p24 ELISA

HIV-1 p24 released into the cell culture supernatant was detected by an in-house p24 ELISA kit. Briefly, microtiter plates (Sigma-Aldrich) were coated with anti-HIV-1 p24 monoclonal antibody (183-H12-5C) (NIH AIDS Reagent Program). Samples were incubated for 2 hours at 37° C., followed by washing and incubating with biotinylated anti-HIV immune globulin (HIVIG) (NIH AIDS Reagent Program) for 1 hour at 37° C. Plates were then washed and incubated with avidinperoxidase conjugate (R&D Systems) for 1 hour at 37° C., followed by washing and incubating with tetramethylbenzidine (TMB) substrate. Plates were kinetically read using an ELx808 automatic microplate reader (Bio-Tek Instruments) at 630 nm.

Viral Entry Assay (BLAM Assay)

The viral entry assay was performed as previously described. Briefly, viruses were generated by co-transfection of HEK293T cells with three plasmids: pNL4-3, pAdvantage (Promega) and pCMV4-3BlaM-Vpr (kindly provided by Dr. Warner C. Greene) (at a ratio of 6:1:2). Supernatant was harvested at 48 hours post-transfection, concentrated, and then used for infection as suggested. Flow cytometry was performed using a Becton Dickinson LSR II (Becton Dickinson). B-lactamase and CCF2 measurements were performed using a 407-nm violet laser with emission filters of 525/50 nm (green fluorescence) and 440/40 nm (blue fluorescence), respectively. Green and blue emission spectra were separated using a 505LP dichroic mirror. The UV laser was turned off during the analysis. Data analysis was performed using FlowJo software (FlowJo).

Viral Attachment Assay

Virion particles produced in the presence of PSGL-1 or the empty vector were incubated with HelaJC53 cells (pre-chilled at 4° C., for 1 hour) at 4° C., for 2 hours. The cells were then washed extensively (5 times) with cold PBS buffer and then lysed with LDS lysis buffer (Invitrogen) for analysis by Western blot.

Infectivity Assays

For flow cytometry-based infectivity assay, virus particles were produced in HEK293T cells by co-transfection with pNL4-3, pNL4-3ΔVpu, or pNL4-3ΔNef with pCMV3-PSGL-1, pCMVCD43, or pCMV3-Empty, or by cotransfection with pNL4-3/KFS, pHCMV-G, and pCMV3-PSGL-1 or pCMV3-Empty vector (using the indicated plasmid inputs) in a 6-well plate with Lipofectamine 2000 (Invitrogen). Viral particles were also produced in CEM-SS cells by electroporation. Briefly, CEM-SS cells (2 millions) were electroporated with pNL4-3 (2 μg) plus 400 ng of pCMV3-PSGL-1 or pCMV3-Empty using a T cell electroporation kit (Lonza). Viral particles were harvested at 3 days post electroporation. Rev-A3R5-GFP cells were infected with each of the indicated viruses (0.2-0.5 million cells/infection). The cells were then washed and cultured in fresh media. Flow cytometry analysis of GFP expression was performed on the indicated days. The percentage of GFP+ cells was quantified.

For luciferase-based, single-cycle infectivity assays, RT-normalized virus stocks were used to infect the CD4+/CXCR4+/CCR5+HeLa derivative TZM-bl. This indicator cell line contains integrated copies of the B-galactosidase and luciferase genes under the control of the HIV-1 LTR. Infection efficiency was determined by measuring luciferase activity 2 days post-infection. For infectivity assays in HeLa JC53-PSGL-1 and HeLa-JC53-empty cell lines, the cells were seeded in 6-well plates at a density of 0.2×106/well 24 hours prior to infection. Cells were infected with the indicated p24 equivalents of either WT NL4-3. NL43ΔVpu, or NL43ΔNef. Viral replication was quantified by virion p24 released into the medium by p24 ELISA. For MLV (murine leukemia virus) virion infectivity. MLV-GFP reporter virus was assembled by co-transfecting HEK293T cells (in 6-well plate) with pSV-Ψ-MLV-env-(0.375 μg), pRetroQAcGFP1-N1 (0.5 μg), pHCMV-G (0.125 μg), and pCMV3-PSGL1 or an empty vector at the indicated dosages. An equal amount of DNA was used all transfections. Viral supernatants were harvested 48 h post transfection and used to infect HEK293T cells for 6 hours in the presence of Infectin (Virongy, Manassas, VA). Cells were washed to remove virus and Infectin, and cultured for 48 hours for flowcytometry analyses.

To determine the effect of PSGL-1 on influenza A virus replication, HEK293T and MDCK cells were co-cultured at approximately 70% confluence in 6-well plates and transfected with either empty vector or pCMV3-PSGL-1 (both vectors at 1.0 or 3.0 μg), together with an eight plasmid influenza A/WSN/33 reverse genetics system (RGS) system (1.0 μg of each plasmid). Transfection reaction was prepared with PEI (polyethylenimine). Culture supernatants were collected at 16 and 24 h post-transfection and titrated in MDCK cells to determine end-point titers (TCID50 per ml). shRNA Knockdown of PSGL-1

Lentiviral vectors carrying shRNAs against PSGL-1 or non-target control (NTC) (Sigma MISSION shRNA. PSGL-1 TRCN0000436811 or shRNA NTC) were purchased from Sigma. Virion particles were assembled by cotransfecting HEK293T cells with 0.5 μg of pHCMV-G. 1.5 μg pCMV-AR8.2, and 2 μg of lentiviral vectors using Lipofectamine 3000 (Invitrogen). Supernatant was collected at 48 hours post co-transfection, and then filtered through 0.45 um filter. Virion particles were used to transduce Jurkat T cells for 6 hours. Cells were then washed twice and cultured in fresh media for 3 days, and then selected in puromycin (4 μg/ml) for one to two weeks. PSGL-1 knockdown was confirmed by surface staining with an anti-PSGL-1 antibody (KPL-1) (BD Pharmingen) followed by staining with Alexa Fluor 488-conjugated goat anti-mouse secondary antibody (Invitrogen). PSGPL-1 knockdown or NTC control cells (2×10$^6$) were also transfected with 2 μg of HIV-1(NL4-3) DNA by electroporation using a T cell electroporation kit (Lonza). Viruses were harvested and used for the infection of Rev-A3R5-GFP cells (20 ng p24 per infection). Flow cytometry analysis of GFP expression was performed on the indicated days. Lentiviral vector-mediated ShRNA knockdown of PSGL-1 in primary CD4 T-cells was performed as described previously. Briefly, blood resting CD4 T cells were purified by negative depletion, transiently stimulated with anti-CD3/CD28 beads (1-2 beads per cell) for 12 hours, and then transduced with the lentiviral vectors carrying shRNAs against PSGL-1 or non-target control (NTC) (Sigma MISSION shRNA. PSGL-1 TRCN0000436811 or shRNA NTC). Following transduction, the beads were removed at 12 hours, and cells were cultured for 3 days, and then analyzed from surface PSGL-1 expression. Cells were also subsequently transfected with HIV-1(NL4-3) DNA by electroporation using a T-cell electroporation kit (Lonza). HIV-1 viral replication was monitored by harvesting cell culture supernatant, and HIV p24 was detected by an in-house p24 ELISA kit.

The following examples are offered for illustrative purposes only and are not intended to limit the scope of the present invention in any way. Indeed, various modifications of the invention in addition to those shown and described herein will become apparent to those skilled in the art from the foregoing description and fall within the scope of the appended claims.

Example 1: PSGL-1 is Expressed on Primary CD4 T Cells and Elicits Anti-HIV Activity in HeLa JC.53 Cells PSGL-1 is expressed on primary CD4 T cells and elicits anti-HIV activity in HeLa JC.53 cells. To study the mechanisms of PSGL-1-mediated restriction of HIV-1 replication, we first quantified PSGL-1 expression on both primary blood CD4 T cells and transformed T-cell lines. We observed that human blood resting CD4 T cells express high levels of PSGL-1, and T-cell activation (IL-2 plus PHA) down-regulates PSGL-1 (illustrated in FIG. 1A), while transformed CD4 T-cell lines express low (e.g. Jurkat) to undetectable (e.g. CEM-SS) levels of PSGL-1 (illustrated in FIG. 1B). Transformed, non-T cell lines such as HeLa and 293T do not express detectable levels of PSGL-1 (illustrated in FIG. 6). Nevertheless, resting T cells can be latently infected and support low levels of HIV replication in the presence of cytokines such as IL-7.

It is possible that HIV infection of primary resting CD4 T cells may downregulate PSGL-1 as seen in transformed T-cell lines (illustrated in FIG. 7). We followed HIV-1 infection of primary resting CD4 T cells, and found that HIV-1 infection of IL-7-treated blood resting CD4 T cells downregulates PSGL-1 exclusively in the HIV-1-positive cell population (illustrated in FIGS. 1C and 1D). HIV-1-mediated downregulation of PSGL-1 occurred both in the memory and naïve T-cell subsets (illustrated in FIG. 1E).

Vpu has been identified as a viral factor that mediates intracellular PSGL-1 degradation. However, both Vpu and Nef are known broad-spectrum modulators of cell-surface receptors. Thus, we also examined the role Nef in HIV-mediated PSGL-1 downregulation, and observed a dose-dependent downmodulation of surface PSGL-1 levels by both Vpu and Nef, consistent with previous reports (illustrated in FIG. 8A). However, when the levels of intracellular PSGL-1 were examined (illustrated in FIG. 8B). Vpu but not Nef was found to cause a decrease in total intracellular PSGL-1. Interestingly, Nef induced an intracellular accumulation of the 70-80 kDa species of PSGL-1 (PSGL-1-70) (illustrated in FIG. 8B).

To confirm the anti-HIV activity of PSGL-1, we established PSGL-1-stably transfected HeLa JC.53 cells (HeLaJC53-PSGL-1) (illustrated in FIG. 1F). WT HIV-1 and HIVΔVpu derivatives were produced in HEK293T cells in the absence of PSGL-1, and then used to infect HeLaJC53-PSGL-1 or control HeLaJC53-Empty vector-transfected cells, using p24-normalized inocula. At all 3 HIV-1 inputs. PSGL-1 inhibited spreading HIV infection over a 14-day time course (illustrated in FIG. 1F). In addition. PSGL-1 displayed a stronger inhibition of HIVΔVpu than of WT: even at the highest HIV-1 input used (32 ng p24), no spreading viral replication was detected from HIVΔVpu in HeLaJC53-PSGL-1 cells, whereas WT viral replication was more modestly inhibited (illustrated in FIG. 1F), consistent with previous studies from transient transfection of PSGL-1 into virus-producing cells. These results confirmed that PSGL-1 restricts spreading HIV infection and Vpu can partially antagonize this restriction.

Given the observed differences between Vpu and Nef in downregulating PSGL-1 (illustrated in FIG. 8A), we further compared the relative activity of Vpu and Nef in antagonizing PSGL-1. We found that although both Vpu and Nef can downregulate PSGL-1 from the cell surface. Vpu plays the predominant role in antagonizing PSGL-1: the 50% inhibitory dose (IC50) of PSGL-1 for WT HIV-1 (~2.7 ng) is approximately ten-fold higher than the IC50 of PSGL-1 for HIVΔVpu (~0.29 ng). Thus, deletion of Vpu led to a heightened sensitivity to PSGL-1 restriction. In contrast, there was only a slight difference in PSGL-1 IC50 between WT and ΔNef HIV-1 (illustrated in FIG. 9).

Example 2: PSGL-1 does not Block Viral Release but Inactivates Virion Infectivity PSGL-1 does not block viral release but inactivates virion infectivity. PSGL-1 has been suggested to block viral reverse transcription early post-infection, and inactivate virion infectivity late in the replication cycle. Thus, we examined the role of PSGL-1 in a single HIV-1 replication cycle. We infected PSGL-1-stably transfected HeLa JC.53 cells (HeLaJC53-PSGL-1) or the control cells (HeLaJC53-Vector) with an HIV-1 Env-pseudotyped, single-cycle virus. HIV (gp160) (illustrated in FIG. 2A). We observed no inhibition of HIV-1 infection in a single cycle, as judged by the release of virion-associated p24 from the infected cells (illustrated in FIG. 2A). Thus, in the system. PSGL-1 did not block any step in the viral replication cycle up to and including virion assembly and release. To confirm this result, co-transfected HEK293T cells with HIV(NL4-3) proviral DNA (1 μg) plus PSGL-1 expression vector at varying inputs from 50 to 400 ng (illustrated in FIG. 2B).

We observed small effects of PSGL-1 expression on HIV-1 virion release, from slight enhancement at low doses (below: 100 ng) to no effect at high doses (200 and 400 ng). When normalized to the levels of intracellular Gag. PSGL-1 did not inhibit virion release at any dose tested (illustrated in FIG. 2C to 2E). Next, we quantified the infectivity of the released virions on target CD4 T cells, using a highly stringent Rev-dependent indicator cell line. Rev-A3R5-GFP, that does not respond to non-infectious HIV stimuli as do LTR-based reporter cell lines. As shown in FIG. 2F, we observed that PSGL-1 expression in the virus-producer cell almost completely abolished the infectivity of released virions at PSGL-1 vector doses higher than 50 ng (illustrated in FIG. 2F). PSGL-1 partially restricted HIV-1 infectivity at inputs as low as 0.5 ng (PSGL-1-to-HIV-1 DNA ratio. 1:2000), and there was a dose-dependent inactivation of HIV-1 at PSGL-1 vector doses from 0.5 to 50 ng (illustrated in FIG. 2G).

The potent inactivation of HIV-1 infectivity was confirmed by quantifying HIV infectivity in the HeLa cell-derived TZM-bl cell line (illustrated in FIG. 10), and by following HIV-1 spreading infection in A3R5.7 CD4 T cells (illustrated in FIG. 11). Interestingly, we also observed that the infectivity of HIV-1 virions bearing VSV-G was significantly inhibited by PSGL-1 expression in the virus-producer cell (illustrated in FIG. 2H and FIG. 12). Together, these results demonstrate that the presence of PSGL-1 in producer cells inactivates the infectivity of released virions. To corroborate these results, we also produced virions from a human CD4 T cell. CEM-SS. Introduction of PSGL-1 into CEM-SS also inactivated the infectivity of progeny virions released, consistent with the results observed in HEK293T producer cells (illustrated in FIG. 13).

To further examine the role of endogenous PSGL-1 in virus replication, we performed lentiviral vector-mediated stable shRNA knockdown of PSGL-1 in Jurkat T cells, which express low levels of PSGL-1 (illustrated in FIG. 1B). Following selection, we established a stable pool of Jurkat cells with reduced expression of surface PSGL-1 (shRNA PSGL-1) (illustrated in FIG. 2I). The PSGL-1 knockdown cells, along with the shRNA non-target control cells (shRNA NTC), were used as the virion producer cells to test the effects of PSGL-1 knockdown on progeny virion infectivity. Cells were directly transfected with HIV-1 DNA by electroporation to produce virions. Following DNA delivery, viral replication in the PSGL-1 knockdown cells was evaluated by measuring extracellular p24. We observed a 4-5 fold enhancement of HIV-1 replication in the knockdown cells at day 3 and 4 (illustrated in FIG. 2J). To confirm that this enhancement was mediated by increased virion infectivity, viral particles were harvested at 48 hours, and p24-normalized released virions were used to infect Rev-A3R5-GFP indicator cells. As shown in FIG. 2K, we observed enhanced infectivity for virions released from the PSGL-1 knockdown cells. These results are in agreement with the PSGL-1 co-expression experiments (illustrated in FIG. 2F), demonstrating that the presence of PSGL-1 in virus-producer cells, even at low levels, such as those present endogenously in Jurkat, can inhibit virion infectivity.

The levels of PSGL-1 on Jurkat are comparable with those on activated primary blood CD4 T cells (illustrated in FIGS. 1A and 1B). To corroborate the PSGL-1 knockdown results observed in Jurkat cells, we also performed similar lentiviral vector-mediated shRNA knockdown of PSGL-1 in pre-activated primary CD4 T cells, and observed a similar enhancement of HIV-1 replication (illustrated in FIG. 14).

Example 3: PSGL-1 Blocks Virion Attachment to Target Cells

PSGL-1 blocks virion attachment to target cells. To examine whether PSGL-1 expression in the producer cell, and its incorporation into virus particles (illustrated in FIG. 15), inhibits virus entry, we performed the beta-lactamase (BLAM)-based virus entry assay (illustrated in FIG. 3A). Rapid assay allowing the detection of HIV-1 virion fusion to biologically relevant target cells, including primary CD4(+) T lymphocytes. It is based on the incorporation of beta-lactamase-Vpr chimeric proteins (BlaM-Vpr) into HIV-1 virions and their subsequent delivery into the cytoplasm of target cells as a result of virion fusion. This transfer is then detected by enzymatic cleavage of the CCF2 dye, a fluorescent substrate of beta-lactamase (BlaM), loaded in the target cells. BlaM cleaves the beta-lactam ring in CCF2, changing its fluorescence emission spectrum from green (520) nm) to blue (447 nm) and thereby allowing fusion to be detected by fluorescence microscopy, flow cytometry, or UV photometry.

The HIV-1 entry inhibitor AMD3100 provided a positive control for entry inhibition. The results indicated that PSGL-1-imprinted virus particles were severely impaired in their ability to enter target cells (illustrated in FIG. 3A). We further performed a virion attachment assay, and observed that virions from PSGL-1-expressing cells were impaired in their ability to attach to susceptible target cells (illustrated in FIG. 3B). Because PSGL-1 expression in the virus-producer cell also inhibits the infectivity of VSV-G-pseudotyped HIV-1 (illustrated in FIG. 2H and FIG. 12), we investigated the effect of PSGL-1 on HIV-1 Env and VSV-G incorporation into virion particles. Whereas we observed that expression of PSGL-1 in the virus-producer cell reduced levels of HIV-1 Env on virions, the levels of the VSV-G in virions were not reduced by PSGL-1 expression (illustrated in FIG. 16).

We also performed a virion attachment assay, and observed that PSGL-1-imprinted virions bearing either VSV-G or HIV-1 Env were impaired in their ability to attach to target cells (illustrated in FIG. 3B). These results suggest that the presence of PSGL-1 on virus particles may structurally hinder viral envelope interaction with target cells. We next tested whether PSGL-1 inhibition of viral attachment to cells is dependent on the presence of viral envelope proteins. HIV-1 particles devoid of any viral envelope glycoproteins were assembled by transfection of the Env(−) pNL4-3/KFS molecular clone in the presence or absence of the PSGL-1 vector. Virus particles were then used to perform the attachment assay. As shown in FIG. 3C, we observed that PSGL-1-imprinted. Env-negative particles were also impaired in their ability to attach to target cells. These results demonstrate that PSGL-1 can inhibit virion attachment to cells in an envelope glycoprotein-independent manner.

Example 4: The Extracellular, N-Terminal Domain of PSGL-1 is Required for Blocking HIV-1 Infectivity The extracellular, N-terminal domain of PSGL-1 is required for blocking HIV-1 infectivity. Structurally, PSGL-1 has a relatively rigid and elongated extracellular domain that extends nearly 60 nm from the cell surface. To test the hypothesis that the presence of PSGL-1 on virus particles may sterically hinder the binding of particles to target cells (illustrated in FIG. 4A), we performed deletion mutagenesis of PSGL-1 domains. The extracellular N-terminal or intracellular C-terminal domains of PSGL-1 were deleted to generate PSGL-1-CT or PSGL-1-NT (illustrated in FIG. 4B, sequence no. 3 and 2 respectively). Vectors expressing PSGL-1 (pRetroPSGL-1), PSGL-1-CT (pRetroPSGL-1-CT) or PSGL-1-NT (pRetroPSGL-1-NT) were co-transfected with HIV(NL4-3) DNA into HEK293T cells to produce viral particles (illustrated in FIG. 17).

Cellular expression and virion incorporation of PSGL-1 mutants were confirmed by surface staining and western blots (illustrated in FIG. 17). Virion infectivity was subsequently quantified in Rev-A3R5-GFP cells. As shown in FIG. 4B, deletion of most of the intracellular C-terminal domain had minimal effect on PSGL-1's ability to restrict HIV-1, whereas truncation of the extracellular N-terminal domain largely abolished the restrictive phenotype. These results demonstrate that the extracellular N-terminus of PSGL-1 is required for its anti-HIV-1 activity. To confirm and extend these results, we tested an additional PSGL-1 N-terminal deletion mutant, pPSGL-1ΔDR, in which the decameric repeats (DR) were removed: a large structural part of PSGL-1's extracellular domain consists of 14-16 decamers, which are characterized by repeated stretches of 10) amino acids with numerous O-glycosylated threonines (30%) and prolines (10%). DR plays a pivotal role in elongating and strengthening the protein backbone to extend the N-terminal selectin-binding sites far away from the cell surface to support and stabilize leukocyte rolling on L- or P-selectin. Indeed, when DR was deleted from the N-terminus, the anti-HIV activity of PSGL-1 was also abolished (illustrated in FIG. 18).

We further tested a panel of previously studied PSGL-1 mutants (illustrated in FIG. 4C and FIG. 17). PSGL-1-ACT (sequence no. 8) has the cytoplasmic tail completely removed, whereas PSGL-1-3A (sequence no. 5) and PSGL-1-6A (sequence no. 6) have multiple amino acid changes in the cytoplasmic tail: PSGL-1-3A has the three juxtamembrane basic residues changed to alanine, and PSGL-1-6A (sequence no. 6) has the six acidic residues near the C-terminus replaced with alanine (illustrated in FIG. 4C).

An additional mutant. PSGL-1-C310A (sequence no. 7), abolishes PSGL-1 dimerization. Given that the cytoplasmic tail mutations may decrease virion incorporation of PSGL-1, we used a high amount of the mutant PSGL-1 DNA (500 ng) to co-transfect with HIV-1 DNA (1 μg) to ensure that even with a lower level of virion incorporation of PSGL-1, it would still be sufficient to confer a restrictive phenotype. Using this high PSGL-1 dose, we were able to demonstrate that all the PSGL-1 C-terminal mutants, along with the dimerization mutant C310A (sequence no. 7), maintained their capacity to restrict HIV-1 (illustrated in FIG. 4C), confirming that the N-terminal domain of PSGL-1 is primarily responsible for its anti-HIV activity, and PSGL-1 dimerization is not required. Although deletion of the C-terminal domain of PSGL-1 did not abolish its anti-HIV activity (illustrated in FIG. 4C), the complete removal of the C-terminus of PSGL-1 has been reported to reduce PSGL-1 coclustering with Gag, and thus may affect its ability to be incorporated into HIV-1 particles and inhibit viral infection. To investigate this possibility, we performed a side-by-side, dose-response comparison of the ability of WT PSGL-1 and PSGL-1-ACT to inactivate virion infectivity. As shown in FIG. 4D, the complete removal of the C-terminal cytoplasmic tail of PSGL-1 (PSGL-1-ACT, sequence no. 8) led to a 10-fold reduction in PSGL-1's anti-HIV activity. These results demonstrate that although the C-terminus is not absolutely required, it can affect PSGL-1's anti-HIV capacity, likely by inducing coclustering with Gag to promote virion packaging.

Example 5: PSGL-1 is a Broad-Spectrum Antiviral Host Factor

PSGL-1 is a broad-spectrum antiviral host factor. Given that the PSGL-1 intracellular domain deletion mutant, PSGL-1-ACT, effectively blocks HIV-1 infectivity in the absence of coclustering with HIV-1 Gag, it is possible that PSGL-1 does not rely on specific interactions with an HIV-1 protein to restrict particle infectivity. Indeed. PSGL-1 inhibition of viral attachment to cells is independent of the presence of viral envelope protein (illustrated in FIG. 3C). The mere presence of the long extracellular domain of PSGL-1 on the surface of virus particles may be sufficient to interfere with particle binding to target cells (illustrated in FIG. 4A). Thus, PSGL-1 may possess a broad-spectrum antiviral activity that extends beyond HIV-1. To test this hypothesis, we produced VSV-G-pseudotyped murine leukemia virus (MLV) particles in the presence of PSGL-1. Although PSGL-1 expression did not block MLV particle production (illustrated in FIG. 5A), it severely inactivated MLV infectivity (illustrated in FIG. 5B). Finally, we tested the ability of PSGL-1 to disrupt the infectivity of a non-retroviral enveloped virus, influenza A virus. Eight vectors expressing each of the segments of the influenza A/WSN/33 (H1N1) genome were cotransfected with the PSGL-1 vector into HEK293T-MDCK co-cultured cells. Viral particles were harvested at 16- and 24-hours post-transfection, and virion infectivity was quantified by TCID50 assay. As shown in FIG. 5C, at 16 hours, cotransfection with 1 μg of PSGL-1 led to a 100-fold reduction in the infectious titer from released virions, whereas with 3 μg of PSGL-1, the viral titer was reduced over 8,000-fold. These results demonstrate that PSGL-1 has a broad antiviral activity.

Example 6: PSGL-1-Related Selectin Ligand CD43 Also Restricts HIV Infectivity PSGL-1-related selectin ligand CD43 also restricts HIV infectivity. Given that PSGL-1 restriction of HIV infectivity does not require its dimerization (illustrated in FIG. 4C), we speculated that monomeric PSGL-1 and related selectin ligands may also inactivate virion infectivity. Therefore, we further tested CD43, a monomeric glycoprotein that, like PSGL-1, binds E-selectin. Similar to PSGL-1, CD43 is a mucin-like protein that is heavily glycosylated. CD43 is also bulky and protrudes 45 nm from the cell surface. The glycosylated form of CD43 is expressed in Th1 T cells and functions as an E-selectin-specific ligand; CD43 collaborates with PSGL-1 to mediate E-selectin-dependent T-cell migration. We co-transfected HEK293T cells with HIV (NL4-3) proviral DNA (1 μg) plus a CD43 expression vector at varying inputs from 0.5 to 400 ng (illustrated in FIG. 19). Next, we quantified the infectivity of the released virions on Rev-A3R5-GFP cells. We observed that CD43 almost completely abolished the infectivity of released virions at CD43 vector doses higher than 50 ng (illustrated in FIG. 19A). CD43 partially restricted HIV-1 infectivity at inputs as low as 0.5 to 1 ng, and there was a dose-dependent inactivation of HIV-1 at CD43 vector doses from 0.5 to 50 ng. The IC50 of CD43 for inhibiting HIV-1 is 2.69 ng, similar to that of PSGL-1 (~2.7 ng) (illustrated in FIG. 19B). These results suggest that the shared structural properties (extensive glycosylation, 40-60 nm protrusion from surface, and rigid, rod-like structure) of selectin ligands may pose a broad issue for viruses if incorporated and displayed on virion surfaces.

The embodiments describe a new approach to producing vaccines or broad spectrum anti-viral products comprising live attenuated, inactivated, or non-infectious virion particles, such as HIV particles. Other embodiments are also within the scope of the following claims.

REFERENCES

1. Sako D. et al. (1993) Expression cloning of a functional glycoprotein ligand for P-selectin. Cell 75(6): 1179-1186.
2. Guyer D A. et al. (1996) P-selectin glycoprotein ligand-1 (PSGL-1) is a ligand for L-selectin in neutrophil aggregation. Blood 88(7):2415-2421.
3. Goetz D J. et al. (1997) Isolated P-selectin glycoprotein ligand-1 dynamic adhesion to P- and E-selectin. J Cell Biol 137(2):509-519.
4. Laszik Z. et al. (1996) P-selectin glycoprotein ligand-1 is broadly expressed in cells of myeloid, lymphoid, and dendritic lineage and in some nonhematopoietic cells. Blood 88(8):3010-3021.
5. Fujimoto T T. et al. (1996) Expression and functional characterization of the P-selectin glycoprotein ligand-1 in various cells. Int J Hematol 64(3-4):231-239.
6. Somers W S, Tang J, Shaw G D, & Camphausen R T (2000) Insights into the molecular basis of leukocyte tethering and rolling revealed by structures of P- and E-selectin bound to SLe(X) and PSGL-1. Cell 103(3): 467-479.
7. Almulki L. et al. (2009) Surprising up-regulation of P-selectin glycoprotein ligand-1 (PSGL-1) in endotoxin-induced uveitis. FASEB J 23(3): 929-939.
8. Xu H. et al. (2004) Recruitment of IFN-gamma-producing (Th1-like) cells into the inflamed retina in vivo is preferentially regulated by P-selectin glycoprotein ligand 1:P/E-selectin interactions. J Immunol 172(5):3215-3224.
9. Schumacher A. et al. (2005) P-selectin glycoprotein ligand-1 (PSGL-1) is up-regulated on leucocytes from patients with chronic obstructive pulmonary disease. Clin Exp Immunol 142(2):370-376.
10. Nishimura Y. et al. (2009) Human P-selectin glycoprotein ligand-1 is a functional receptor for enterovirus 71. Nat Med 15(7): 794-797.
11. Tinoco R. et al. (2016) PSGL-1 Is an Immune Checkpoint Regulator that Promotes T Cell Exhaustion. Immunity 44(5): 1190-1203.
12. Liu Y. et al. (2019) Proteomic profiling of HIV-1 infection of human CD4(+) T cells identifies PSGL-1 as an HIV restriction factor. Nat Microbiol 4(5):813-825.
13. Grover J R, Veatch S L, & Ono A (2015) Basic motifs target PSGL-1, CD43, and CD44 to plasma membrane sites where HIV-1 assembles. J Virol 89(1):454-467.

What is claimed is:

1. A method comprising:
    taking P-selectin glycoprotein ligand-1 (PSGL-1) or a mutant thereof comprising an extracellular N-terminal domain (NT) comprising at least one decameric repeat (DR) region, and a transmembrane (TM) region, wherein the DR region comprises at least one proline and more than one O-glycosylated threonine, wherein the mutant exhibits an antiviral activity;
    co-expressing a retroviral vector of a retrovirus and an expression vector comprising the PSGL-1 or the mutant thereof in a virus-producing cell (VPC) such that the PSGL-1 or the mutant thereof is incorporated into a viral particle during a virion assembly and expressed on a surface of virions produced due to introduction of the retroviral vector in the VPC;
    wherein presence of the PSGL-1 or the mutant thereof on the surface of the virions blocks binding of the virions to its cognate receptor to inactivate a viral infection of the retrovirus; and
    wherein the VPC comprises a cell line of a human.

2. The method of claim 1, wherein the DR region is configured to block the viral infection.

3. The method of claim 1, wherein the PSGL-1 or the mutant thereof is configured to block the viral infection by structurally hindering the virions to bind to a target cell.

4. The method of claim 1, wherein the retrovirus comprises a human immunodeficiency virus (HIV), or a murine leukemia virus.

5. The method of claim 1, wherein inactivation of infectivity of the virions is independent of an envelope glycoprotein (Env-1) of the VPC.

6. The method of claim 1, wherein the viral infection comprises a human immunodeficiency virus (HIV) or a murine leukemia virus.

7. The method of claim 1, wherein 1 µg of the PSGL-1 or the mutant thereof produces a 100-fold decrease in anti-viral activity of the virions released from the VPC.

8. The method of claim 1, wherein 3 µg of the PSGL-1 or the mutant thereof produces about 8000-fold decrease in anti-viral activity of the virions released from the VPC.

9. The method of claim 1, wherein the PSGL-1 or the mutant thereof is configured to disrupt Env-1 of the retrovirus.

10. The method of claim 1, wherein the mutant comprises a PSGL-1 C-terminal mutant, a dimerization mutant at C310A, a PSGL-1-3A, or a PSGL-1-6A.

11. The method of claim 1, wherein the expression vector is configured to block the viral infection in a dose dependent manner.

12. The method of claim 11, wherein a dose of the expression vector is in a range about 0.5 ng to about 500 ng.

13. The method of claim 1, wherein the method comprises PSGL-1.

14. The method of claim 13, wherein the vector and the expression vector are in a ratio of about 0.05:1.

15. A method comprising:
taking P-selectin glycoprotein ligand-1 (PSGL-1);
co-transfecting a retroviral vector of a retrovirus and an expression vector comprising the PSGL-1 in a virus-producing cell (VPC) comprising a cell line of a human;
expressing the PSGL-1 on a surface of virions produced from the VPC such that the PSGL-1 is incorporated into a viral particle during a virion assembly and expressed on the surface of the virions produced due to introduction of the retroviral vector in the VPC; and
harvesting the virions produced from the VPC; wherein presence of PSGL-1 on the surface of the virions blocks binding of the virions to its target cell to inactivate a viral infection of the retrovirus.

16. The method of claim 1, wherein the mutant comprises a cytoplasmic (CT) region.

17. The method of claim 15, wherein about 1 μg of the retroviral vector with about 0.5 ng to 400 ng of the expression vector is co-transfected in the VPC to produce the virions expressing PSGL-1 on its surface.

18. The method of claim 1, wherein the virions produced by the method are configured to inhibit the viral infection of the retrovirus in vitro or in vivo.

19. A method comprising:
taking P-selectin glycoprotein ligand-1 (PSGL-1);
co-transfecting a viral vector of a non-retrovirus comprising an influenza virus and an expression vector comprising the PSGL-1 in a virus-producing cell (VPC) comprising a cell line of a human;
expressing the PSGL-1 on a surface of virions produced from the VPC such that the PSGL-1 is incorporated into a viral particle during a virion assembly and expressed on the surface of the virions produced due to introduction of the viral vector in the VPC;
harvesting the virions produced from the VPC; and wherein presence of PSGL-1 on the surface of the virions blocks binding of the virions to its target cell.

20. The method of claim 19, wherein the virions produced by the method are configured to inhibit a viral infection of the influenza virus in vitro or in vivo.

* * * * *

SEQUENCE LISTING

```
<160> NUMBER OF SEQ ID NOS: 8

<210> SEQ ID NO 1
<211> LENGTH: 412
<212> TYPE: PRT
<213> ORGANISM: Homo sapiens

<400> SEQUENCE: 1

Met Pro Leu Gln Leu Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
        35                  40                  45

Leu Asp Tyr Asp Phe Leu Pro Glu Thr Glu Pro Pro Glu Met Leu Arg
    50                  55                  60
```

```
Asn Ser Thr Asp Thr Thr Pro Leu Thr Gly Pro Gly Thr Pro Glu Ser
 65                  70                  75                  80

Thr Thr Val Glu Pro Ala Ala Arg Arg Ser Thr Gly Leu Asp Ala Gly
                 85                  90                  95

Gly Ala Val Thr Glu Leu Thr Thr Glu Leu Ala Asn Met Gly Asn Leu
                100                 105                 110

Ser Thr Asp Ser Ala Ala Met Glu Ile Gln Thr Thr Gln Pro Ala Ala
            115                 120                 125

Thr Glu Ala Gln Thr Thr Gln Pro Val Pro Thr Glu Ala Gln Thr Thr
        130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
                165                 170                 175

Ala Ala Thr Glu Ala Gln Thr Thr Gln Pro Thr Gly Leu Glu Ala Gln
            180                 185                 190

Thr Thr Ala Pro Ala Ala Met Glu Ala Gln Thr Thr Ala Pro Ala Ala
        195                 200                 205

Met Glu Ala Gln Thr Thr Pro Pro Ala Ala Met Glu Ala Gln Thr Thr
210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
                245                 250                 255

Ala Ala Met Glu Ala Leu Ser Thr Glu Pro Ser Ala Thr Glu Ala Leu
            260                 265                 270

Ser Met Glu Pro Thr Thr Lys Arg Gly Leu Phe Ile Pro Phe Ser Val
        275                 280                 285

Ser Ser Val Thr His Lys Gly Ile Pro Met Ala Ala Ser Asn Leu Ser
        290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
                325                 330                 335

Cys Thr Val Val Leu Ala Val Arg Leu Ser Arg Lys Gly His Met Tyr
            340                 345                 350

Pro Val Arg Asn Tyr Ser Pro Thr Glu Met Val Cys Ile Ser Ser Leu
        355                 360                 365

Leu Pro Asp Gly Gly Glu Gly Pro Ser Ala Thr Ala Asn Gly Gly Leu
        370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
                405                 410

<210> SEQ ID NO 2
<211> LENGTH: 350
<212> TYPE: PRT
<213> ORGANISM: Homo sapiens

<400> SEQUENCE: 2

Met Pro Leu Gln Leu Leu Leu Leu Ile Leu Leu Gly Pro Gly Asn
 1               5                  10                  15

Ser Leu Gln Leu Trp Asp Thr Trp Ala Asp Glu Ala Glu Lys Ala Leu
                20                  25                  30
```

Gly Pro Leu Leu Ala Arg Asp Arg Arg Gln Ala Thr Glu Tyr Glu Tyr
            35                  40                  45

Leu Asp Tyr Asp Phe Leu Pro Glu Thr Glu Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Gln Pro Ala Ala
            115                 120                 125

Thr Glu Ala Gln Thr Thr Gln Pro Val Pro Thr Glu Ala Gln Thr Thr
    130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
            165                 170                 175

Ala Ala Thr Glu Ala Gln Thr Thr Gln Pro Thr Gly Leu Glu Ala Gln
            180                 185                 190

Thr Thr Ala Pro Ala Ala Met Glu Ala Gln Thr Thr Ala Pro Ala Ala
            195                 200                 205

Met Glu Ala Gln Thr Thr Pro Pro Ala Ala Met Glu Ala Gln Thr Thr
            210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
            245                 250                 255

Ala Ala Met Glu Ala Leu Ser Thr Glu Pro Ser Ala Thr Glu Ala Leu
            260                 265                 270

Ser Met Glu Pro Thr Thr Lys Arg Gly Leu Phe Ile Pro Phe Ser Val
            275                 280                 285

Ser Ser Val Thr His Lys Gly Ile Pro Met Ala Ala Ser Asn Leu Ser
            290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
            325                 330                 335

Cys Thr Val Leu Ala Val Arg Leu Ser Arg Lys Gly His
            340                 345                 350

<210> SEQ ID NO 3
<211> LENGTH: 101
<212> TYPE: PRT
<213> ORGANISM: Homo sapiens

<400> SEQUENCE: 3

Pro Asp His Ile Ser Val Lys Gln Cys Leu Leu Ala Ile Leu Ile Leu
1               5                   10                  15

Ala Leu Val Ala Thr Ile Phe Phe Val Cys Thr Val Leu Ala Val
            20                  25                  30

Arg Leu Ser Arg Lys Gly His Met Tyr Pro Val Arg Asn Tyr Ser Pro
            35                  40                  45

Thr Glu Met Val Cys Ile Ser Ser Leu Leu Pro Asp Gly Gly Glu Gly
            50                  55                  60

Pro Ser Ala Thr Ala Asn Gly Gly Leu Ser Lys Ala Lys Ser Pro Gly
 65                  70                  75                  80

Leu Thr Pro Glu Pro Arg Glu Asp Arg Glu Gly Asp Asp Leu Thr Leu
                85                  90                  95

His Ser Phe Leu Pro
            100

<210> SEQ ID NO 4
<211> LENGTH: 95
<212> TYPE: PRT
<213> ORGANISM: Homo sapiens

<400> SEQUENCE: 4

Lys Gln Cys Leu Leu Ala Ile Leu Ile Leu Ala Leu Val Ala Thr Ile
 1               5                  10                  15

Phe Phe Val Cys Thr Val Val Leu Ala Val Arg Leu Ser Arg Lys Gly
                20                  25                  30

His Met Tyr Pro Val Arg Asn Tyr Ser Pro Thr Glu Met Val Cys Ile
            35                  40                  45

Ser Ser Leu Leu Pro Asp Gly Gly Glu Gly Pro Ser Ala Thr Ala Asn
        50                  55                  60

Gly Gly Leu Ser Lys Ala Lys Ser Pro Gly Leu Thr Pro Glu Pro Arg
 65                  70                  75                  80

Glu Asp Arg Glu Gly Asp Asp Leu Thr Leu His Ser Phe Leu Pro
                85                  90                  95

<210> SEQ ID NO 5
<211> LENGTH: 95
<212> TYPE: PRT
<213> ORGANISM: Homo sapiens

<400> SEQUENCE: 5

Lys Gln Cys Leu Leu Ala Ile Leu Ile Leu Ala Leu Val Ala Thr Ile
 1               5                  10                  15

Phe Phe Val Cys Thr Val Val Leu Ala Val Ala Leu Ser Ala Ala Gly
                20                  25                  30

His Met Tyr Pro Val Arg Asn Tyr Ser Pro Thr Glu Met Val Cys Ile
            35                  40                  45

Ser Ser Leu Leu Pro Asp Gly Gly Glu Gly Pro Ser Ala Thr Ala Asn
        50                  55                  60

Gly Gly Leu Ser Lys Ala Lys Ser Pro Gly Leu Thr Pro Glu Pro Arg
 65                  70                  75                  80

Glu Asp Arg Glu Gly Asp Asp Leu Thr Leu His Ser Phe Leu Pro
                85                  90                  95

<210> SEQ ID NO 6
<211> LENGTH: 95
<212> TYPE: PRT
<213> ORGANISM: Homo sapiens

<400> SEQUENCE: 6

Lys Gln Cys Leu Leu Ala Ile Leu Ile Leu Ala Leu Val Ala Thr Ile
 1               5                  10                  15

Phe Phe Val Cys Thr Val Val Leu Ala Val Arg Leu Ser Arg Lys Gly
                20                  25                  30

```
His Met Tyr Pro Val Arg Asn Tyr Ser Pro Thr Glu Met Val Cys Ile
            35                  40                  45

Ser Ser Leu Leu Pro Asp Gly Gly Glu Gly Pro Ser Ala Thr Ala Asn
 50                  55                  60

Gly Gly Leu Ser Lys Ala Lys Ser Pro Gly Leu Thr Pro Ala Pro Arg
65                   70                  75                  80

Ala Ala Arg Ala Gly Ala Ala Leu Thr Leu His Ser Phe Leu Pro
                85                  90                  95

<210> SEQ ID NO 7
<211> LENGTH: 95
<212> TYPE: PRT
<213> ORGANISM: Homo sapiens

<400> SEQUENCE: 7

Lys Gln Ala Leu Leu Ala Ile Leu Ile Leu Ala Leu Val Ala Thr Ile
1               5                   10                  15

Phe Phe Val Cys Thr Val Val Leu Ala Val Arg Leu Ser Arg Lys Gly
            20                  25                  30

His Met Tyr Pro Val Arg Asn Tyr Ser Pro Thr Glu Met Val Cys Ile
            35                  40                  45

Ser Ser Leu Leu Pro Asp Gly Gly Glu Gly Pro Ser Ala Thr Ala Asn
 50                  55                  60

Gly Gly Leu Ser Lys Ala Lys Ser Pro Gly Leu Thr Pro Glu Pro Arg
65                   70                  75                  80

Glu Asp Arg Glu Gly Asp Asp Leu Thr Leu His Ser Phe Leu Pro
                85                  90                  95

<210> SEQ ID NO 8
<211> LENGTH: 23
<212> TYPE: PRT
<213> ORGANISM: Homo sapiens

<400> SEQUENCE: 8

Lys Gln Cys Leu Leu Ala Ile Leu Ile Leu Ala Leu Val Ala Thr Ile
1               5                   10                  15

Phe Phe Val Cys Thr Val Val
            20
```